United States Patent
Hayer et al.

(10) Patent No.: US 10,847,727 B2
(45) Date of Patent: Nov. 24, 2020

(54) COMPOSITIONS FOR ELECTRONIC DEVICES

(71) Applicant: Merck Patent GmbH, Darmstadt (DE)

(72) Inventors: Anna Hayer, Darmstadt (DE); Florian Maier-Flaig, Weinheim (DE); Tobias Grossmann, Darmstadt (DE); Dominik Joosten, Frankfurt am Main (DE); Holger Heil, Frankfurt am Main (DE); Thomas Eberle, Landau (DE); Rémi Manouk Anémian, Seoul (KR)

(73) Assignee: Merck Patent GmbH, Darmstadt (DE)

( * ) Notice: Subject to any disclaimer, the term of this patent is extended or adjusted under 35 U.S.C. 154(b) by 453 days.

(21) Appl. No.: 15/319,459

(22) PCT Filed: May 26, 2015

(86) PCT No.: PCT/EP2015/001072
§ 371 (c)(1),
(2) Date: Dec. 16, 2016

(87) PCT Pub. No.: WO2015/192941
PCT Pub. Date: Dec. 23, 2015

(65) Prior Publication Data
US 2017/0141328 A1 May 18, 2017

(30) Foreign Application Priority Data
Jun. 18, 2014 (DE) .................. 10 2014 008 722

(51) Int. Cl.
*H01L 51/50* (2006.01)
*H01L 51/00* (2006.01)
*C09K 11/06* (2006.01)
*C07D 209/96* (2006.01)
*C07D 403/04* (2006.01)
*C07D 403/10* (2006.01)
*C07D 403/14* (2006.01)
*C07D 405/10* (2006.01)
*C07F 15/00* (2006.01)
*C09K 11/02* (2006.01)

(52) U.S. Cl.
CPC ........ *H01L 51/0072* (2013.01); *C07D 209/96* (2013.01); *C07D 403/04* (2013.01); *C07D 403/10* (2013.01); *C07D 403/14* (2013.01); *C07D 405/10* (2013.01); *C07F 15/0086* (2013.01); *C09K 11/025* (2013.01); *C09K 11/06* (2013.01); *H01L 51/006* (2013.01); *H01L 51/0052* (2013.01); *H01L 51/0054* (2013.01); *H01L 51/0056* (2013.01); *H01L 51/0059* (2013.01); *H01L 51/0061* (2013.01); *H01L 51/0067* (2013.01); *H01L 51/0073* (2013.01); *H01L 51/0074* (2013.01); *H01L 51/0085* (2013.01); *H01L 51/0087* (2013.01); *H01L 51/5004* (2013.01); *H01L 51/5016* (2013.01); *C07C 2603/18* (2017.05); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1074* (2013.01); *C09K 2211/1088* (2013.01); *C09K 2211/1092* (2013.01); *C09K 2211/185* (2013.01); *H01L 51/0058* (2013.01); *H01L 51/5056* (2013.01); *H01L 51/5072* (2013.01); *H01L 2251/5384* (2013.01); *H01L 2251/552* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 9,206,351 B2 | 12/2015 | Bach et al. | |
| 9,331,290 B2 | 5/2016 | Stoessel et al. | |
| 9,444,064 B2 | 9/2016 | Kaiser et al. | |
| 2004/0247933 A1 | 12/2004 | Thoms | |
| 2006/0068223 A1 | 3/2006 | Nariyuki et al. | |
| 2010/0184942 A1* | 7/2010 | Chen | C07D 209/82 528/423 |
| 2012/0056169 A1* | 3/2012 | Kaiser | H01L 51/008 257/40 |
| 2015/0115240 A1 | 4/2015 | Fukumatsu et al. | |

FOREIGN PATENT DOCUMENTS

| | | |
|---|---|---|
| DE | 102006025777 A1 | 12/2007 |
| DE | 102010027317 A1 | 1/2012 |
| WO | WO-2005029923 A1 | 3/2005 |
| WO | WO-2009021126 A2 | 2/2009 |
| WO | WO-2010108579 A1 | 9/2010 |
| WO | WO-2013146645 A1 | 10/2013 |

OTHER PUBLICATIONS

International Search Report for PCT/EP2015/001072 dated Jul. 31, 2015.
Written Opinion of the International Searching Authority for PCT/EP2015/001072 dated Jul. 31, 2015.

* cited by examiner

*Primary Examiner* — Gregory D Clark
(74) *Attorney, Agent, or Firm* — Faegre Drinker Biddle & Reath LLP

(57) ABSTRACT

The present invention relates to compositions and formulations for electronic devices comprising mixtures of organic functional materials.

22 Claims, No Drawings

COMPOSITIONS FOR ELECTRONIC DEVICES

CROSS-REFERENCE TO RELATED APPLICATIONS

This application is a national stage application (under 35 U.S.C. § 371) of PCT/EP2015/001072, filed May 26, 2015, which claims benefit of German Application No. 102014008722.0, filed Jun. 18, 2014, both of which are incorporated herein by reference in their entirety.

The present invention relates to a composition, and to a formulation and device comprising the composition.

BACKGROUND OF THE INVENTION

The structure of organic electroluminescent devices (for example OLEDs—organic light-emitting diodes, or OLECs—organic light-emitting electrochemical cells) in which organic semiconductors are employed as organic functional materials is described, for example, in U.S. Pat. Nos. 4,539,507, 5,151,629, EP 0676461 and WO 98/27136. The emitting materials employed here, besides fluorescent emitters, are increasingly organometallic complexes which exhibit phosphorescence (M. A. Baldo et al., Appl. Phys. Lett. 1999, 75, 4-6). For quantum-mechanical reasons, an up to four-fold increase in energy and power efficiency is possible using organometallic compounds as phosphorescence emitters. In general, there is still a need for improvement, in particular with respect to efficiency, operating voltage and lifetime, both in the case of OLEDs which exhibit singlet emission and also in the case of OLEDs which exhibit triplet emission.

The properties of organic electroluminescent devices are not determined only by the emitters employed. In particular, the other materials used, such as host materials, hole-blocking materials, electron-transport materials, hole-transport materials and electron- or exciton-blocking materials, are also of particular importance here. Improvements in these materials can result in significant improvements in electroluminescent devices.

Host materials for use in organic electronic devices are well known to the person skilled in the art. The term matrix material is frequently also used in the prior art to mean a host material for phosphorescent dopants. In the meantime, a multiplicity of host materials have been developed, both for fluorescent and for phosphorescent electronic devices.

For fluorescent OLEDs, use is made in accordance with the prior art of, in particular, condensed aromatic compounds, in particular anthracene derivatives, as host materials, in particular for blue-emitting electroluminescent devices, for example 9,10-bis(2-naphthyl)anthracene (U.S. Pat. No. 5,935,721).

WO 03/095445 and CN 1362464 disclose 9,10-bis(1-naphthyl)anthracene derivatives for use in OLEDs. Further anthracene derivatives are disclosed in WO 01/076323, in WO 01/021729, in WO 2004/013073, in WO 2004/018588, in WO 2003/087023 or in WO 2004/018587. Host materials based on aryl-substituted pyrenes and chrysenes are disclosed in WO 2004/016575. Host materials based on benzanthracene derivatives are disclosed in WO 2008/145239. For high-quality applications, it is desirable to have improved host materials available.

According to the prior art, use is made, inter alia, of ketones (for example in accordance with WO 2004/093207 or WO 2010/006680) or phosphine oxides (for example in accordance with WO 2005/003253) as host materials for phosphorescent emitters. Further host materials in accordance with the prior art are triazines (for example WO 2008/056746, EP 0906947, EP 0908787, EP 0906948).

WO 2012/074210 discloses the use of fluorenes and spirobifluorenes as host materials.

The prior art discloses the use of compounds containing one or more carbazole groups in electronic devices, for example in WO 2005/039246, US 2005/0069729, JP 2004/288381, EP 1205527 or WO 2008/086851.

The prior art furthermore discloses the use of compounds containing one or more indenocarbazole groups in electronic devices, for example in WO 2010/136109 and WO 2011/000455.

WO 2007/063754 discloses the use of indolocarbazoles as host materials.

The prior art furthermore discloses the use of compounds containing one or more electron-deficient heteroaromatic six-membered rings in electronic devices, for example in WO 2010/015306, WO 2007/063754 and WO 2008/056746.

WO 2009/069442 discloses tricyclic compounds, such as carbazole, dibenzofuran or dibenzothiophene, which are highly substituted by electron-deficient heteroaromatic groups (for example pyridine, pyrimidine or triazine). The tricyclic compounds are not substituted by hole-conducting groups, i.e. electron-rich groups.

JP 2009-21336 discloses substituted dibenzofurans which are substituted by carbazole in the 2 position and by a triazine in the 8 position.

WO 2011/057706 discloses dibenzothiophenes and dibenzofurans, some of which are substituted, as host materials, where the compounds are substituted in a specific manner by an electron-conducting group and by a hole-conducting group.

A further possibility for improving the performance data of electronic devices, in particular of electroluminescent devices, consists in using combinations of materials.

U.S. Pat. No. 6,392,250 B1 discloses the use of a mixture consisting of an electron-transport material, a hole-transport material and a fluorescent emitter in the emission layer of an OLED. With the aid of this mixture, it has been possible to improve the lifetime of the OLED compared with the prior art.

U.S. Pat. No. 6,803,720 B1 discloses the use of a mixture comprising a phosphorescent emitter and a hole-transport material and an electron-transport material in the emission layer of an OLED. Both the hole-transport material and the electron-transport material are small organic molecules.

Furthermore, U.S. Pat. No. 7,294,849 B2 discloses the use of a mixture comprising a host material, a hole-transport material or electron-transport material and a phosphorescent emitter in the emission layer of an OLED. If a hole-transport material is used in the mixture, the energy of the HOMO (highest occupied molecular orbital) of the host material must be lower than that of the hole-transport material. Furthermore, the LUMO (lowest unoccupied molecular orbital) energy of the host material must then be higher than that of the phosphorescent emitter. If an electron-transport material is used in the mixture, the energy of the HOMO (highest occupied molecular orbital) of the host material must be lower than that of the phosphorescent emitter.

Furthermore, the LUMO (lowest unoccupied molecular orbital) energy of the host material must then be higher than that of the electron-transport material. The host material is a wide band gap material which is characterised by a band gap of at least 3.5 eV, where band gap is taken to mean the separation between HOMO and LUMO energy of a material.

However, there is still a need for improvement on use of these materials as in the case of other materials or on use of mixtures of the materials, in particular with respect to the efficiency and the lifetime of the organic electronic device.

The object of the present invention is therefore the provision of compositions which are suitable for use in a fluorescent or phosphorescent OLED and which, on use in an OLED, result in good device properties, and the provision of the corresponding electronic device.

Surprisingly, it has been found that certain compositions described in greater detail below achieve these objects and overcome the disadvantages from the prior art. The compositions result in very good properties of organic electronic devices, in particular organic electroluminescent devices, in particular with respect to the lifetime, the efficiency and the operating voltage.

The present invention therefore relates to electronic devices, in particular organic electroluminescent devices, which comprise compositions of this type, and to the corresponding preferred embodiments. The surprising effects are achieved by a very specific selection of known materials.

The present invention relates to a composition comprising a bipolar host, a neutral co-host and a light-emitting dopant.

Both the bipolar host and also the neutral co-host are organic compounds, whereas the light-emitting dopant can be an organic, organometallic or inorganic compound. The individual compounds are well known to the person skilled in the art from the prior art, so that he will be able to make a choice from a multiplicity of compounds available to him.

The composition according to the invention is suitable in a particularly advantageous manner for use in organic electronic devices. Organic electroluminescent devices comprising these compositions have very good efficiencies, operating voltages and significantly increased lifetimes.

The concentration of the light-emitting dopant in the composition is preferably in the range from 0.1% by weight to 50% by weight, very preferably in the range from 1% by weight to 30% by weight and very particularly preferably in the range from 5% by weight to 20% by weight, based on the entire composition.

BRIEF SUMMARY OF THE INVENTION

The concentration of the neutral co-host in the composition is preferably in the range from 5% by weight to 70% by weight, very preferably in the range from 20% by weight to 60% by weight and very particularly preferably in the range from 30% by weight to 60% by weight, based on the entire composition.

The concentration of the bipolar host in the composition is preferably in the range from 5% by weight to 70% by weight, very preferably in the range from 10% by weight to 60% by weight and very particularly preferably in the range from 20% by weight to 50% by weight, based on the entire composition.

It is preferred for the purposes of the present invention if the dopant of the composition is a phosphorescent emitter.

DETAILED DESCRIPTION OF THE INVENTION

The term phosphorescent dopants or emitters typically encompasses compounds in which the light emission takes place through a spin-forbidden transition, for example through a transition from a triplet state or a state having an even higher spin quantum number, for example a quintet state. This is preferably taken to mean a transition from a triplet state.

Suitable phosphorescent dopants or emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present application, all luminescent iridium, platinum or copper complexes are regarded as phosphorescent compounds.

Preferred phosphorescent dopants are organic compounds and organic metal complexes, where organic metal complexes are very preferred.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/157339, WO 2012/007086, WO 2012/163471, WO 2013/000531 and WO 2013/020631. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

Examples of suitable phosphorescent emitters which are well known from the prior art are depicted in the following table.

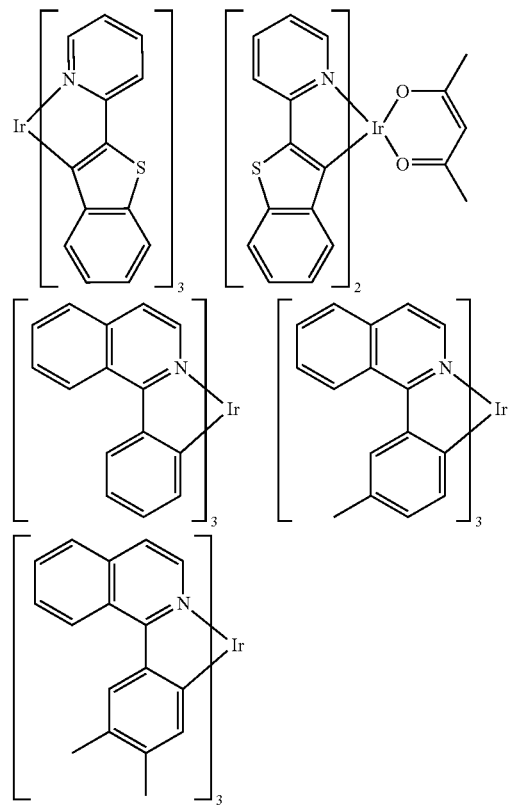

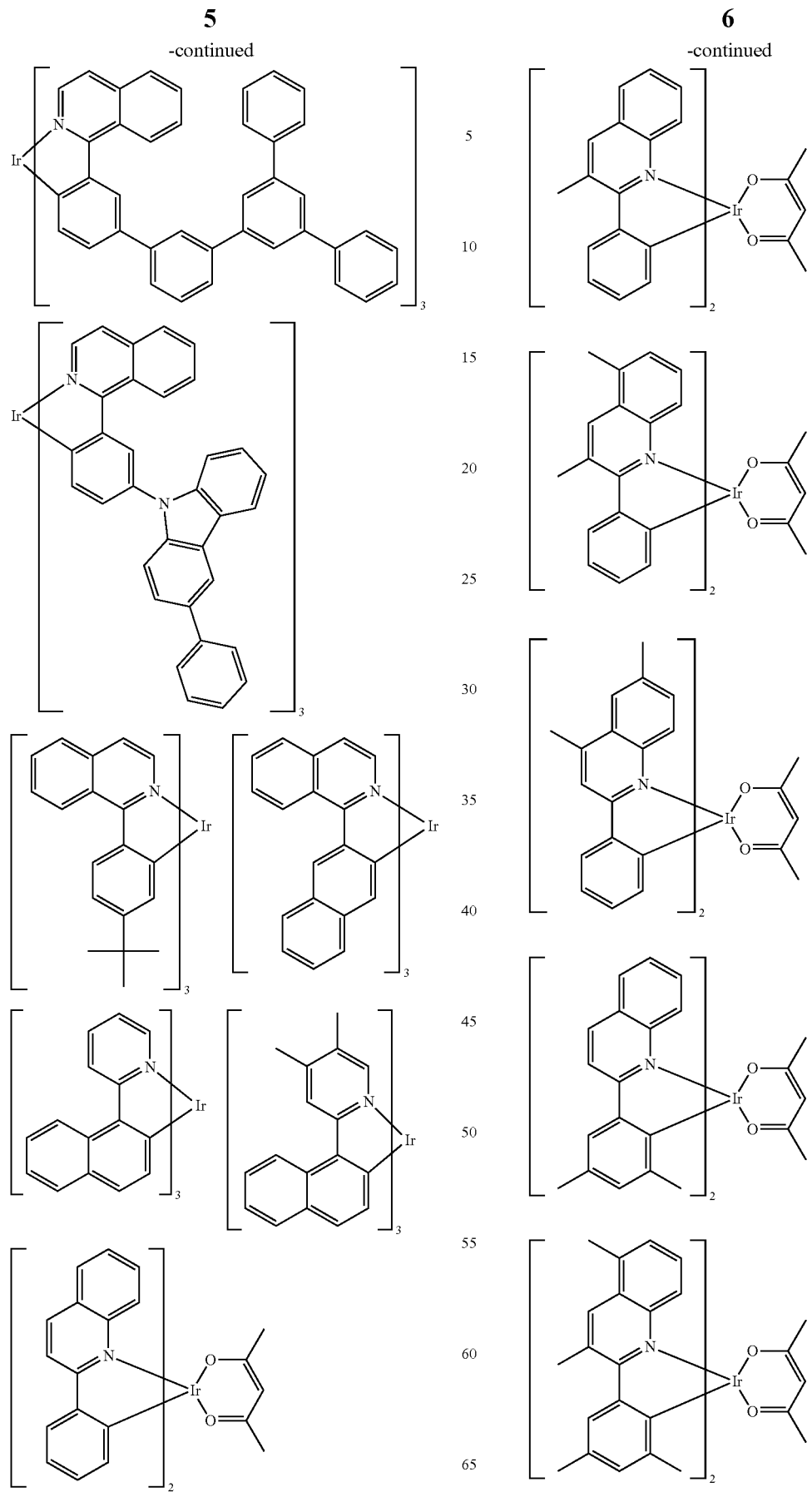

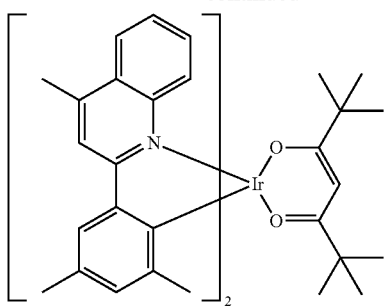
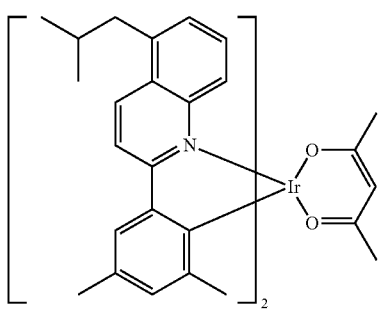
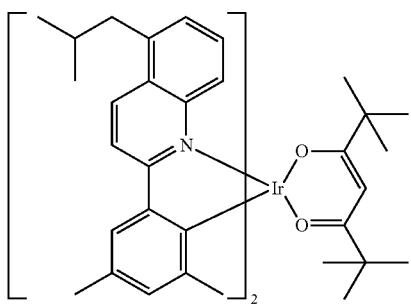
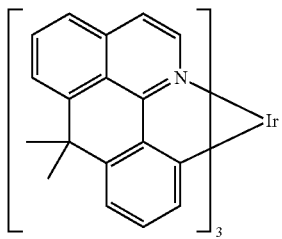
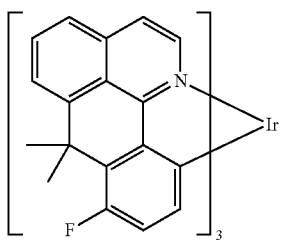
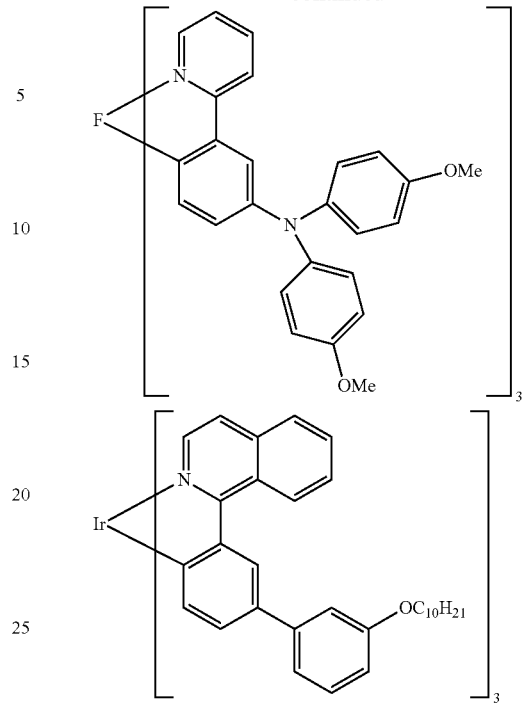
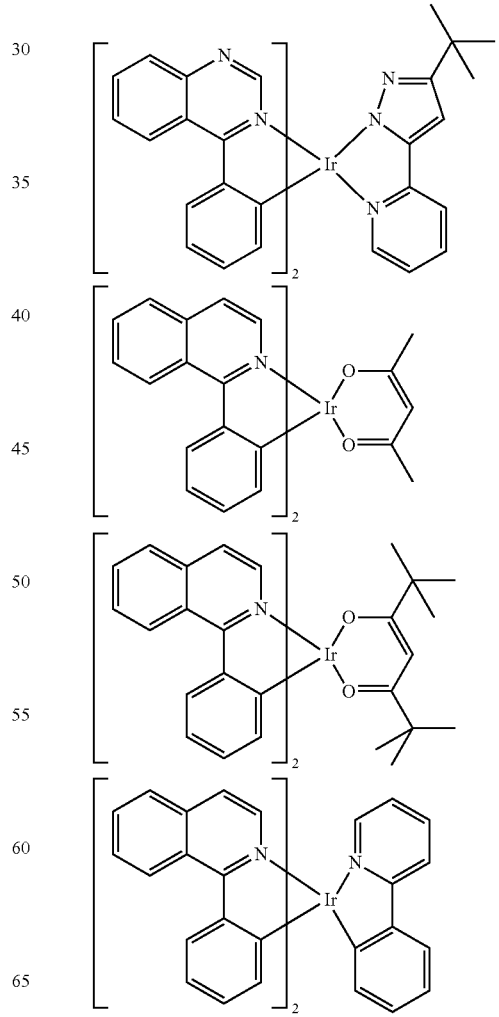

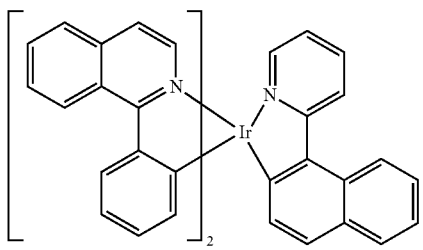
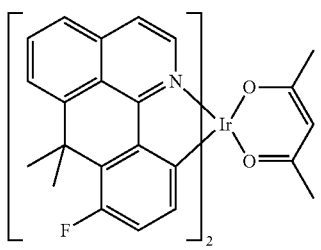
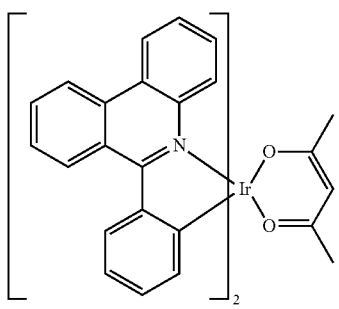
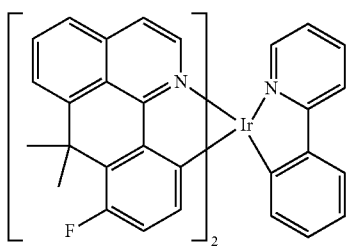
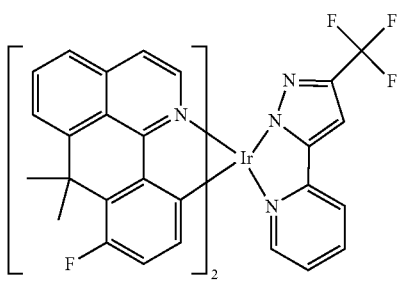
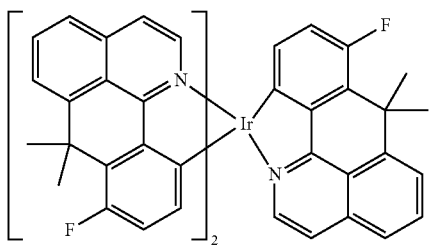
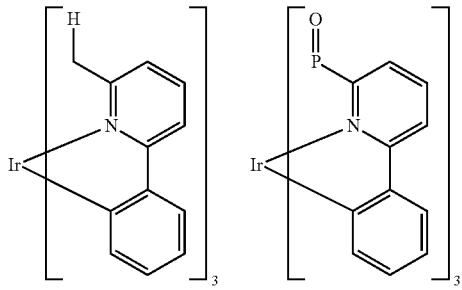
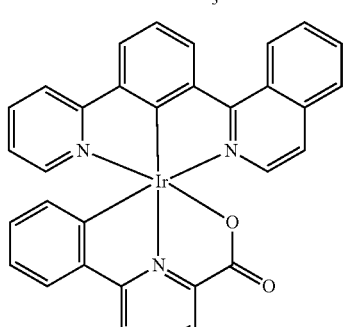
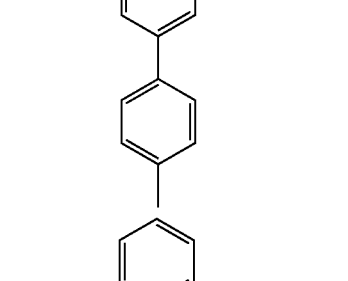
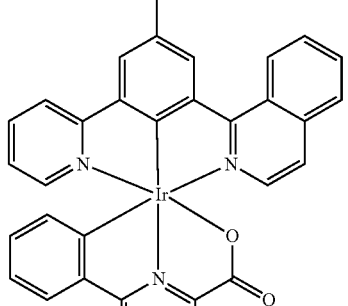
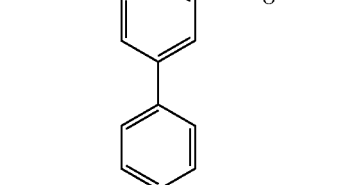
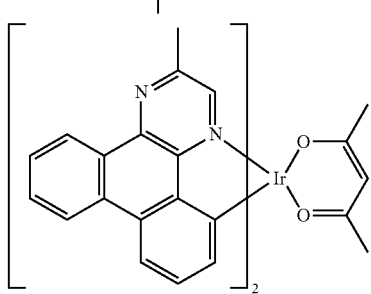

-continued
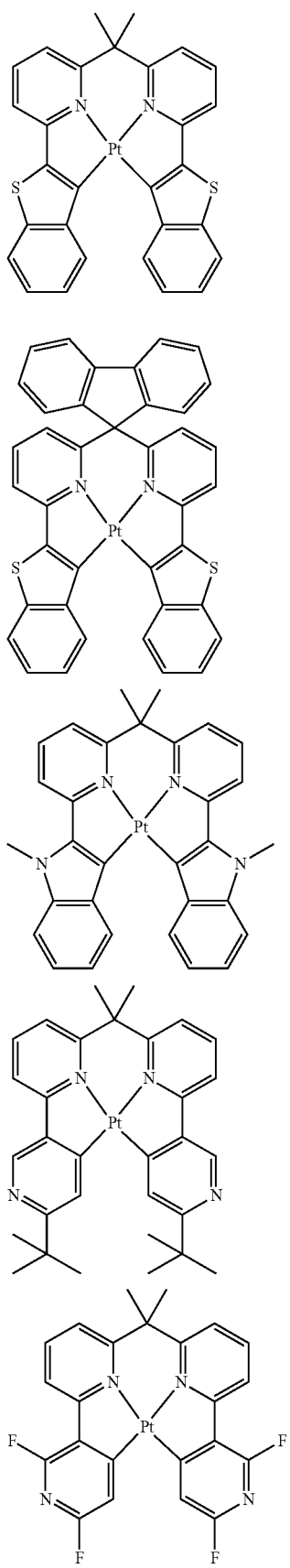
-continued
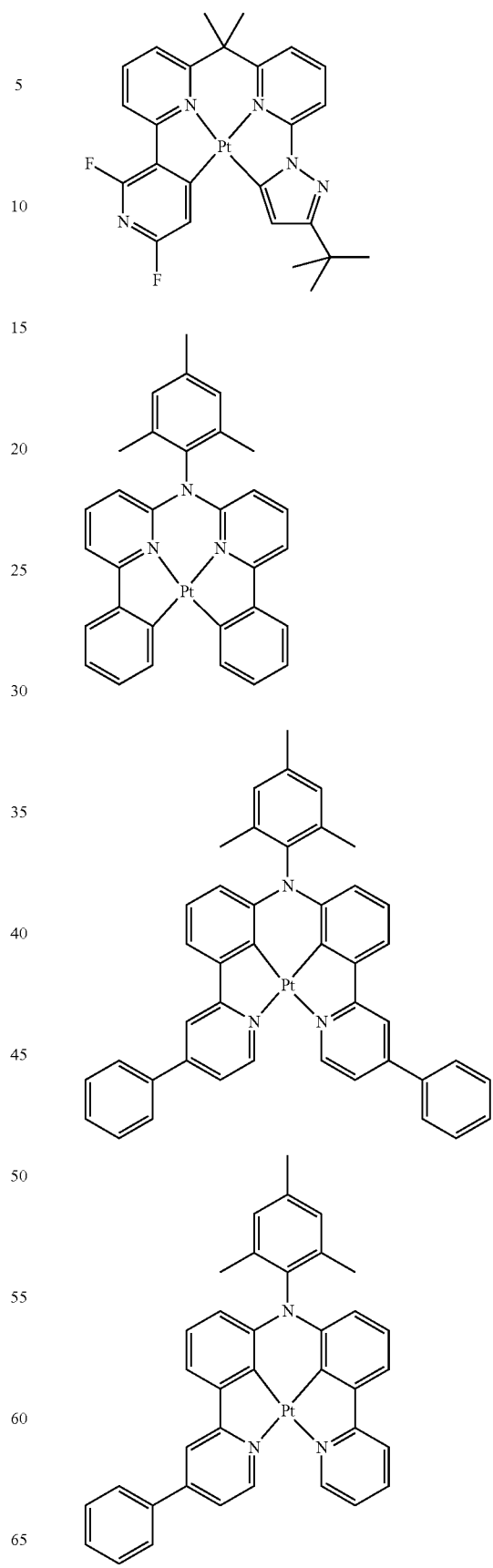

-continued
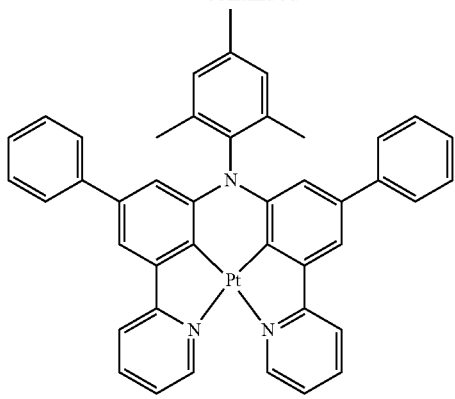
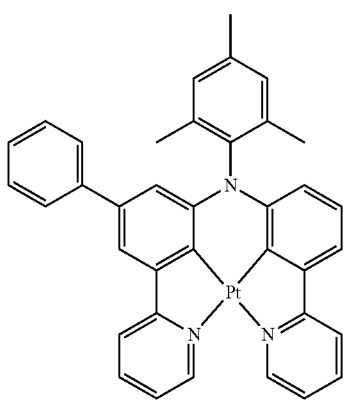
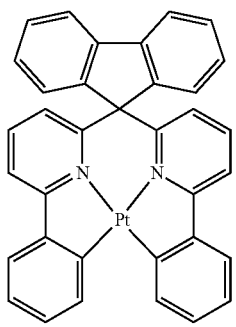
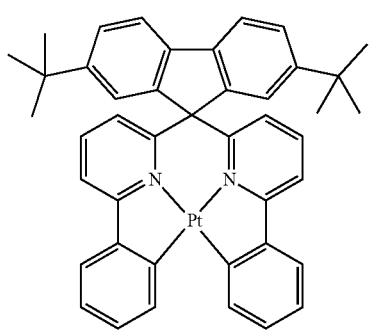
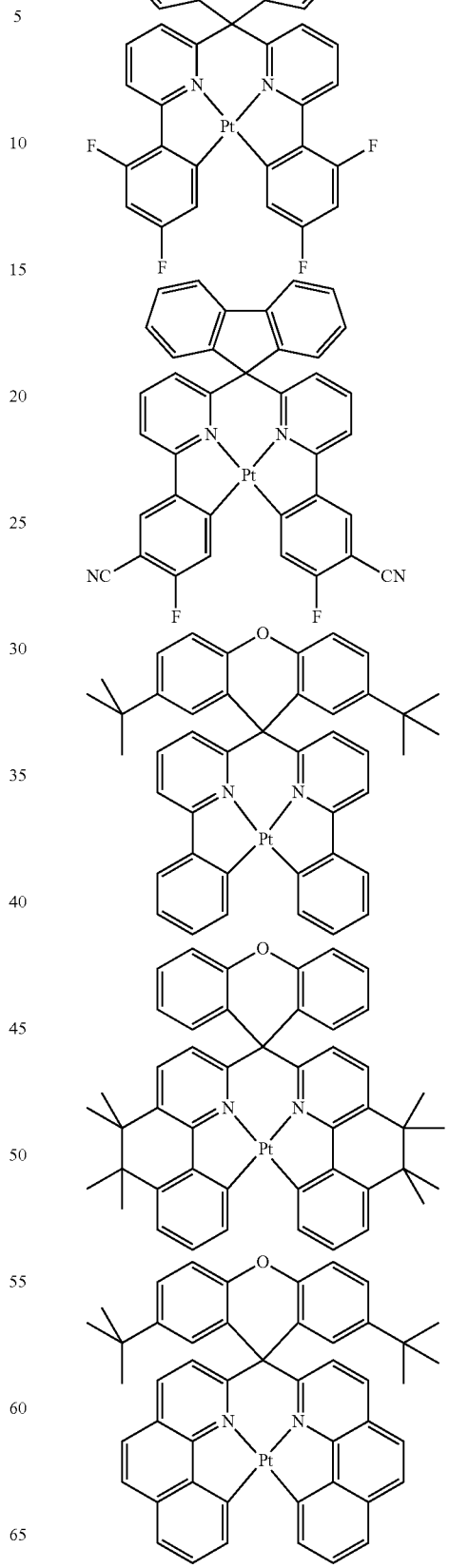

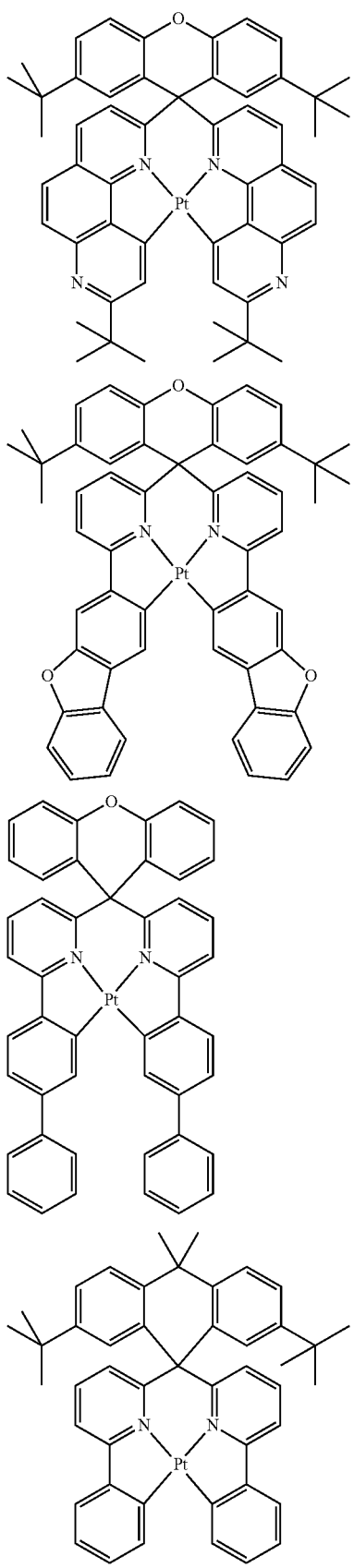
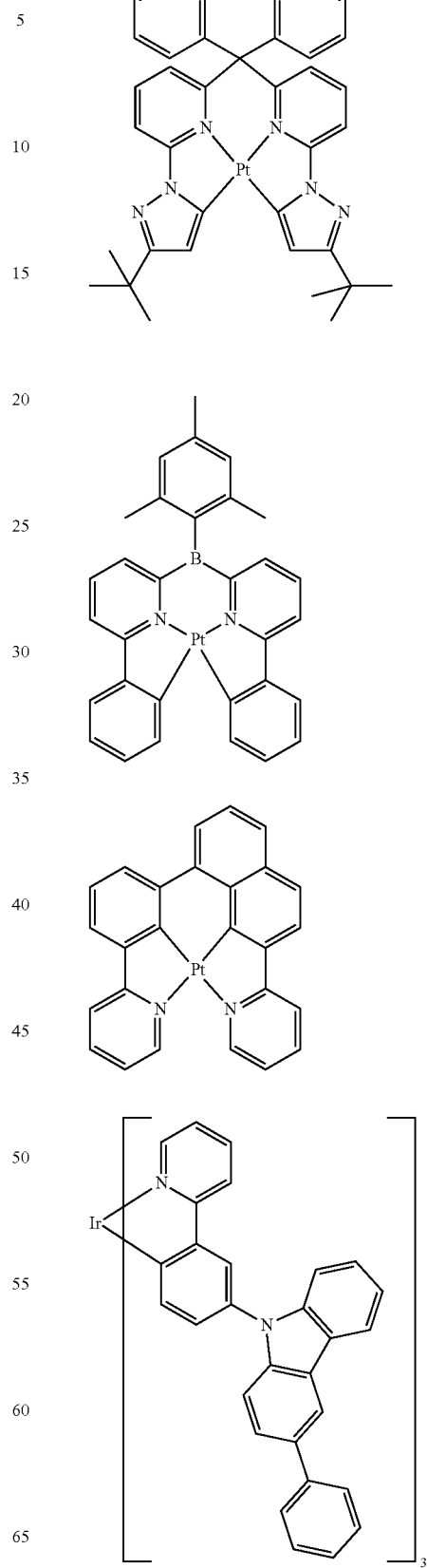

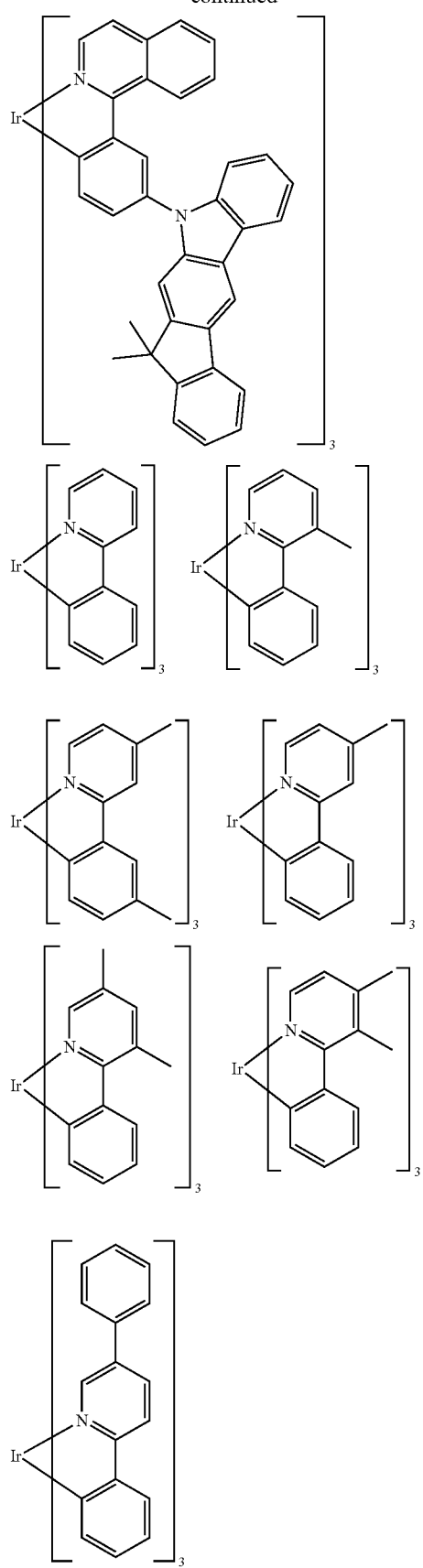
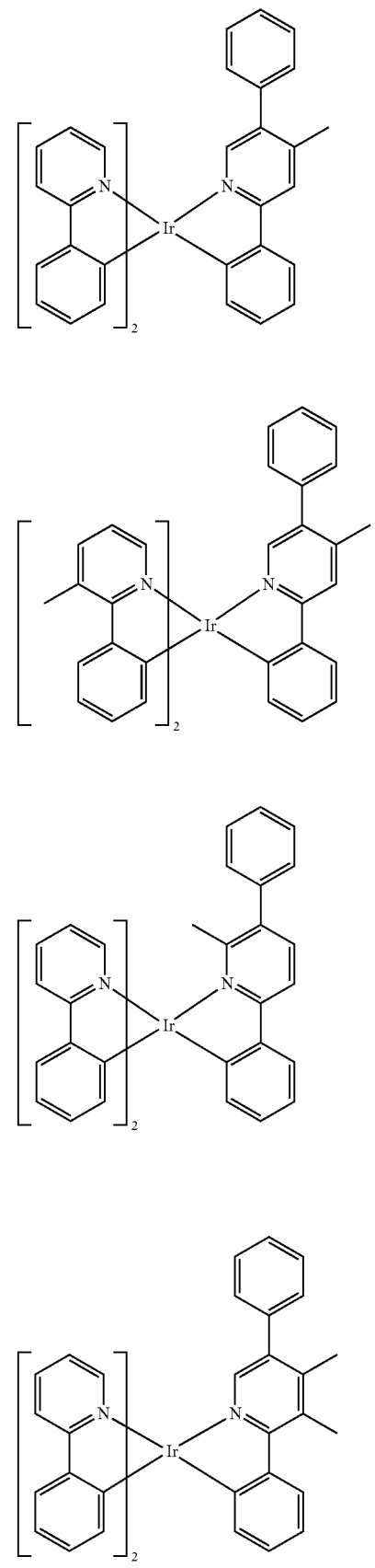

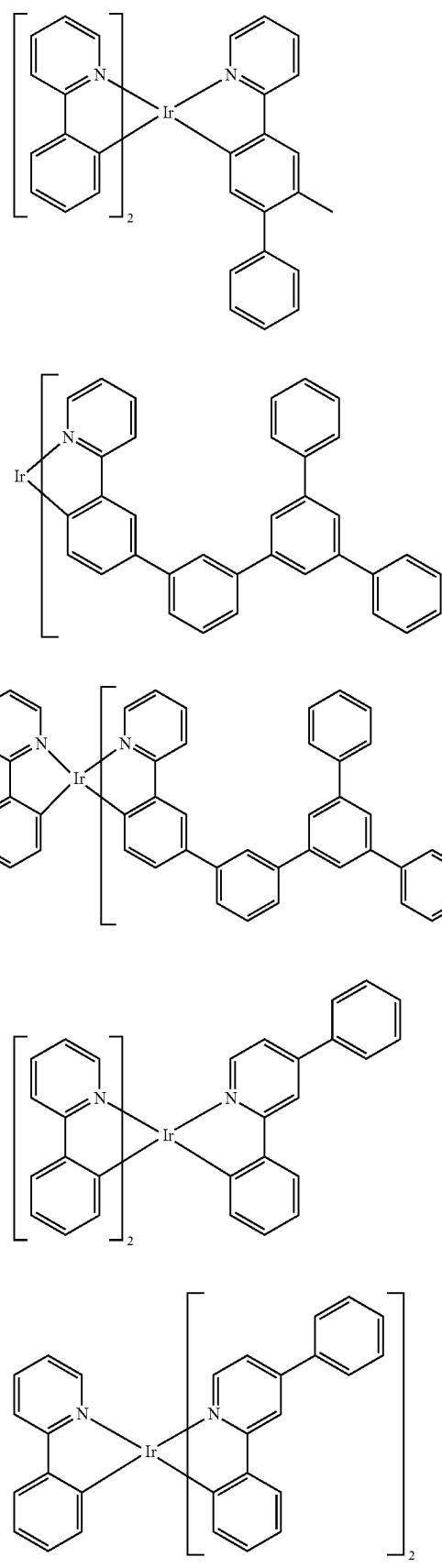
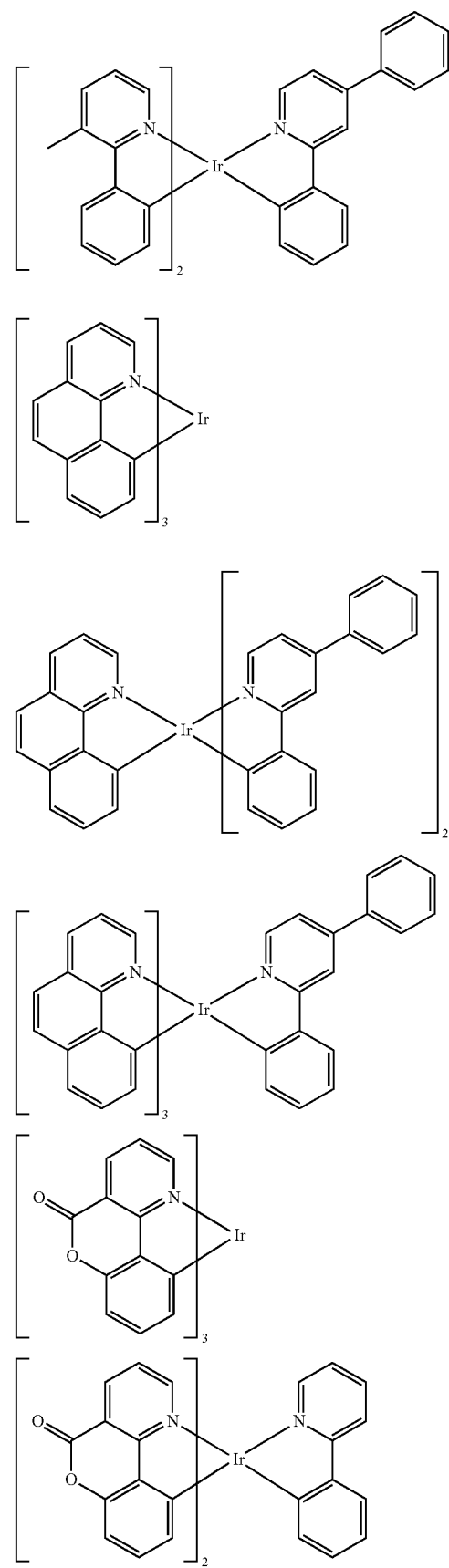

-continued
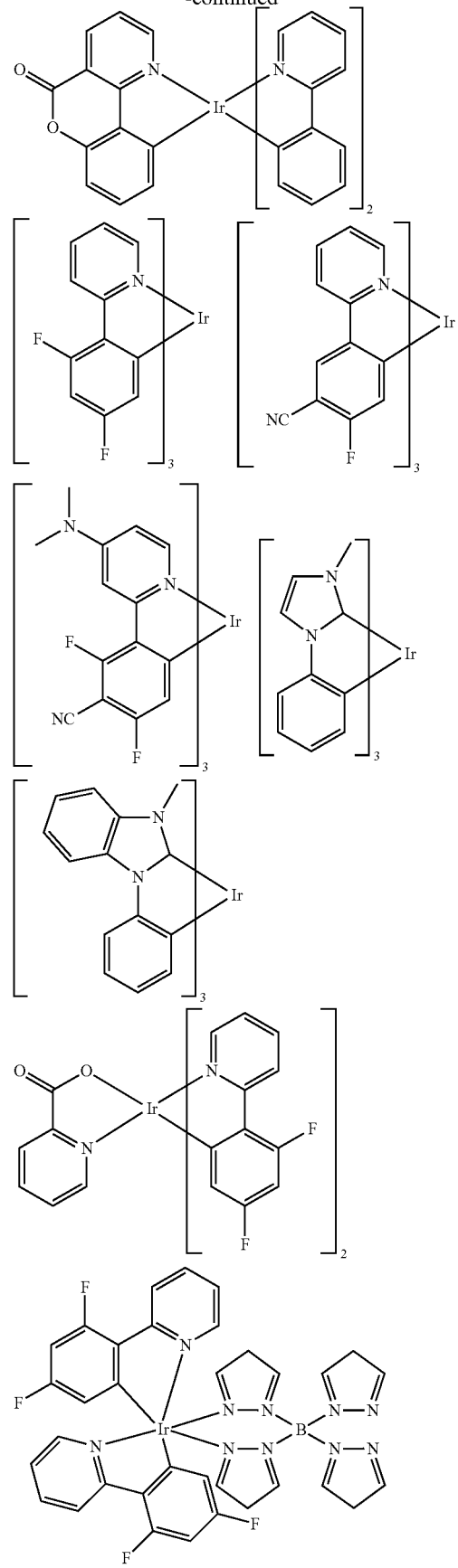
-continued
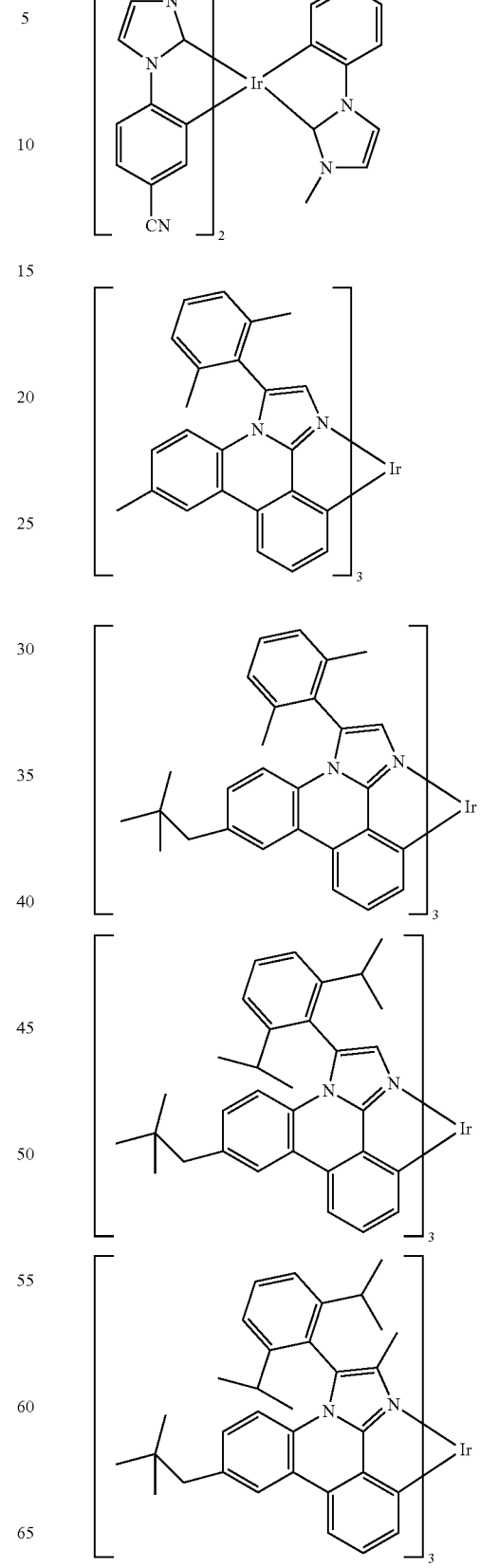

-continued

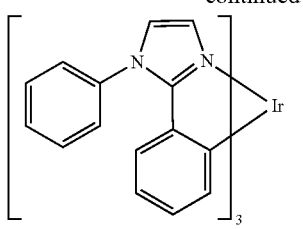

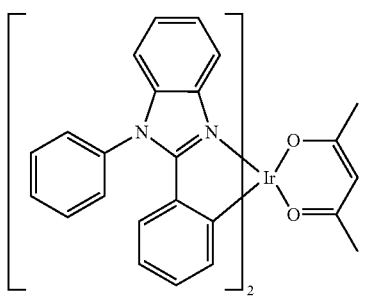

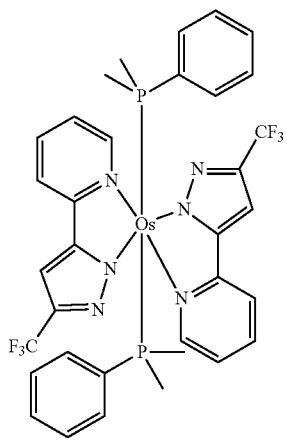

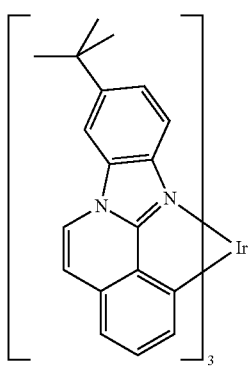

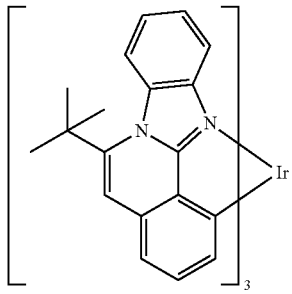

-continued

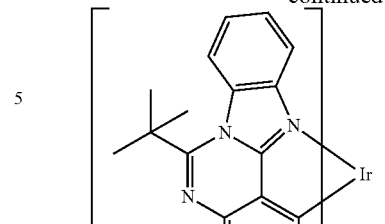

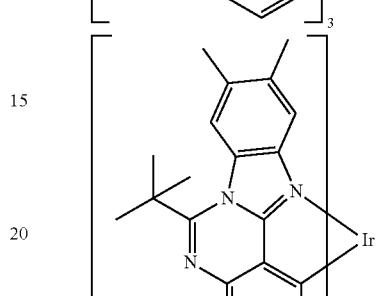

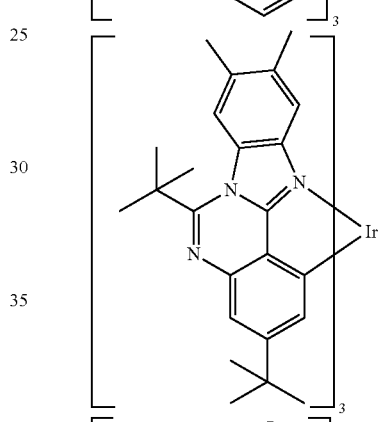

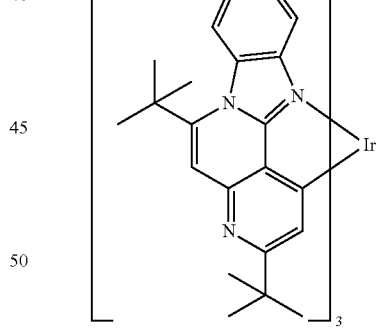

It is particularly advantageous with respect to the performance data and lifetime of electronic devices if the components of the composition satisfy the following conditions:

$|HOMO(C)|-\min\{|HOMO(D)|;|HOMO(B)|\}>0.3$ $||HOMO(B)|-|HOMO(D)||<0.15$ eV $||LUMO(B)|-|LUMO(C)||>0.3$ eV $||LUMO(B)|-|LUMO(D)||>0$, where HOMO(C) stands for the HOMO energy of the neutral co-host, HOMO(B) and HOMO(D) correspondingly stand for the HOMO energy of the bipolar host and of the dopant respectively, LUMO(C), LUMO(B) and LUMO(D) correspondingly stand for the LUMO energy of the neutral co-host, of the bipolar host and of the dopant respectively, and the function min{|HOMO(D)|; |HOMO(B)|} supplies the smaller of the two values |HOMO(D)| and |HOMO(B)| and where |HOMO| and |LUMO| stand for the modulus of the respective value.

The energy values indicated relate to isolated compounds here and are determined as described below.

The HOMO (highest occupied molecular orbital) and LUMO (lowest unoccupied molecular orbital) energies and the triplet level of the materials are determined via quantum-chemical calculations. To this end, the "Gaussian09, Revision D.01" software package (Gaussian Inc.) is used here. However, other software packages can also be used so long as the same methods have been implemented therein. In order to calculate organic substances without metals (denoted by method "org." in Table 5), firstly a geometry optimisation is carried out using the semi-empirical method AM1 (Gaussian input line "#AM1 opt") with charge 0 and multiplicity 1. An energy calculation (single point) for the electronic ground state and triplet level is subsequently carried out on the basis of the optimised geometry. The TDDFT (time dependent density functional theory) method B3PW91 with the 6-31G(d) base set (Gaussian input line "#B3PW91/6-31G(d) td=(50-50,nstates=4)") is used here (charge 0, multiplicity 1). For organometallic compounds (denoted by method "org.-m" in Table 5), the geometry is optimised using the Hartree-Fock method and the LanL2 MB base set (Gaussian input line "#HF/LanL2 MB opt") (charge 0, multiplicity 1). The energy calculation is carried out analogously to the organic substances, as described above, with the difference that the "LanL2DZ" base set is used for the metal atom and the "6-31G(d)" base set is used for the ligands (Gaussian input line "#B3PW91/gen pseudo=lanl2 td=(50-50,nstates=4)"). The energy calculation gives the HOMO as the final orbital occupied by two electrons (Alpha occ. eigenvalues) and the LUMO as the first unoccupied orbital (Alpha virt. eigenvalues) in hartree units (HEh or LEh). The HOMO and LUMO value in electron volts calibrated with reference to cyclic voltammetry measurements is determined therefrom as follows:

LUMO(eV)=(1.0658*LEh*27.212)−0.5049

HOMO(eV)=(0.8308*HEh*27.212)−1.1180

These values are to be regarded as HOMO or LUMO of the materials for the purposes of this application.

The triplet level $T_1$ of a material is defined as the relative excitation energy (in eV) of the triplet state having the lowest energy which arises from the quantum-chemical energy calculation.

The above-mentioned conditions and the method for determining the individual energy values allow the person skilled in the art to identify the suitable compounds from the prior art in a simple manner. The calculation of orbital energies represents a routine activity for the person skilled in the art, which he can carry out in a short time with the aid of the above-mentioned method.

It is furthermore preferred if the following conditions are satisfied:

|HOMO(B)|−|HOMO(D)|<0.15 eV and

|HOMO(B)|−|HOMO(D)|>−0.2 eV, where it is very preferred if

|HOMO(B)|−|HOMO(D)|<0.1 eV and

|HOMO(B)|−|HOMO(D)|>−0.1 eV.

It is very preferred if the following condition is satisfied:

|HOMO(C)|−min{|HOMO(D)|;|HOMO(B)|}>0.4 eV, where it is particularly preferred if

|HOMO(C)|−min{|HOMO(D)|;|HOMO(B)|}>0.6 eV.

It is very particularly preferred if the following condition is satisfied:

|LUMO(B)|−|LUMO(C)|>0.4 eV, where it is especially preferred if

|LUMO(B)|−|LUMO(C)|>0.6 eV.

Especial preference is given to a composition which is characterised in that at least one of the two following conditions is satisfied:

|HOMO(C)|−min{|HOMO(D)|;|HOMO(B)|}>0.4 eV or

|LUMO(B)|−|LUMO(C)|>0.4 eV, where it is more preferred if both conditions are satisfied, and where it is even more preferred if, in addition, one of the two following conditions is satisfied:

|HOMO(C)|−min{|HOMO(D)|;|HOMO(B)|}>0.6 eV or

|LUMO(B)|−|LUMO(C)|>0.6 eV, and where it is most preferred if both conditions are satisfied.

In a further embodiment of the present invention, the composition comprises a bipolar host, a neutral co-host and a light-emitting dopant, which is preferably a phosphorescent emitter, which is very preferably an organic phosphorescent emitter, characterised in that the following conditions are satisfied:

max{|LUMO(D)|;|LUMO(B)|}−|LUMO(C)|>0.3 eV

|LUMO(D)|−|LUMO(B)|−<0.15 eV

|HOMO(C)|−|HOMO(B)|>0.3 eV

|HOMO(D)|−|HOMO(B)|>0, where the function max{|LUMO(D)|; |LUMO(B)|} supplies the larger of the two values |LUMO(D)| and |LUMO(B)|.

It is more preferred here if

|LUMO(D)|−|LUMO(B)|<0.15 eV and

|LUMO(D)|−|LUMO(B)|>−0.2 eV, where it is very preferred if

|LUMO(D)|−|LUMO(B)|<0.1 eV and

|LUMO(D)|−|LUMO(B)|>−0.1 eV.

In connection with the above-mentioned, further embodiment of the present invention, it is furthermore very preferred if the following condition is satisfied:

max{|LUMO(D)|;|LUMO(B)|}−|LUMO(C)|>0.4 eV, where it is particularly preferred if max{|LUMO(D)|;|LUMO(B)|}−|LUMO(C)|>0.6 eV, In connection with the above-mentioned, further embodiment of the present invention, it is furthermore very particularly preferred if the following condition is satisfied:

$$|HOMO(C)|-|HOMO(B)|>0.4 \text{ eV},$$

where it is preferred if $$|HOMO(C)|-|HOMO(B)|>0.6 \text{ eV}.$$

Especial preference is given to a composition in accordance with the above-mentioned, further embodiment, which is characterised in that at least one of the two following conditions is satisfied:

$$\max\{|LUMO(D)|;|LUMO(B)|\}-|LUMO(C)|>0.4 \text{ eV}$$

or $$|HOMO(C)|-|HOMO(B)|>0.4 \text{ eV},$$

where it is more preferred if both conditions are satisfied, and where it is even more preferred if, in addition, one of the two following conditions is satisfied:

$$\max\{|LUMO(D)|;|LUMO(B)|\}-|LUMO(C)|>0.6 \text{ eV}$$

or $$|HOMO(C)|-|HOMO(B)|>0.6 \text{ eV},$$

and where it is most particularly preferred if both conditions are satisfied.

It is known to the person skilled in the art that a bipolar host is one which makes a significant contribution both to electron transport and also to hole transport in the mixture used in the component used. It is furthermore known to the person skilled in the art that this can be achieved if a material is selected (a) in which, owing to its energy level positions compared with the energy level positions of further materials used in the same mixture, both electrons and also holes are injected to a significant extent and (b) in which the transport is not suppressed owing to extremely low electron or hole mobility (less than $10^{-8}$ cm$^2$/(Vs)). The measurement of electron and hole mobilities is routinely carried out by the person skilled in the art by means of standard methods.

The person skilled in the art will be able to fall back on a large number of known hosts for the choice of suitable bipolar hosts and combine them with likewise known emitters having corresponding energy level positions.

Bipolar hosts are frequently represented by so-called hybrid systems. Hybrid systems are characterised in that they contain both at least one electron-transporting group and also at least one hole-transporting group, where these are generally groups which, due to their electron richness or their electron deficiency, achieve an HOMO which is suitable for hole injection or an LUMO which is suitable for electron injection.

Bipolarity is not a property of a single material, but instead is achieved through suitable properties relative to other materials present in the mixture. In the examples, it will later be shown that a material can be either a bipolar host or a neutral co-host depending on the other materials of the composition (compound 13t).

Preferred bipolar hosts are selected from the group of the pyridines, pyrimidines, triazines, benzimidazoles, carbazoles, indenocarbazoles, indolocarbazoles, 1,10-phenanthrolines, 1,3,4-oxadiazoles, phosphine oxides, phenylsulfonyls, ketones, lactams and triarylamines, where the triazines, pyrimidines, benzimidazoles, carbazoles, indenocarbazoles, indolocarbazoles, ketones, lactams and triarylamines are very preferred. Particularly preferred bipolar hosts here are selected from the group of the triazines, benzimidazoles, carbazoles, indenocarbazoles, lactams and triarylamines, where the triazines, carbazoles, indenocarbazoles and lactams are especially preferred.

Irrespective of the structural descriptions of the components of the composition, the relative positions of the limiting orbitals (HOMO, LUMO), as indicated above, are crucial for the advantageous technical effects. The components indicated here therefore have an illustrative character.

Pyridines which are suitable as bipolar hosts are disclosed, for example, in Adv. Mater., 2011, 23, 3876-3895. The pyridines disclosed therein also represent very preferred bipolar hosts in the sense of the present invention.

Pyrimidines which are suitable as bipolar hosts are disclosed, for example, in WO 2011/057706 A2, in WO2011/132684A1 or in EP 12008332.4. The pyrimidines disclosed therein also represent very preferred bipolar hosts in the sense of the present invention.

Triazines which are suitable as bipolar hosts are disclosed, for example, in WO 2011/057706 A2, EP 12008332.4 or in Adv. Mater., 2011, 23, 3876-3895. The triazines disclosed therein also represent very preferred bipolar hosts in the sense of the present invention.

Benzimidazoles which are suitable as bipolar hosts are disclosed, for example, in Adv. Mater., 2011, 23, 3876-3895 or in WO2010/107244 A2. The benzimidazoles disclosed therein also represent very preferred bipolar hosts in the sense of the present invention.

Carbazoles which are suitable as bipolar hosts are disclosed, for example, in WO 2011/057706 A2, EP 12008332.4 or in Adv. Mater., 2011, 23, 3876-3895. The carbazoles disclosed therein also represent very preferred bipolar hosts in the sense of the present invention.

Indenocarbazoles which are suitable as bipolar hosts are disclosed, for example, in EP 12008332.4 or in WO 2011/000455. The indenocarbazoles disclosed therein also represent very preferred bipolar hosts in the sense of the present invention.

Indolocarbazoles which are suitable as bipolar hosts are disclosed, for example, in WO 2008/056746 A1. The indolocarbazoles disclosed therein also represent very preferred bipolar hosts in the sense of the present invention.

1,10-Phenanthrolines which are suitable as bipolar hosts are disclosed, for example, in Adv. Mater., 2011, 23, 3876-3895. The 1,10-phenanthrolines disclosed therein also represent very preferred bipolar hosts in the sense of the present invention.

1,3,4-Oxadiazoles which are suitable as bipolar hosts are disclosed, for example, in Adv. Mater., 2011, 23, 3876-3895. The 1,3,4-oxadiazoles disclosed therein also represent very preferred bipolar hosts in the sense of the present invention.

Phosphine oxides which are suitable as bipolar hosts are disclosed, for example, in Adv. Mater., 2011, 23, 3876-3895. The phosphine oxides disclosed therein also represent very preferred bipolar hosts in the sense of the present invention.

Phenylsulfonyls which are suitable as bipolar hosts are disclosed, for example, in Adv. Mater., 2011, 23, 3876-3895. The phenylsulfonyls disclosed therein also represent very preferred bipolar hosts in the sense of the present invention.

Ketones which are suitable as bipolar hosts are disclosed, for example, in WO 2007/137725 A1 or in WO 2010/136109 A1. The ketones disclosed therein also represent very preferred bipolar hosts in the sense of the present invention.

Lactams which are suitable as bipolar hosts are disclosed, for example, in WO 2013/064206. The lactams disclosed therein also represent very preferred bipolar hosts in the sense of the present invention.

Triarylamines which are suitable as bipolar hosts are disclosed, for example, in WO2007/137725 A1, in WO 2011/000455 or in Adv. Mater., 2011, 23, 3876-3895. The triarylamines disclosed therein also represent very preferred bipolar hosts in the sense of the present invention.

As already mentioned above, bipolar hosts are frequently represented by so-called hybrid systems. Hybrid systems are characterised in that they contain both at least one electron-transporting group (ET) and also at least one hole-transporting group (HT).

The bipolar host of the composition according to the invention is therefore, in a further preferred embodiment of the present invention, a hybrid system containing both at least one electron-transporting group (ET) and also at least one hole-transporting group (HT). A review of such hybrid systems is given, for example, in Adv. Mater., 2011, 23, 3876-3895.

It is very preferred if the bipolar host is a hybrid system which is selected from the group consisting of the HT/N-containing heterocycle hybrid systems, HT/benzimidazole hybrid systems, HT/1,10-phenanthroline hybrid systems, HT/1,3,4-oxadiazole hybrid systems, HT/phosphine oxide hybrid systems, HT/phenylsulfonyl hybrid systems, HT/ketone hybrid systems and HT/lactam hybrid systems. The notation HT/benzimidazole is intended to mean that the bipolar host contains at least one hole-transporting group (HT) and at least one electron-transporting group, where one of the electron-transporting groups is a benzimidazole.

Preferred N-containing heterocycles are the pyridines, pyrimidines and triazines, where the triazines represent very preferred groups.

Particularly preferred hybrid systems for bipolar hosts are HT/pyridine hybrid systems, HT/pyrimidine hybrid systems, HT/triazine hybrid systems, HT/benzimidazole hybrid systems, very particularly preferred hybrid systems are HT/triazine hybrid systems or HT/benzimidazole hybrid systems and especially preferred hybrid systems are HT/triazine hybrid systems.

Furthermore preferred bipolar hosts are carbazole/ET hybrid systems, indenocarbazole/ET hybrid systems, indolocarbazole/ET hybrid systems, carbazole-carbazole/ET hybrid systems, indenocarbazole-carbazole/ET hybrid systems and amine/ET hybrid systems, where the carbazole/ET hybrid systems are very preferred.

Very particularly preferred hybrid systems here are the carbazole/triazine hybrid systems, indenocarbazole/triazine hybrid systems, indolocarbazole/triazine hybrid systems, carbazole-carbazole/triazine hybrid systems, indenocarbazole-carbazole/triazine hybrid systems and amine/triazine hybrid systems.

The neutral co-host of the composition according to the invention is, like the two other components (bipolar host and light-emitting dopant), determined by the relative positions of its limiting orbitals (HOMO/LUMO).

As already pointed out for the bipolar hosts, it should also be pointed out for the neutral co-hosts that neutrality is not a property of a single material, but instead is achieved through suitable properties relative to other materials present in the mixture (cf. compound 13t in the examples).

The person skilled in the art will be able to fall back on known hosts for the choice of suitable neutral co-hosts and combine them with likewise known emitters and hosts having corresponding energy level positions.

Examples of preferred neutral co-hosts are disclosed, for example, in WO 2010/108579, EP 12008584.0 and WO 2009/021126 A9.

The neutral co-hosts are preferably aromatic or heteroaromatic hydrocarbons, where the number of heteroaromatic rings in the neutral co-host is smaller than the number of aromatic rings. It is very preferred if the number of heteroaromatic rings in the neutral co-host is at most 2. It is particularly preferred if a maximum of one ring of the neutral co-host is a heteroaromatic ring.

A benzimidazole, for example, contains one aromatic ring (benzene) and one heteroaromatic ring (imidazole). A carbazole contains two aromatic rings (two benzenes) and one heteroaromatic ring (pyrrole). A spirobifluorene contains 4 aromatic rings (4 benzenes).

The neutral co-host preferably contains 6 or fewer, very preferably 5 or fewer, particularly preferably 4 or fewer, very particularly preferably 3 or fewer, especially preferably 2 or fewer, even more preferably 1 or fewer and most preferably no heteroatoms at all.

Depending on the energy levels of the emitter and bipolar host used, preferred neutral hosts may also be those which are used in combinations other than charge-transporting hosts, for example as electron-transporting hosts. These include, for example, lactams (for example WO 2013/064206), pyrimidines (for example WO 2010/136109 A1), triazines (for example WO 2010/136109 A1) and benzimidazoles (for example Optical Materials 35 (2013) 2201-2207).

Some illustrative, particularly preferred neutral co-hosts are those in the following overview.

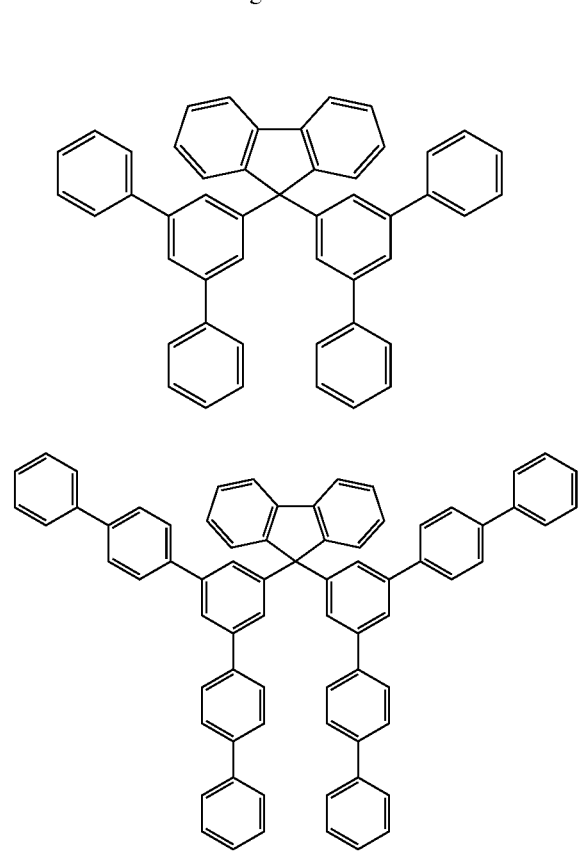

31
-continued
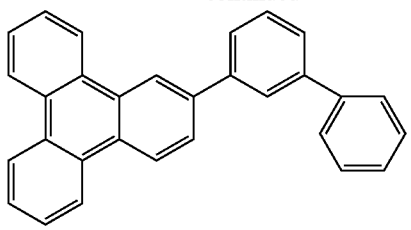
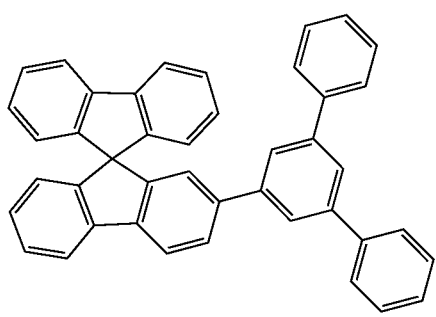
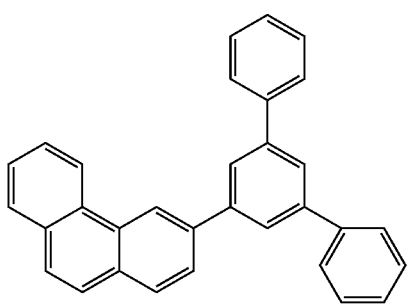
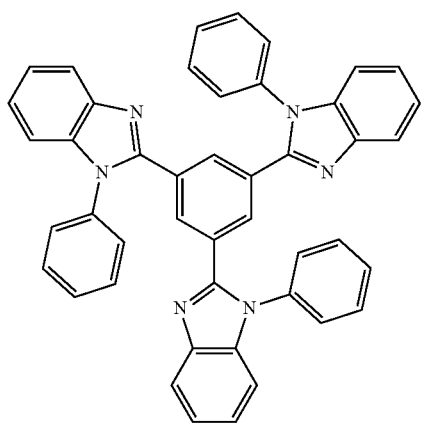
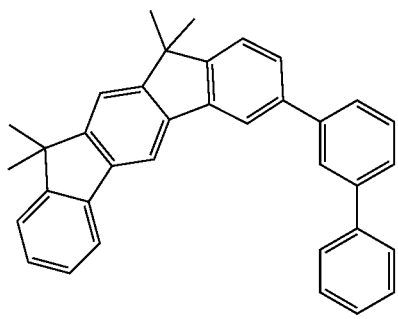
32
-continued
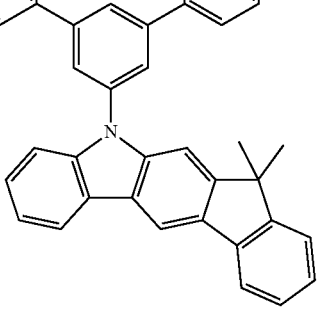
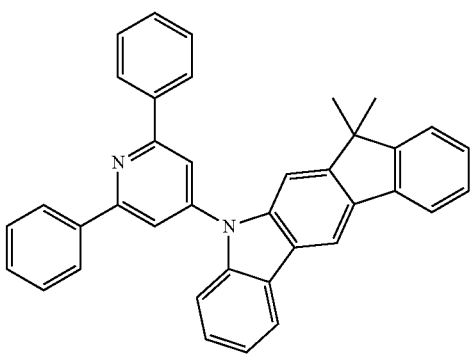
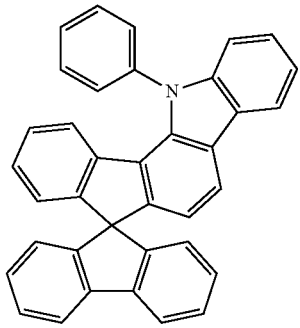
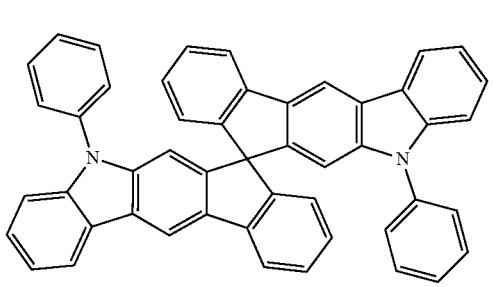

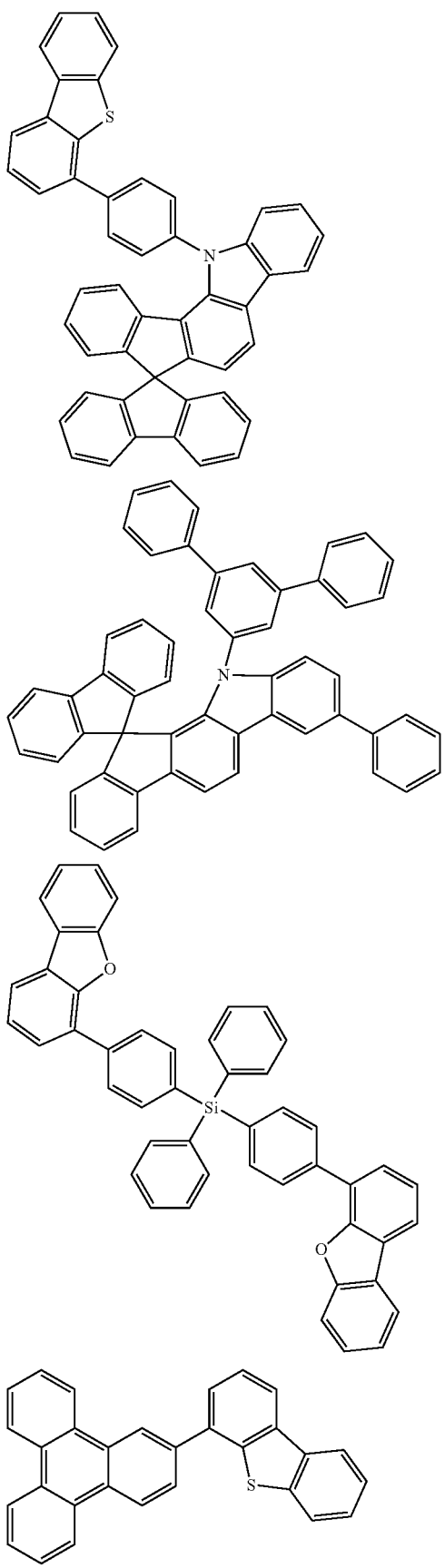
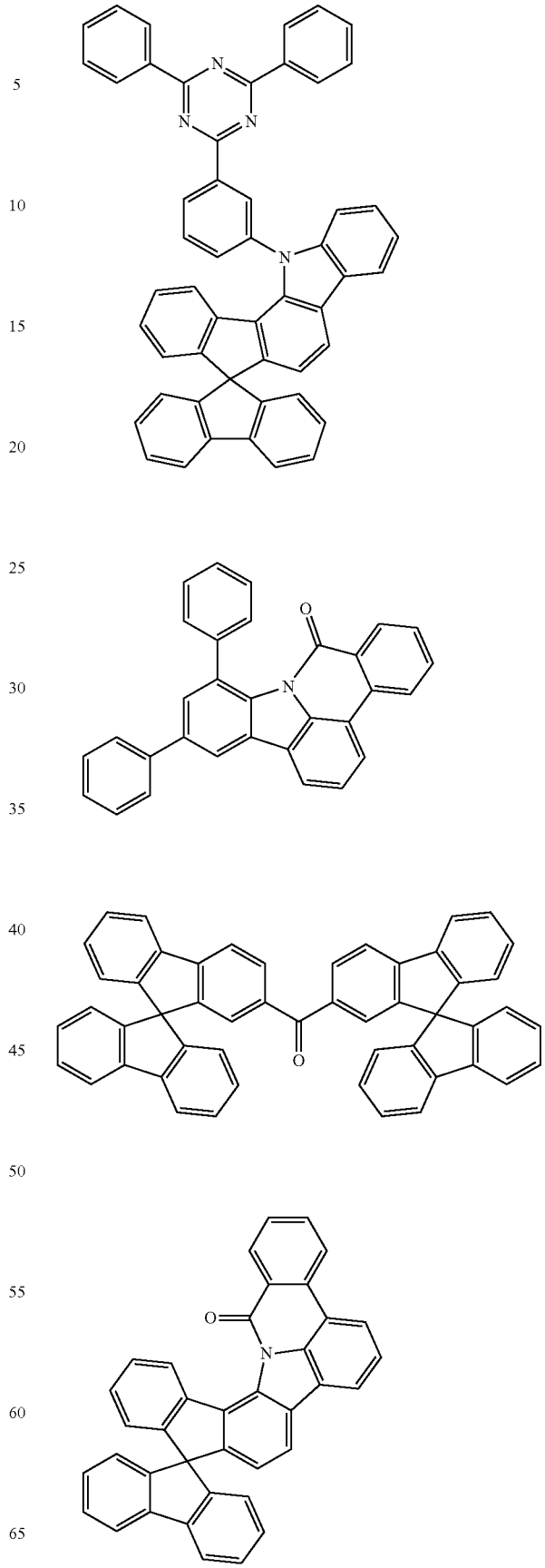

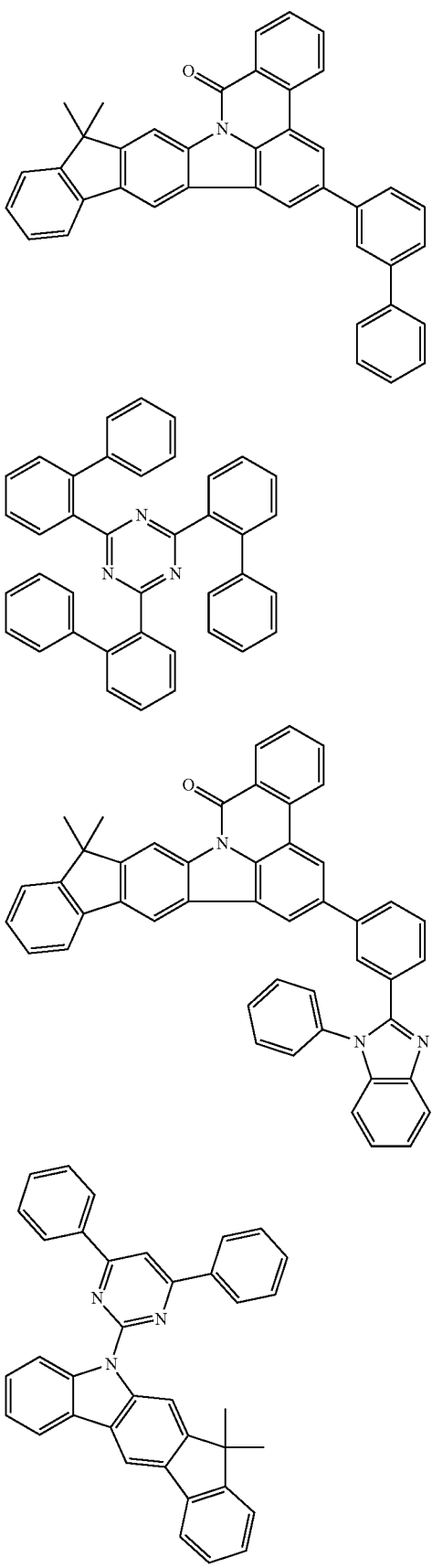

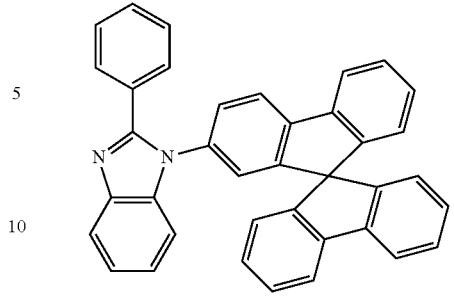

In a preferred embodiment, the composition according to the invention may comprise further organic functional materials besides the said materials, bipolar host, neutral co-host and light-emitting dopant. The present invention therefore also relates to a composition which, besides the three above-mentioned components, comprises further organic functional materials, which are preferably selected from the group of the hole-injection materials, hole-transport materials, hole-blocking materials, host materials, emitter materials, electron-blocking materials, electron-transport materials and electron-injection materials. The person skilled in the art is presented with absolutely no difficulties in making a choice here from a multiplicity of materials known to him.

It is very preferred if the composition comprises a further host material as further functional material.

In a preferred embodiment, the further host material is a further bipolar host material in the sense of this application. In a further preferred embodiment, the further host material is a further neutral host material in the sense of this application.

In a further preferred embodiment, the further host material is a hole-transporting host material. In a further preferred embodiment, the further host material is an electron-transporting host material.

Preferred further host materials are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar host materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 20081056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAlq.

The concentration of the further host material in the composition is preferably in the range from 10% by weight to 50% by weight, very preferably in the range from 10% by weight to 30% by weight and very particularly preferably in the range from 10% by weight to 20% by weight, based on the entire composition.

In a further preferred embodiment, the composition according to the invention comprises one or more further light-emitting dopants which are phosphorescent emitters.

It is particularly preferred if the composition comprises one or two further light-emitting dopants, where it is very particularly preferred if the composition comprises one further light-emitting dopant.

The phosphorescent dopants already mentioned above are suitable for this purpose.

In a preferred embodiment, a composition comprising two light-emitting, phosphorescent dopants is thus employed, where the phosphorescent dopant having the shorter-wave emission spectrum serves as co-host for the phosphorescent dopant having the longer-wave emission spectrum.

A dopant has a shorter-wave emission spectrum if its peak emission in the electroluminescence spectrum is shifted to a shorter wavelength compared with the peak emission in the electroluminescence spectrum of the other dopant.

Thus, for example, blue—(400-500 nm) or green—(501-560 nm) emitting, phosphorescent dopants can be employed as co-hosts for red-emitting, phosphorescent dopants. Likewise, for example, blue-emitting, phosphorescent dopants can be employed as co-hosts for green-emitting, phosphorescent dopants. This is advantageous for the lifetime, efficiency and operating voltage of the corresponding organic electroluminescent devices.

In a preferred embodiment, use is made here of compositions in which the predominant proportion of the emission in electroluminescence emanates from the longer-wave phosphorescent dopant.

The proportion of the emission in the electroluminescence of a dopant predominates if at least 70%, preferably at least 80% and very preferably at least 90% of the area under the electroluminescence emission spectrum is attributable to this dopant of the composition.

Very particular preference is given here to the use of compositions in which exclusively the longer-wave, phosphorescent dopant contributes to the emission in electroluminescence. The term "exclusively" herein means that at least 99% of the area under the electroluminescence emission spectrum is attributable to this dopant of the composition.

It is known to the person skilled in the art that the relative contribution of the two phosphorescent dopants to the electroluminescence can be influenced by a number of factors: a high proportion of emission from the longer-wave, phosphorescent dopant can be achieved, for example, through a high relative concentration of this emitter and/or low steric screening of the two emitters involved and/or suitable energy level positions which result in preferred exciton formation on the longer-wave, phosphorescent dopant.

In this embodiment, the concentration of the shorter-wave light-emitting, phosphorescent dopant in the composition is preferably in the range from 1% by weight to 40% by weight, very preferably in the range from 3% by weight to 30% by weight, and very particularly preferably in the range from 5% by weight to 20% by weight, based on the entire composition.

In addition, the concentration of the longer-wave light-emitting, phosphorescent dopant in the composition in this embodiment is preferably in the range from 1% by weight to 30% by weight, very preferably in the range from 5% by weight to 20% by weight, based on the entire composition.

In another preferred embodiment, use is made of a composition comprising two light-emitting, phosphorescent dopants in which both dopants make a significant contribution to the emission in electroluminescence.

A dopant makes a significant contribution to the emission in electroluminescence if its proportion of the emission in the electroluminescence is at least 10%, preferably at least 20% and very preferably at least 30% of the area under the electroluminescence emission spectrum of this dopant of the composition.

It is, for example, advantageous to generate green and red emission in one layer in this way. In combination with a further, blue-emitting layer, it is thus possible to generate white emission. Furthermore, it is, for example, advantageous to generate blue and yellow (561-585 nm) emission in one layer, so that overall white emission is also generated without the use of a further emission layer.

It is known to the person skilled in the art that the relative contribution of the two emitters to the electroluminescence can be influenced by a number of factors: a significant proportion of emission from the shorter-wave, phosphorescent dopant can be achieved, for example, through a low to very low relative concentration of the longer-wave, phosphorescent dopant and/or high steric screening of the two emitters involved and/or suitable energy level positions which result in preferred exciton formation on the shorter-wave, phosphorescent dopant.

In this embodiment, the concentration of the shorter-wave further light-emitting dopant in the composition is preferably in the range from 1% by weight to 40% by weight, very preferably in the range from 5% by weight to 30% by weight, and very particularly preferably in the range from 8% by weight to 20% by weight, based on the entire composition.

In addition, the concentration of the longer-wave light-emitting dopant in the composition in this embodiment is preferably in the range from 0.1% by weight to 10% by weight, very preferably in the range from 0.1% by weight to 3% by weight, based on the entire composition.

In a further preferred embodiment, use is made of a composition comprising in total three light-emitting, phosphorescent dopants in which all three dopants make a significant contribution to the emission in electroluminescence.

These dopants preferably have in total a plurality of emission maxima between 380 nm and 750 nm, resulting overall in white emission. Especial preference is given to a combination of blue, green and orange or red emission.

It is known to the person skilled in the art that the relative contribution of the three emitters to the electroluminescence can be influenced by the same factors which have already been described above for the case of two emitters.

In this embodiment, the concentration of the shortest-wave light-emitting dopant in the composition is preferably in the range from 1% by weight to 40% by weight, very preferably in the range from 5% by weight to 30% by weight, and very particularly preferably in the range from 8% by weight to 20% by weight, based on the entire composition.

In addition, the concentration of the light-emitting dopant having the next-highest emission wavelength in the composition in this embodiment is preferably in the range from 0.1% by weight to 10% by weight, very preferably in the range from 0.5% by weight to 3% by weight, based on the entire composition.

In addition, the concentration of the longest-wave light-emitting dopant in the composition in this embodiment is preferably in the range from 0.01% by weight to 5% by weight, very preferably in the range from 0.1% by weight to 1% by weight, based on the entire composition.

In a particularly preferred embodiment of the present invention, the composition comprises no organic functional materials besides the bipolar host, the neutral co-host and the light-emitting dopant, where it is very particularly preferred if the composition according to the invention consists only of the bipolar host, the neutral co-host and the light-emitting dopant and comprises no further organic or inorganic constituents.

In a further particularly preferred embodiment of the present invention, the composition comprises none of the above-mentioned organic functional materials besides the bipolar host, the neutral co-host, the light-emitting dopant and the further host material, where it is very particularly preferred if the composition according to the invention consists only of the bipolar host, the neutral co-host, the light-emitting dopant and the further host material and comprises no further organic or inorganic constituents.

In still a further particularly preferred embodiment of the present invention, the composition comprises none of the above-mentioned organic functional materials besides the bipolar host, the neutral co-host, the light-emitting dopant and the further light-emitting dopant, where it is very particularly preferred if the composition according to the invention consists only of the bipolar host, the neutral co-host, the light-emitting dopant and the further light-emitting dopant and comprises no further organic or inorganic constituents.

The compositions according to the invention can be used in electronic devices, in particular in organic electroluminescent devices. The components of the compositions can be processed here by vapour deposition or from solution. If the compositions are applied from solution, at least one further solvent is necessary. Processing from solution has the advantage that the layer comprising the composition according to the invention can be applied very simply and inexpensively. This technique is particularly suitable for the mass production of organic electronic devices.

The present invention therefore also relates to a formulation comprising a composition according to the invention and at least one solvent.

Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The said formulation can, as already explained, be used to process a layer of an electronic device from solution. The present invention therefore relates to the use of a formulation according to the invention for the production of an electronic device, in particular an organic electroluminescent device, characterised in that the formulation is used in order to process an emission layer of the device from solution.

The present invention also relates to the use of the compositions according to the invention in an organic electronic device.

The present invention therefore also relates to an organic electronic device comprising at least one composition according to the invention, where the device is preferably selected from organic integrated circuits (OICs), organic field-effect transistors (OFETs), organic thin-film transistors (OTFTs), organic electroluminescent devices, organic solar cells (OSCs), organic optical detectors and organic photoreceptors, where organic electroluminescent devices are very preferred.

Very particularly preferred organic electroluminescent devices in the sense of the present invention are organic light-emitting transistors (OLETs), organic field-quench devices (OFQDs), organic light-emitting electrochemical cells (OLECs, LECs, LEECs), organic laser diodes (O-lasers) and organic light-emitting diodes (OLEDs), especially preferably OLECs and OLEDs and most preferably OLEDs.

Apart from cathode, anode and the layer comprising the composition according to the invention, the organic electroluminescent device may also comprise further layers. These are selected, for example, from in each case one or more hole-injection layers, hole-transport layers, hole-blocking layers, emitting layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present.

The sequence of the layers of organic electroluminescent devices is preferably the following:
anode/hole-injection layer/hole-transport layer/emitting layer/electron-transport layer/electron-injection layer/cathode.

It should again be pointed out here that not all of the said layers have to be present, and/or that further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Especial preference is given to three-layer systems, i.e. systems having three emitting layers, where the three layers exhibit blue, green and orange or red emission (for the basic structure see, for example, WO 2005/011013). It should be noted that, for the generation of white light, an emitter compound used individually which emits in a broad wavelength range may also be suitable instead of a plurality of emitter compounds emitting in colour.

The composition according to the invention is also suitable, in particular, for use in organic electroluminescent devices, as described, for example, in WO 98/24271, US 2011/0248247 and US 2012/0223633. In these multi-coloured display components, an additional blue emission layer is applied by vapour deposition over the entire area to all pixels, including those having a colour other than blue. Surprisingly, it is found here that the compositions according to the invention, if employed for the red and/or green pixels, together with the vapour-deposited blue emission layer result in furthermore very good emission.

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

The hole-transport materials are especially preferably materials which can be used in a hole-transport, hole-injection or electron-blocking layer, indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or the as yet unpublished EP 12000929.5), fluorenamines (for example in accordance with the as yet unpublished applications EP 12005369.9, EP 12005370.7 and EP 12005371.5), spirodibenzopyranamines (for example in accordance with the as yet unpublished application EP 11009127.9) and dihydroacridine derivatives (for example in accordance with the as yet unpublished EP 11007067.9).

The cathode of the electronic device preferably comprises metals having a low work function, metal alloys or multi-layered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers. Furthermore, the anode may also consist of a plurality of layers, for example of an inner layer of ITO and an outer layer of a metal oxide, preferably tungsten oxide, molybdenum oxide or vanadium oxide.

During production, the electronic device is appropriately (depending on the application) structured, provided with contacts and finally sealed, since the lifetime of the devices according to the invention is shortened in the presence of water and/or air.

In a preferred embodiment, the electronic device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds are necessary for this purpose. High solubility can be achieved through suitable substitution of the compounds.

For the production of an organic electroluminescent device according to the invention, it is furthermore preferred to apply one or more layers from solution and one or more layers by a sublimation process.

The invention thus furthermore relates to a process for the production of the electronic device according to the invention, characterised in that at least one organic layer is applied by gas-phase deposition or from solution.

The devices according to the invention can be employed in a very versatile manner. Thus, the electroluminescent devices can be employed, for example, in displays for televisions, mobile telephones, computers and cameras. However, the devices can also be used in lighting applications. Furthermore, electroluminescent devices, for example in OLEDs or OLECs, comprising at least one composition according to the invention can be used in medicine or cosmetics for phototherapy. Thus, a large number of diseases (psoriasis, atopic dermatitis, inflammation, acne, skin cancer, etc.) can be treated or skin wrinkling, skin reddening and skin ageing can be prevented or reduced. Furthermore, the light-emitting devices can be utilised in order to keep drinks, meals or foods fresh or in order to sterilise equipment (for example medical equipment).

The present invention also relates to a device comprising at least one organic electronic device according to the invention, preferably an organic electroluminescent device, where the device is preferably a television, a mobile telephone or smartphone, a computer (for example desktop computer, tablet, notebook) or a photographic camera.

The present invention furthermore relates to an organic electroluminescent device, preferably an OLED or OLEC and very particularly preferably an OLED, comprising a composition according to the invention for use in medicine for phototherapy.

The present invention furthermore preferably relates to an electronic device, preferably an organic electroluminescent device according to the invention, very preferably an OLED or OLEC and very particularly preferably an OLED, for use for the phototherapeutic treatment of skin diseases.

The present invention furthermore very preferably relates to an electronic device according to the invention, preferably an organic electroluminescent device according to the invention, very preferably an OLED or OLEC and very particularly preferably an OLED, for use for the phototherapeutic treatment of psoriasis, atopic dermatitis, inflammatory diseases, vitiligo, wound healing and skin cancer.

Finally, the present invention also relates to the use of the organic electroluminescent devices according to the invention, very preferably an OLED or OLEC and very particularly preferably an OLED, in the cosmetics area, preferably for the treatment of acne, skin ageing and of cellulite.

The composition according to the invention is preferably employed in the emission layer of the organic electroluminescent device.

As already explained above, organic electroluminescent devices often comprise further layers besides an anode, cathode and an emission layer. These further layers may comprise organic and/or inorganic constituents.

In this connection, it is particularly advantageous if a hole-transport layer (HTL) which is directly adjacent to the emission layer is present between the emission layer and the anode. In principle, all hole-transport materials (HTMs) which are familiar to the person skilled in the art can be employed for this purpose. Hole-transport materials which are typically employed for this purpose and which also represent preferred hole-transport materials in the sense of the present invention are selected from the group of the triarylamines, carbazoles, indenocarbazoles, indolocarbazoles and aromatic silylamines.

It has been found that particularly good results can be achieved if the injection barrier for holes from the hole-transport layer into the emission layer is low. This is the case if the following condition is satisfied, where $|HOMO(B)|$ and $|HOMO(HTM)|$ stand for the moduli of the HOMO energies of the bipolar host in the emission layer and for those of the hole-transport material in the adjacent HTL:

$$|HOMO(B)| - |HOMO(HTM)| < 0.3 \text{ eV},$$

It has furthermore proven advantageous if an electron-transport layer (ETL) which is directly adjacent to the emission layer is present between the emission layer and the cathode. In principle, all electron-transport materials (ETMs) which are familiar to the person skilled in the art can be employed for this purpose. Electron-transport materials which are typically employed for this purpose and which also represent preferred electron-transport materials in the sense of the present invention are selected from the group of the pyridines, pyrimidines, triazines, benzimidazoles, metal hydroxy-quinolinates, oxadiazoles, triazoles and ketones.

It has been found that particularly good results can be achieved if the following condition is satisfied, where $|LUMO(B)|$ and $|LUMO(ETM)|$ stand for the moduli of the LUMO energies of the bipolar host in the emission layer and for those of the electron-transport material in the adjacent ETL:

$$|LUMO(B)| - |LUMO(ETM)| < 0.3 \text{ eV}.$$

The compositions according to the invention and the devices according to the invention are distinguished by the following surprising advantages over the prior art:

1. The compositions according to the invention are very highly suitable for use in an emission layer and exhibit improved performance data, in particular efficiency, compared with compounds from the prior art.
2. The use of the compositions according to the invention in electronic devices results in significant increases in the lifetimes of the devices,
3. The compositions can be processed easily and are therefore very highly suitable for mass production in commercial application.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, are themselves inventive and should not merely be regarded as part of the embodiments of the present invention. For these features, independent protection may be sought in addition or as an alternative to each invention claimed at present.

The teaching on technical action disclosed with the present invention can be abstracted and combined with other examples.

The invention is illustrated in greater detail by the following examples, without wishing to restrict it thereby.

EXAMPLES

Example 1a

Synthesis of 3-(2-chloro-4-phenyl-1,3,5-triazin-6-yl)-5'-phenyl-[1,1':3',1"]terphenyl

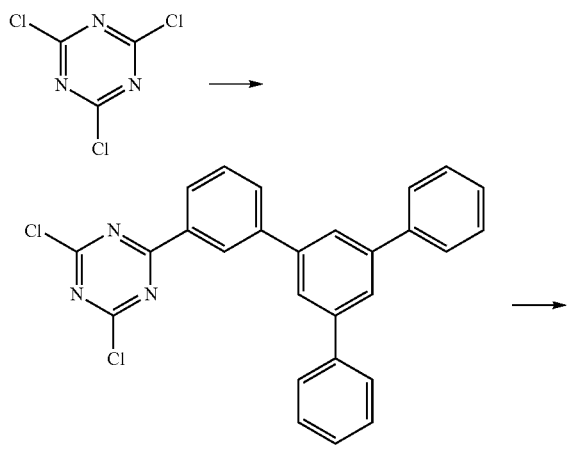

Step 1:

9.9 g (407 mmol) of magnesium are activated using a grain of iodine. About 30 ml of a solution of 141.8 g (368 mmol) of 3-bromo-5'-phenyl-[1,1':3',1"]terphenyl [12233200-57-1] in 700 ml of THF are added, and a heating bath at 90° C. is placed underneath. When the reaction commences and reflux has been achieved, the remaining solution is added dropwise at such a rate that the reflux is maintained. When the addition is complete, the reaction mixture is heated under reflux for a further 2 hours.

Step 2:

67.9 g (368 mmol) of 2,4,6-trichloro-1,3,5-triazine [108-77-0] are initially introduced in 400 ml of THF and cooled to −5° C. The Grignard solution prepared in step 1 is added dropwise at such a rate that the internal temperature does not exceed 0° C. The cooling is removed, and the mixture is stirred for 16 hours; the mixture is subsequently re-cooled to −5° C., and 184 ml (368 mmol) of phenylmagnesium chloride solution (2 M in THF) are added dropwise at such a rate that the internal temperature does not exceed 0° C. The cooling is removed, and the mixture is stirred for 18 hours. 400 ml of 1 M hydrochloric acid are slowly stirred in. After one hour, the solid formed is filtered off with suction and dried in vacuo. Recrystallisation from toluene twice leaves 56.7 g (114 mmol, 31% of theory) of the product as a pale-brown solid having a purity of about 98% according to ¹H-NMR.

The following compound can be prepared analogously:

| Ex. | Starting material step 1 | Product | Yield |
|---|---|---|---|
| 1b | 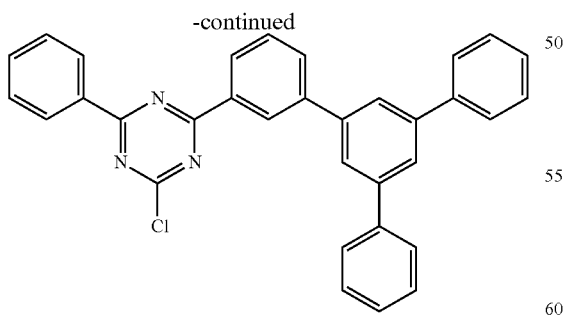 [103068-20-8] | | 37% |

-continued

Example 2a

Synthesis of (2-chlorophenyl)(spiro-9,9'-bifluoren-4-yl)amine

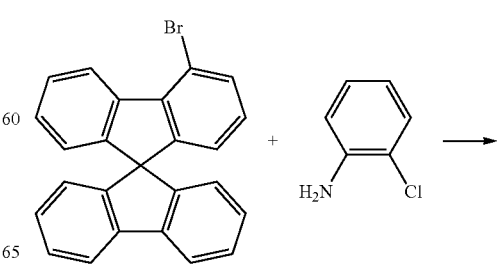

-continued

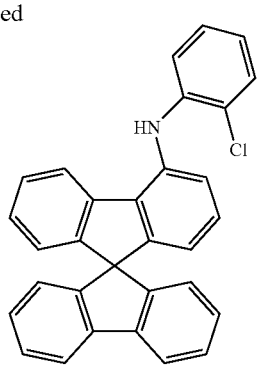

54.1 g (137 mmol) of 4-bromospiro-9,9'-bifluorene [1161009-88-6], 17.9 g (140 mmol) of 2-chloroaniline [95-51-2], 68.2 g (710 mmol) of sodium tertbutoxide, 613 mg (2.7 mmol) of palladium(II) acetate and 3.03 g (5.5 mmol) of 1,1'-bis(diphenylphosphino)ferrocene are initially introduced in 1300 ml of toluene and heated under reflux for 5 hours. After cooling to room temperature, the reaction mixture is extended with 700 ml of toluene and filtered through Celite. The solvent is removed in a rotary evaporator, and the residue is recrystallised from a toluene/heptane mixture (1:2). Drying in vacuo leaves 52.2 g (118 mmol, 86% of theory) of the product as a pale-yellow solid.

Example 3a

Synthesis of spiro[9H-fluoren-9,7'(1'H)-indeno[1,2-a]carbazole]

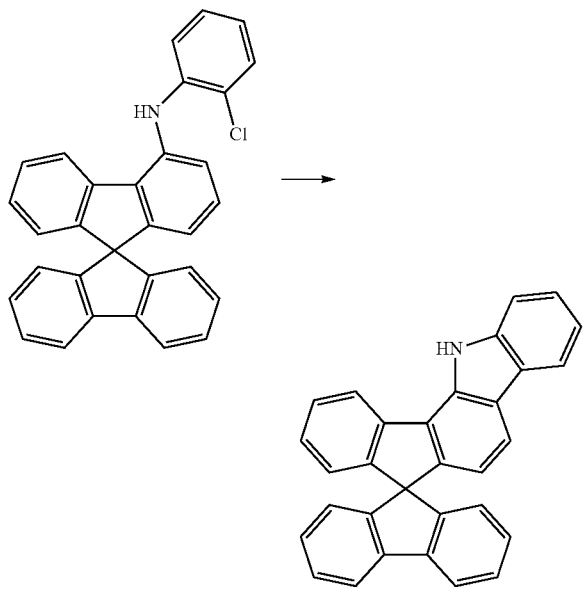

45.0 g (102 mmol) of (2-chlorophenyl)(spiro-9,9'-bifluoren-4-yl)amine (Ex. 2a), 56.0 g (405 mmol) of potassium carbonate, 4.5 g (12 mmol) of tricyclohexylphosphonium tetrafluoroborate and 1.38 g (6 mmol) of palladium(II) acetate are suspended in 500 ml of dimethylacetamide and heated under reflux for 6 hours. After cooling to room temperature, the reaction mixture is extended with 600 ml of dichloromethane and 300 ml of water and stirred for 30 minutes. The organic phase is separated off and freed from solvent in a rotary evaporator. The residue is extracted with about 250 ml of hot toluene over a bed of aluminium oxide (basic, activity grade 1) and finally recrystallised once from toluene, leaving 32.5 g (80 mmol, 78% of theory) of the product as a beige solid having a purity of about 98% according to $^1$H-NMR.

Example 4a

Synthesis of 10-(3-bromophenyl)-12,12-dimethyl-10,12-dihydro-10-azaindeno[2,1-b]fluorene

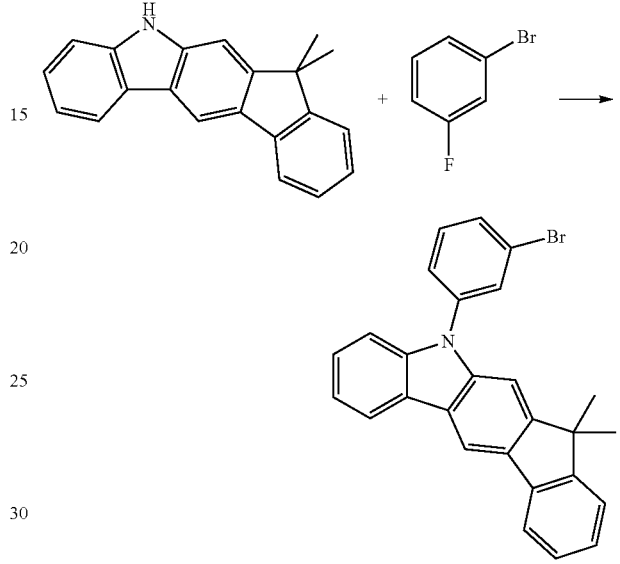

150.0 g (526 mmol) of 12,12-dimethyl-10,12-dihydro-10-azaindeno[2,1-b]-fluorene [1257220-47-5], 184.0 g (1.05 mmol) of 1-bromo-3-fluorobenzene [1073-06-9] and 334.7 g (1.58 mol) of potassium phosphate are initially introduced in 2 l of dimethylacetamide and heated under reflux for 14 hours. After cooling to room temperature, the solvent is removed as far as possible in a rotary evaporator, leaving a dark-brown oil. After vigorous rubbing of the flask wall with a glass rod, the product can be precipitated by slowly stirring in about 750 ml of ethanol. The solid formed is filtered off with suction, washed four times with 250 ml of ethanol each time, dried in vacuo and finally subjected to fractional sublimation at a pressure of about $10^{-5}$ mbar and 220° C., leaving 152.2 g (347 mmol, 66% of theory) of the product as a yellow glass-like solid having a purity of about 99% according to $^1$H-NMR.

Example 5a

Synthesis of 7-bromo-12,12-dimethyl-10,12-dihydro-10-azaindeno[2,1-b]fluorene

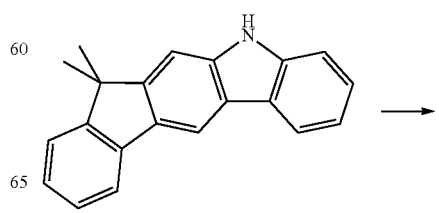

-continued

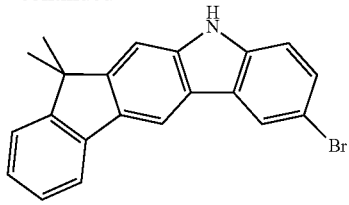

56.7 g (200 mmol) of 12,12-dimethyl-10,12-dihydro-10-azaindeno[2,1-b]-fluorene [1257220-47-5] are initially introduced in 1500 ml of THF. The reaction mixture is cooled to 0° C., and 35.6 g (200 mmol) of N-bromosuccinimide are added in portions over the course of 30 minutes. The cooling is removed, and the mixture is stirred for 16 hours and subsequently evaporated to about 250 ml. 1000 ml of water are added with vigorous stirring, and the solid formed is filtered off with suction and washed by boiling twice with 800 ml of ethanol each time. Drying in vacuo leaves 47.1 g (130 mmol, 65% of theory) of the product as a colourless solid having a purity of about 98% according to $^1$H-NMR.

The following compounds can be prepared analogously:

| Ex. | Starting material | Product | Yield |
|---|---|---|---|
| 5b | 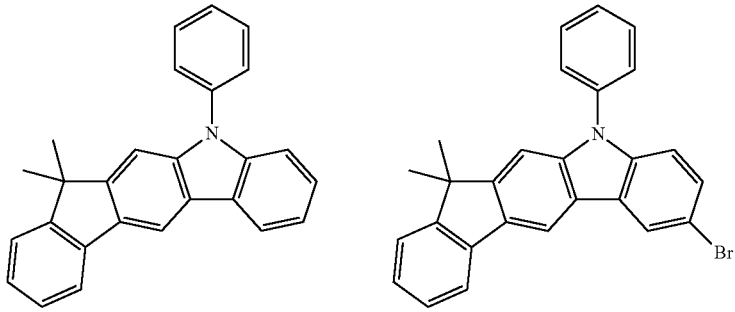 | | 81% |
| | Ex. 8g | | |
| 5c | 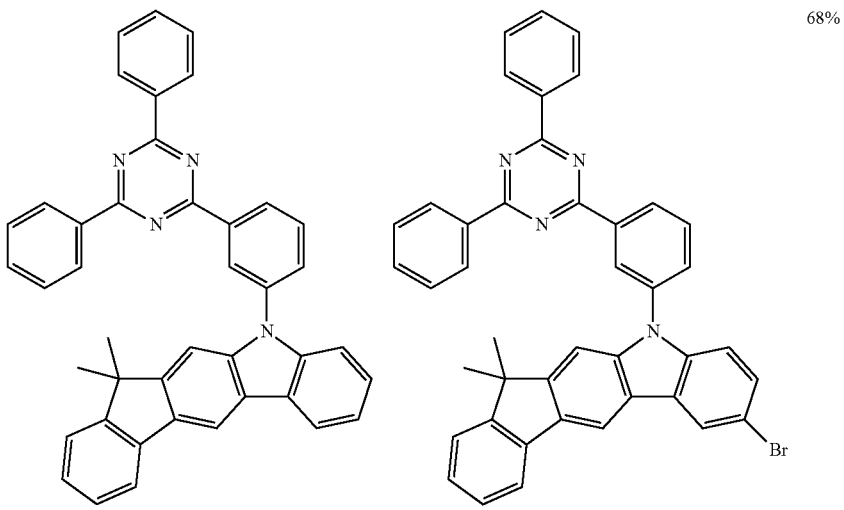 | | 68% |
| | Ex. 8h | | |

| Ex. | Starting material | Product | Yield |
|---|---|---|---|
| 5d | | | 62% |
| | Ex. 10b | | |
| 5e | | | 44% |
| | Ex. 8c | | |
Example 6a
Synthesis of 12,12-dimethyl-10-phenyl-7-(4,4,5,5-tetramethyl-1,3,2-dioxaborolan-2-yl)-10,12-dihydro-10-azaindeno[2,1-b]fluorene
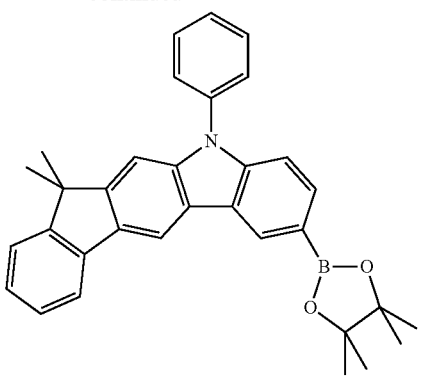
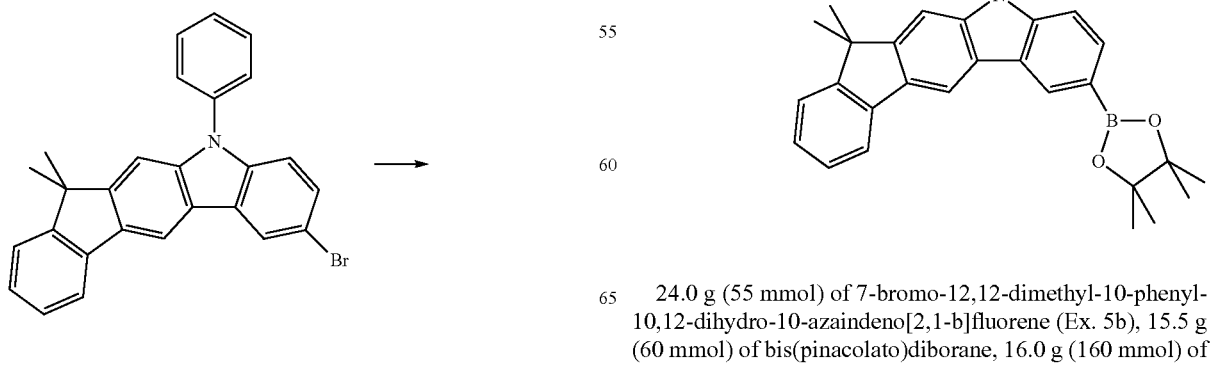
24.0 g (55 mmol) of 7-bromo-12,12-dimethyl-10-phenyl-10,12-dihydro-10-azaindeno[2,1-b]fluorene (Ex. 5b), 15.5 g (60 mmol) of bis(pinacolato)diborane, 16.0 g (160 mmol) of potassium acetate and 1.3 g (1.7 mmol) of 1,1'-bis(diphenylphosphino)ferrocenepalladium(II) dichloride/dichloromethane adduct in 350 ml of dioxane are heated under reflux for 18 hours. After cooling to room temperature, the solvent is removed in a rotary evaporator, 500 ml of dichloromethane and 800 ml of water are added to the residue, and the mixture is stirred for 30 minutes. The organic phase is separated off, washed twice with 250 ml of water each time, dried over sodium sulfate and evaporated to about 100 ml. 1000 ml of heptane are stirred in, and the solid formed is filtered off with suction. Drying in vacuo leaves 23.9 g (49 mmol, 89% of theory) of the product as a beige solid having a purity of about 97% according to $^1$H-NMR.

Example 7a

Synthesis of 3-[2-(spirofluoren-9,7'-indeno[1,2-a]carbazol-12'-yl)-4-phenyl-1,3,5-triazin-6-yl]-5'-phenyl-[1,1':3',1"]terphenyl

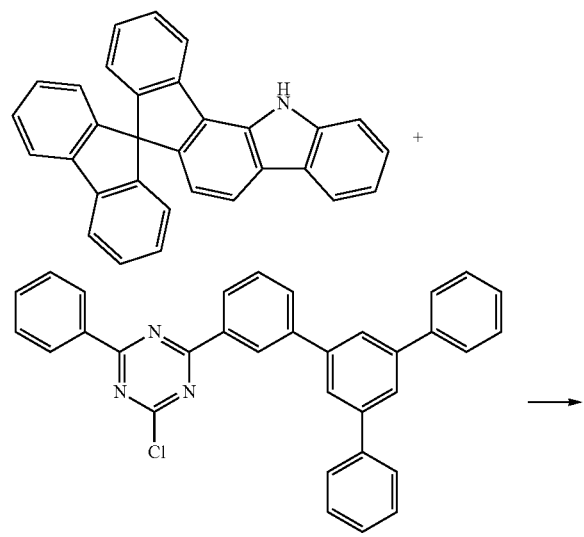

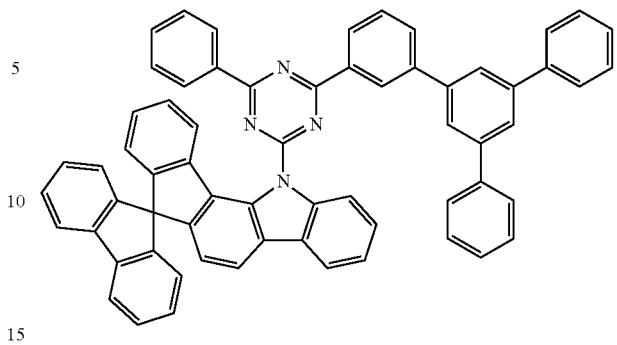

A solution of 45.0 g (111 mmol) of spiro[9H-fluoren-9,7'(1'H)-indeno[1,2-a]-carbazole] (Ex. 3a) in 800 ml of dimethylformamide is added dropwise with vigorous stirring to a solution of 5.3 g of sodium hydride (60% in mineral oil, 133 mmol) in 600 ml of dimethylformamide, and the mixture is stirred for two hours. A suspension of 55.0 g (111 mmol) of 3-(2-chloro-4-phenyl-1,3,5-triazin-6-yl)-5'-phenyl-[1,1':3',1']terphenyl (Ex. 1a) in 550 ml of dimethylformamide is slowly added, and the mixture is stirred for 18 hours. 500 ml of water are stirred in; the mixture is stirred for a further hour. The solid formed is filtered off with suction, washed three times with 250 ml of ethanol each time and subsequently extracted with about 200 ml of hot methyl ethyl ketone over aluminium oxide (basic, activity grade 1). After cooling to room temperature, the mixture is stirred for a further 5 hours; the solid formed is filtered off with suction and washed twice by stirring with 150 ml of hot methyl ethyl ketone each time, where in each case stirring is continued for 16-18 hours at room temperature. The solid is filtered off with suction, dried in vacuo and finally subjected to fractional sublimation at about $10^{-5}$ mbar and 370° C., leaving 16.4 g (19 mmol, 17% of theory) of the product as a yellow glass-like solid having a purity of 99.9% according to HPLC.

The following compounds can be prepared analogously:

| Ex. | Starting material 1 | Starting material 2 | Product | Yield |
|---|---|---|---|---|
| 7b | Ex. 5a | [3842-55-5] | | 53% without sublimation |

-continued

| Ex. | Starting material 1 | Starting material 2 | Product | Yield |
|---|---|---|---|---|
| 7c | 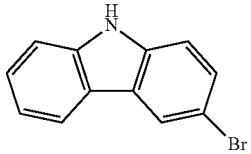 [1592-95-6] | 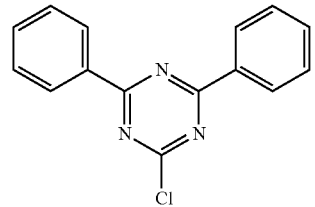 [3842-55-5] | 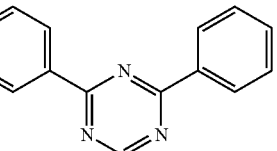 | 60% without sublimation |

Example 8a

Synthesis of N-phenylspiro[9H-fluoren-9,7'(1'H)-indeno[1,2-a]-carbazole]

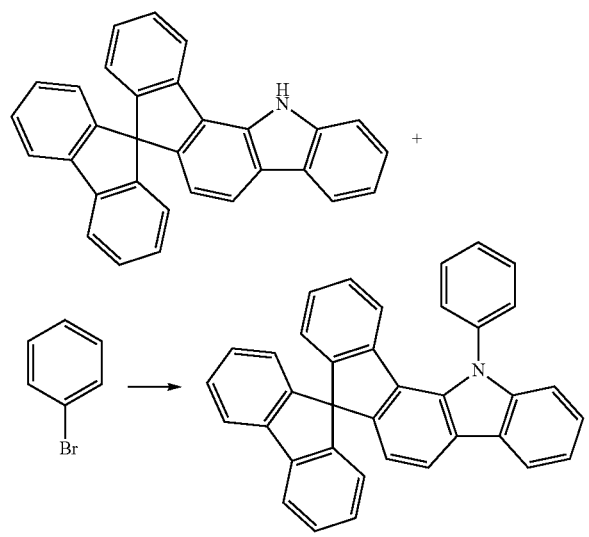

43.0 g (106 mmol) of spiro[9H-fluoren-9,7'(1'H)-indeno[1,2-a]carbazole] (Ex. 3a), 17.9 g (114 mmol) of bromobenzene, 30.5 g (317 mmol) of sodium Pert-butoxide, 0.5 g (2.2 mmol) of palladium(II) acetate and 4.2 ml of tri-tert-butylphosphine solution (1 M in toluene) are initially introduced in 1500 ml of p-xylene and heated under reflux for 16 hours. After cooling to room temperature, the organic phase is separated off from solid constituents, washed three times with 200 ml of water each time and subsequently freed solvent in a rotary evaporator. The residue is extracted with about 300 ml of hot toluene over aluminium oxide (basic, activity grade 1), recrystallised twice from toluene and finally subjected to fractional sublimation at about $10^{-5}$ mbar and 270° C., leaving 22.0 g (46 mmol, 43% of theory) of the product as a pale-yellow solid having a purity of 99.9% according to HPLC.

The following compounds can be prepared analogously:

| Ex. | Starting material 1 | Starting material 2 | Product | Yield |
|---|---|---|---|---|
| 8c | 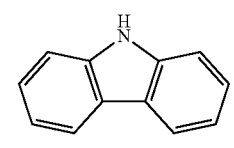 [86-74-8] | 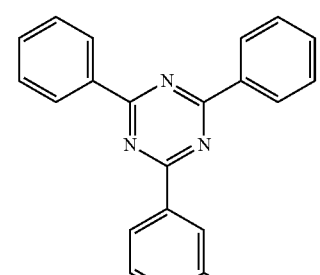 [864377-31-1] | 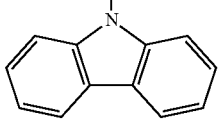 | 66% without sublimation |

-continued
| Ex. | Starting material 1 | Starting material 2 | Product | Yield |
|---|---|---|---|---|
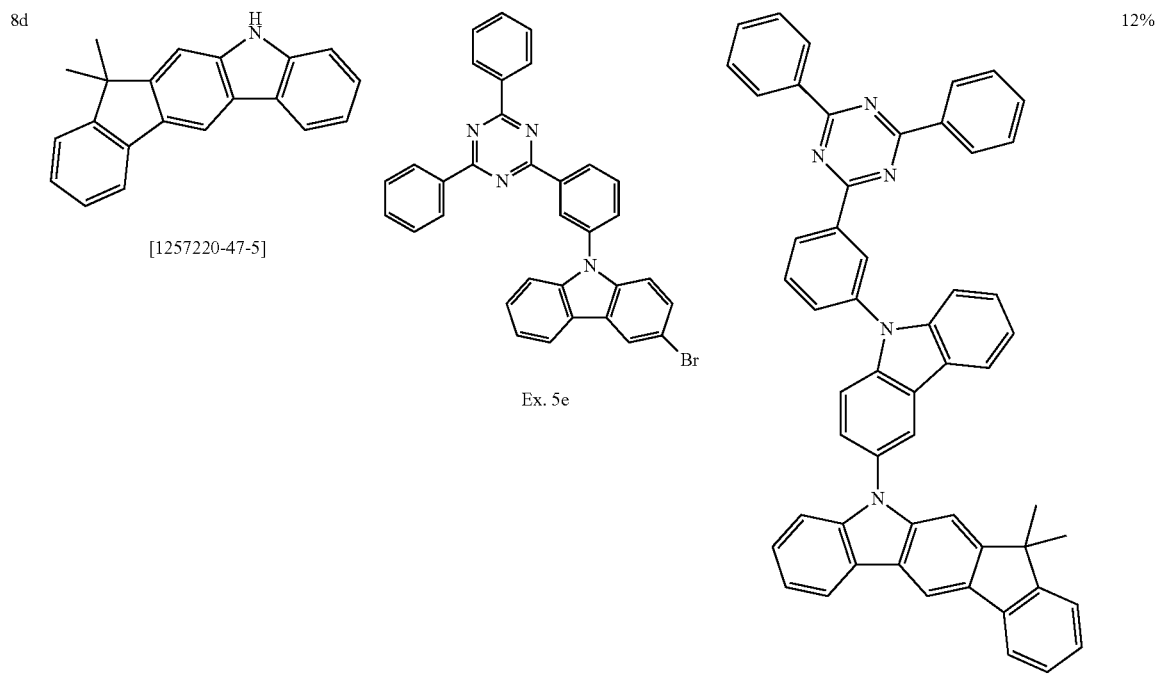
8d [1257220-47-5] / Ex. 5e / 12%
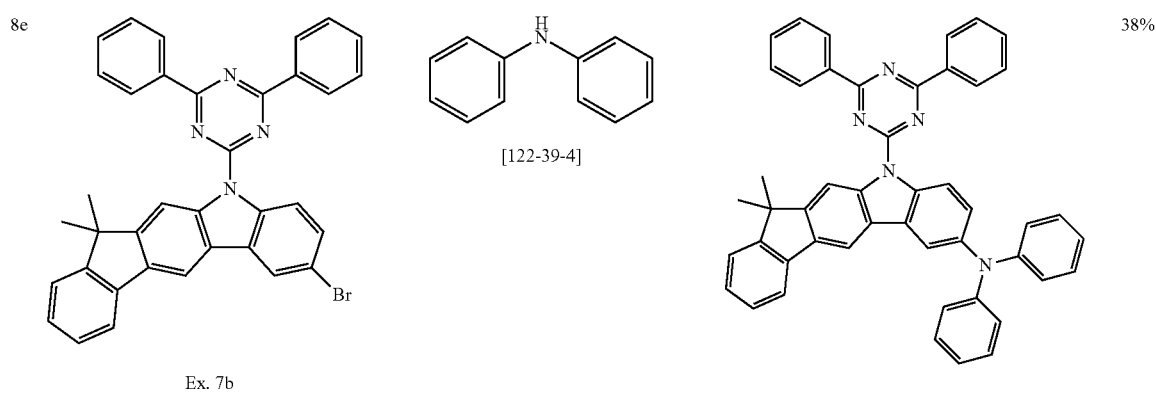
8e Ex. 7b / [122-39-4] / 38%

-continued

| Ex. | Starting material 1 | Starting material 2 | Product | Yield |
|---|---|---|---|---|
| 8f | Ex. 7c | [122-39-4] | | 30% |
| 8g | [1257220-47-5] | [108-86-1] | | 83% without sublimation |
| 8h | [1257220-47-5] | [864377-31-1] | | 58% without sublimation |

| Ex. | Starting material 1 | Starting material 2 | Product | Yield |
|---|---|---|---|---|
| 8i | 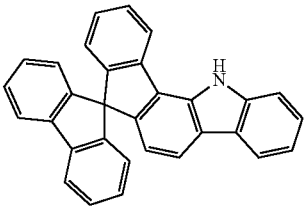 Ex. 3a | 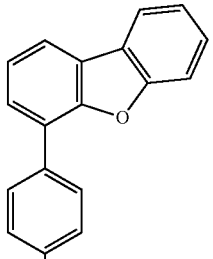 [955959-84-9] | 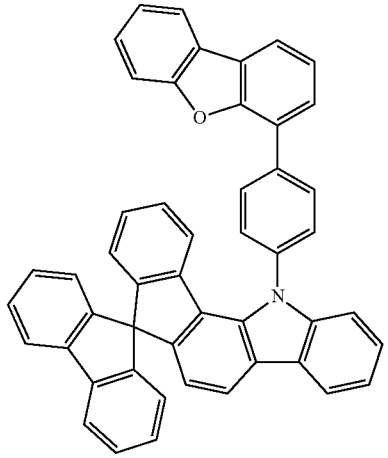 | 54% |

Example 9a

Synthesis of 7-{9-[3-(4,6-diphenyl-1,3,5-triazin-2-yl)phenyl]-9H-carbazol-3-yl}-12,12-dimethyl-10-phenyl-10,12-dihydro-10-azaindeno[2,1-b]fluorene

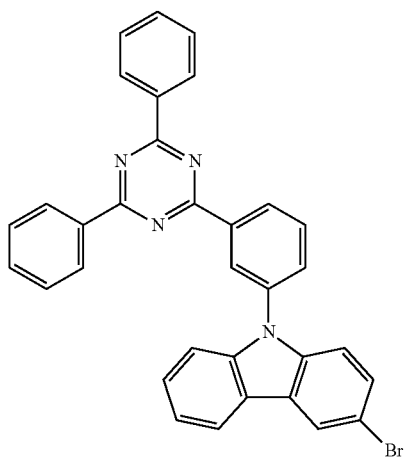 [SMILES: Brc1ccc2c(c1)c1ccccc1n2-c1cccc(-c2nc(-c3ccccc3)nc(-c3ccccc3)n2)c1]

+

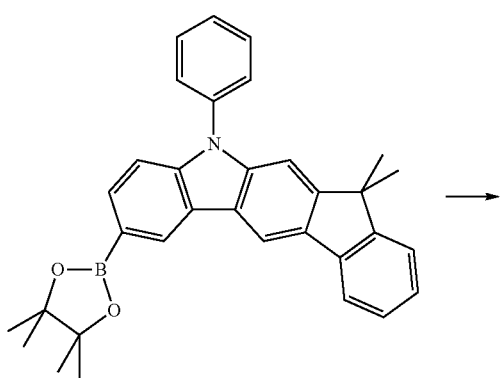

→

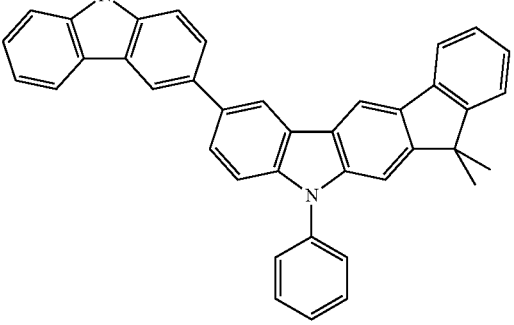

25.0 g (36 mmol) of 3-bromo-9-[3-(4,6-diphenyl-1,3,5-triazin-2-yl)phenyl]-9H-carbazole (Ex. 5e), 22.8 g (47 mmol) of 12,12-dimethyl-10-phenyl-7-(4,4,5,5-tetramethyl-1,3,2-dioxaborolan-2-yl)-10,12-dihydro-10-azaindeno[2,1-b]fluorene (Ex. 6a) and 4.2 g (40 mmol) of sodium carbonate are initially introduced in a mixture of 500 ml of toluene, 500 ml of dioxane and 180 ml of water. The mixture is flushed through with argon for 30 minutes with stirring. 0.44 g (0.4 mmol) of tetrakis(triphenylphosphine)palladium(0) is then added. The reaction mixture is heated under reflux for 16 hours and, after cooling to room temperature, extended with 500 ml of dichloromethane and 250 ml of water. The organic phase is separated off, washed twice with 100 ml of water each time, dried over magnesium sulfate and freed from solvent in a rotary evaporator. The residue is extracted twice with about 400 ml of hot toluene each time over aluminium oxide (basic, activity grade 1), recrystallised three times from ethyl acetate and twice from a toluene/heptane mixture (15:1) and finally subjected to fractional sublimation at about $10^{-6}$ mbar and 370° C., leaving 3.6 g (4 mmol, 12% of theory) of the product as a pale-yellow glass-like solid having a purity of 99.9% according to HPLC.

The following compounds can be prepared analogously:

| Ex. | Starting material 1 | Starting material 2 |
|---|---|---|
| 9b | Ex. 5c | [854952-58-2] |
| 9c | Ex. 5d | [854952-58-2] |
| 9d | Ex. 5b | [854952-58-2] |

| Ex. | Product | Yield |
|---|---|---|
| 9b | 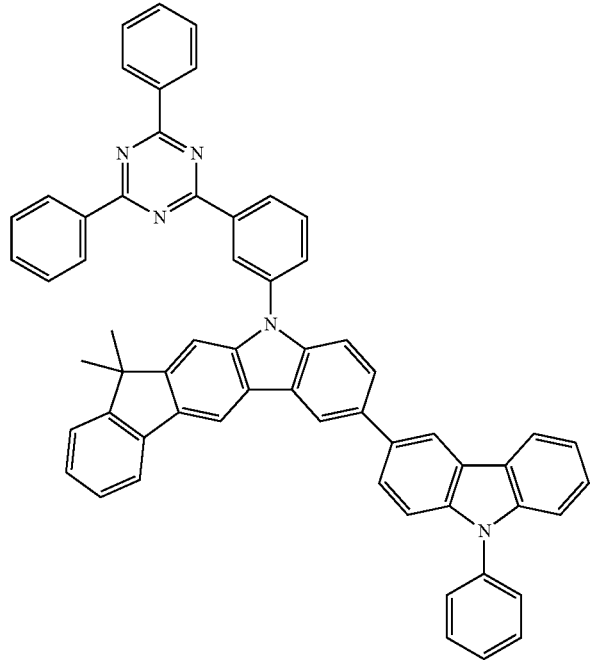 [SMILES: CC1(C)c2ccccc2-c2cc3c4cc(-c5ccc6c(c5)c5ccccc5n6-c5ccccc5)ccc4n(-c4cccc(-c5nc(-c6ccccc6)nc(-c6ccccc6)n5)c4)c3cc21] | 18% |
| 9c | 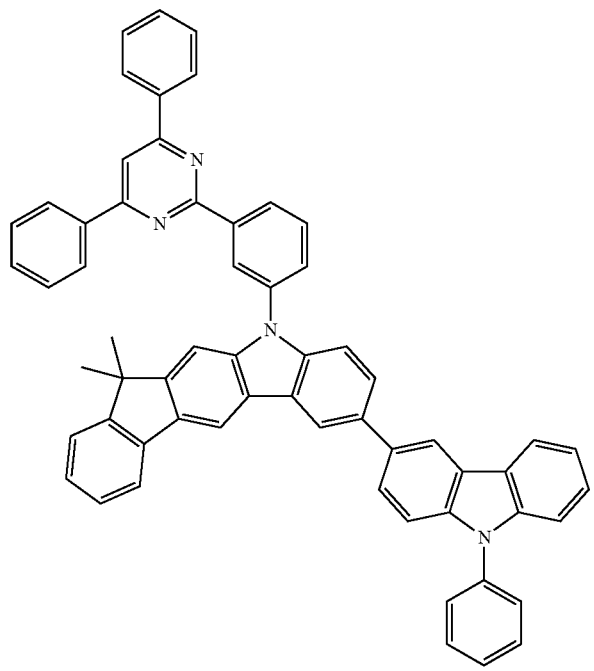 [SMILES: CC1(C)c2ccccc2-c2cc3c4cc(-c5ccc6c(c5)c5ccccc5n6-c5ccccc5)ccc4n(-c4cccc(-c5nc(-c6ccccc6)cc(-c6ccccc6)n5)c4)c3cc21] | 21% |

9d 26%

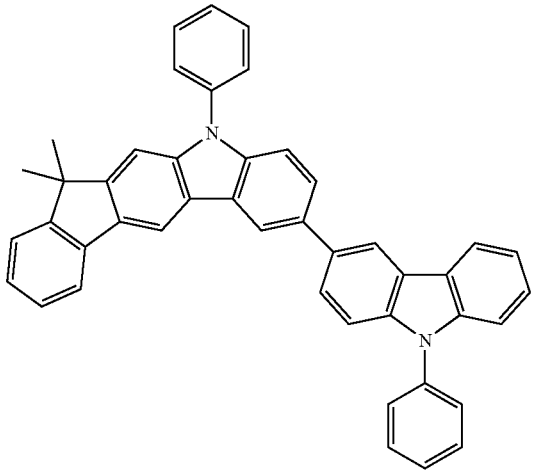 [SMILES: CC1(C)c2ccccc2-c2cc3c4cc(-c5ccc6c(c5)c5ccccc5n6-c5ccccc5)ccc4n(-c4ccccc4)c3cc21]

Example 10a

Synthesis of 12,12-dimethyl-10-[3-(4-phenyl-6-[1,1';3',1"]terphenyl-5'-yl-1,3,5-triazin-2-yl)phenyl]-10,12-dihydro-10-azaindeno[2,1-b]fluorene

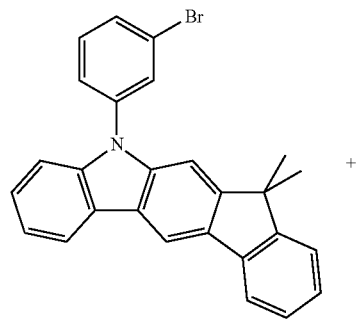

+

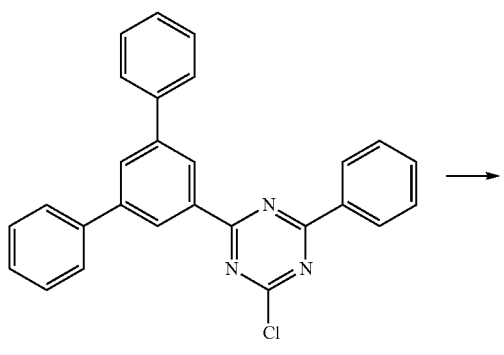

→

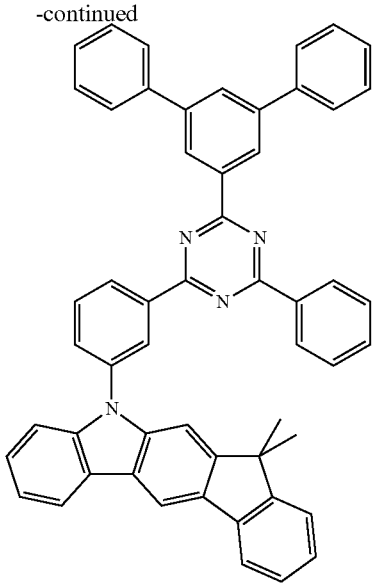

Step 1:

83.5 g (190 mmol) of 10-(3-bromophenyl)-12,12-dimethyl-10,12-dihydro-10-azaindeno[2,1-b]fluorene (Ex. 4a) are dissolved in 450 ml of THF and cooled to −78° C. 100 ml of n-butyllithium (2 M in cyclohexane, 200 mmol) are added dropwise with stirring at such a rate that the internal temperature does not exceed −65° C. After 2 hours, 32.4 ml of trimethyl borate (286 mmol) are added dropwise at such a rate that the internal temperature does not exceed −65° C. After 2 hours, the cooling is removed, and the mixture is stirred at room temperature for a further 16 hours.

Step 2:

84.0 g (200 mmol) of 2-chloro-4-phenyl-6-[1,1';3',1"]terphenyl-5'-yl-1,3,5-triazine (Ex. 1b) and 40.4 g (381 mmol) of sodium carbonate are initially introduced in a mixture of 550 ml of toluene, 250 ml of water and 250 ml of ethanol. The suspension is flushed through with argon for 30 minutes. 8.0 g (30 mmol) of triphenylphosphine and 1.7 g (8 mmol) of palladium(II) acetate are added. The solution prepared in step 1 is rapidly added dropwise with vigorous stirring, and the mixture is heated under reflux for 15 hours.

After cooling to room temperature, the solid formed is filtered off with suction, dried in vacuo and subsequently extracted twice with about 500 ml of hot toluene each time over aluminium oxide (basic, activity grade 1). The solid formed is washed by boiling with about 350 ml of heptane, dried in vacuo and finally subjected to fractional sublimation at about $10^{-5}$ mbar and 350° C., leaving 32.5 g (44 mmol, 23% of theory) of the product as a pale-yellow glass-like solid having a purity of 99.9% according to HPLC.

The following compound can be prepared analogously by using starting material 2 in step 2:

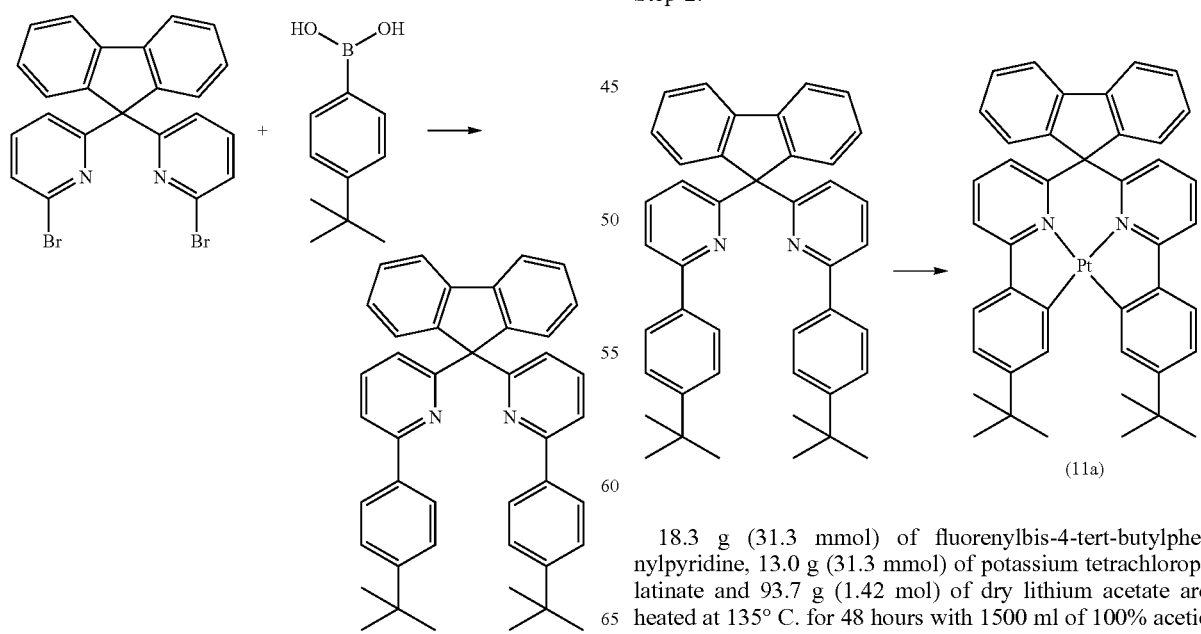

| Ex. | Starting material 2 | Product | Yield |
|---|---|---|---|
| 10b | [2915-16-4] (6-chloro-2,4-diphenylpyrimidine) | (product structure) | 53% without sublimation |

Example 11a

Synthesis of the Platinum Metal Complex (11a)

Step 1:

23 g (48.1 mmol) of 9,9'-bis(6-bromo-2-pyridyl)fluorene, 34 g (191 mmol) of 4-tert-butylphenylboronic acid and 17.25 g (297 mmol) of dry potassium fluoride are initially introduced and dispersed in 600 ml of absolute tetrahydrofuran and rendered inert by passing argon over the mixture. 421.6 mg (2.08 mmol) of tri-tert-butylphosphine and 360 mg (1.60 mmol) of palladium(II) acetate are then added, and the reaction mixture is heated under reflux for 24 hours. The reaction mixture is diluted at elevated temperature with 100 ml of water and 100 ml of ethanol, where a solid precipitates out on cooling. This is filtered off with suction, washed with water and ethanol and separated off from salts by column chromatography over silica gel with dichloromethane as eluent. The solid obtained is recrystallised a number of times from dimethylformamide, giving 19.7 g (34 mmol, 70% yield) of a colourless solid.

Step 2:

18.3 g (31.3 mmol) of fluorenylbis-4-tert-butylphenylpyridine, 13.0 g (31.3 mmol) of potassium tetrachloroplatinate and 93.7 g (1.42 mol) of dry lithium acetate are heated at 135° C. for 48 hours with 1500 ml of 100% acetic acid with exclusion of light. The acetic acid is removed in vacuo, 200 ml of ethanol are added to the residue, which is

Example 11b

Synthesis of the Platinum Metal Complex (11b)

Step 1:

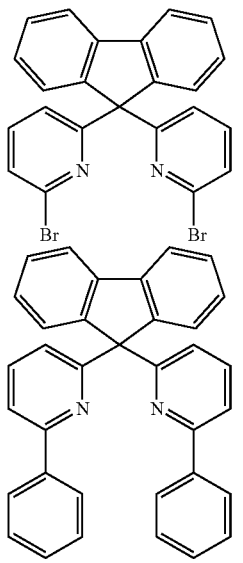 + 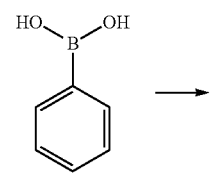 →

9.6 g (20 mmol) of 9,9'-bis(6-bromo-2-pyridyl)fluorene, 9.8 g (80 mmol) of phenylboronic acid and 7.2 g (124 mmol) of dry potassium fluoride are initially introduced and dispersed in 200 ml of absolute tetrahydrofuran and rendered inert by passing argon over the mixture. 176 mg (0.87 mmol) of tri-tert-butylphosphine and 150 mg (0.67 mmol) of palladium(II) acetate are then added, and the reaction mixture is heated under reflux for 24 hours. The reaction mixture is diluted at elevated temperature with 100 ml of water and 100 ml of ethanol, where a solid precipitates out on cooling. This is filtered off with suction, washed with water and ethanol and separated off from salts by column chromatography over silica gel with dichloromethane as eluent. The solid obtained is recrystallised a number of times from dimethylformamide, giving 8.3 g (18 mmol, 88% yield) of a colourless solid.

Step 2:

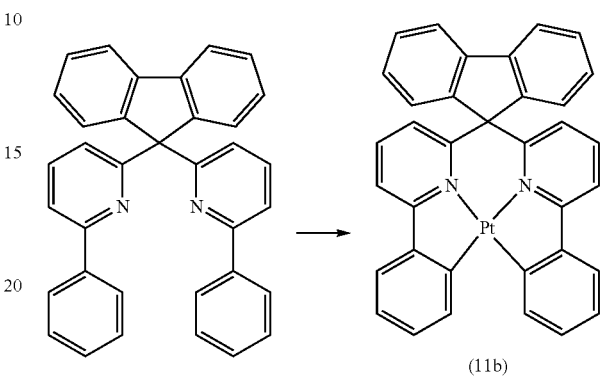

(11b)

25 g (52.9 mmol) of fluorenylbis-4-tert-butylphenylpyridine, 22 g (52.9 mmol) of potassium tetrachloroplatinate and 158.7 g (2.45 mol) of dry lithium acetate are heated at 135° C. for 48 hours with 1500 ml of 100% acetic acid with exclusion of light. The acetic acid is removed in vacuo, 200 ml of ethanol are added to the residue, which is then dispersed. The solid is filtered off with suction, rinsed with water and ethanol, dried in vacuo and subsequently extracted twice with hot dichloromethane over silica gel. The residue is recrystallised from DMF, dried in vacuo and subjected to fractional sublimation at $5*10^{-5}$ mbar and 350° C., giving 8.6 g (13 mmol) of a yellow powder in a purity of 99.9% according to HPLC.

Examples 12 and 13

Synthesis of Further Compounds in Accordance with the Literature

The following compounds can be prepared analogously to the processes described in the application indicated in each case. Any additional purification is carried out by column chromatography and/or sublimation.

--- then dispersed. The solid is filtered off with suction, rinsed with water and ethanol, dried in vacuo and subsequently extracted twice with hot dichloromethane over silica gel. The residue is recrystallised from DMF, dried in vacuo and subjected to fractional sublimation at $5*10^{-5}$ mbar and 360° C., giving 11.3 g (14 mmol) of a yellow powder in a purity of 99.8% according to HPLC.

| Ex. | Starting material 1 | Starting material 2 | Product |
|---|---|---|---|
| | | Analogously to DE102008017591A1, | |
| 12a | 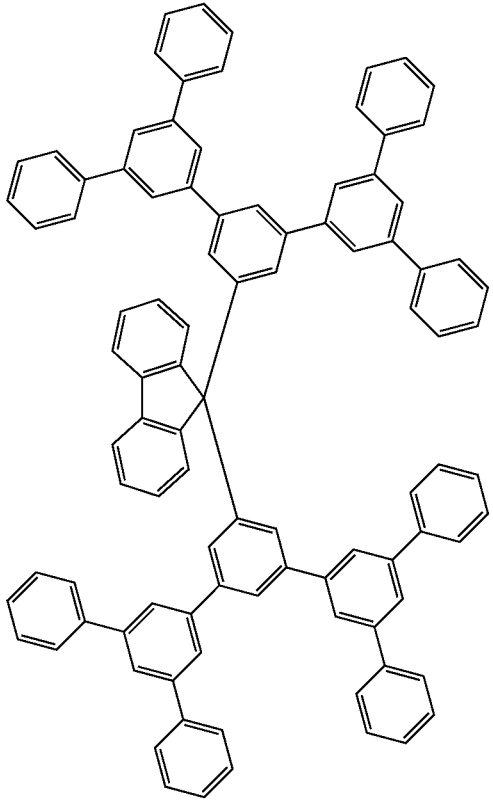 DE102008017591 | 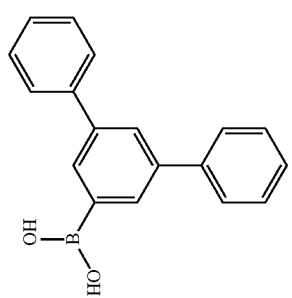 [128388-54-5] | 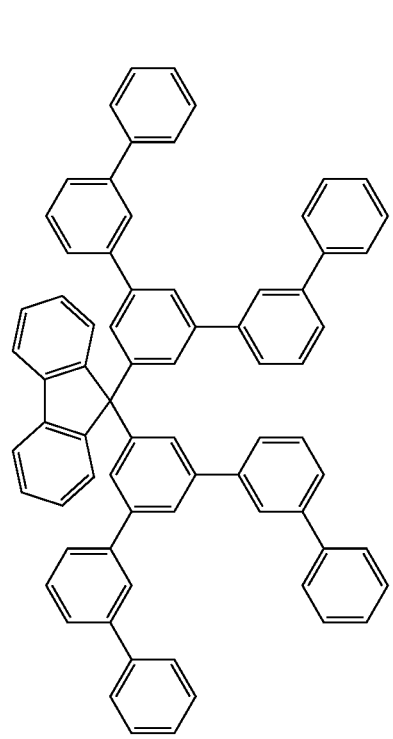 |
| 12b | 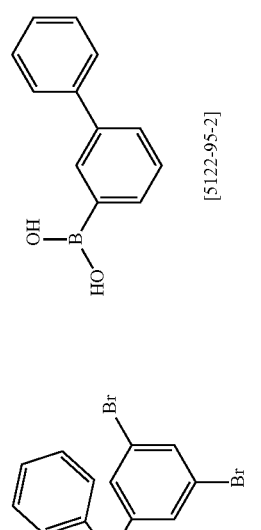 DE102008017591 | 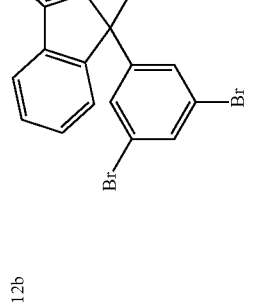 [5122-95-2] | 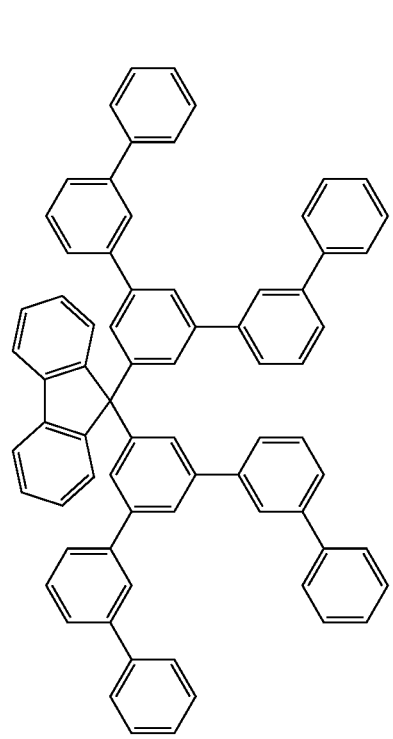 |

-continued
| Ex. | Starting material 1 | Starting material 2 | Product |
|---|---|---|---|
| 12c | 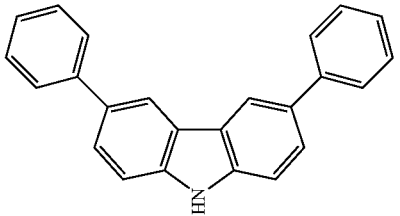 DE102010019306 | Analogously to DE102010019306A1, 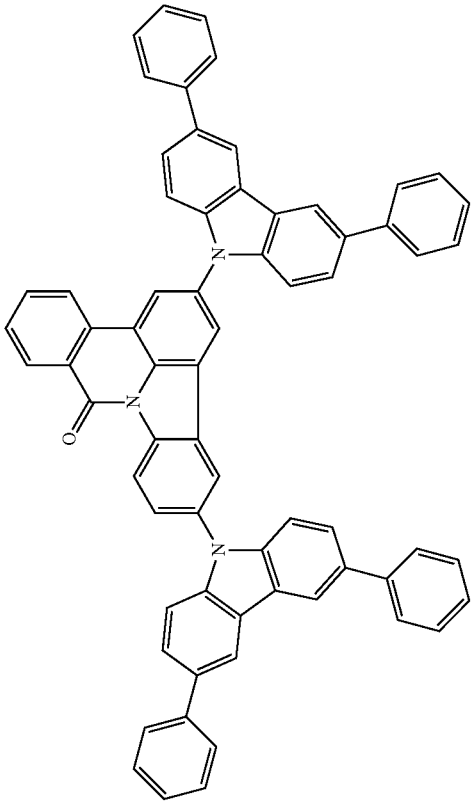 [56525-79-2] | 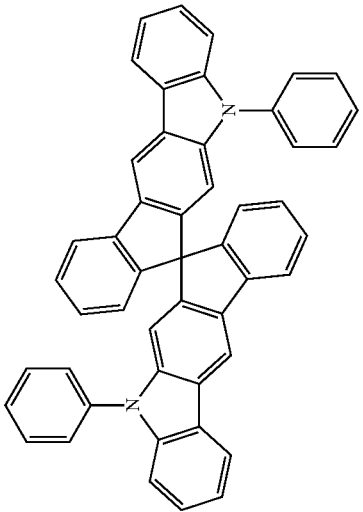 |
| 12d | 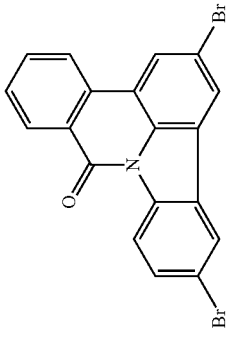 WO2010/136109 | Analogously to WO2010/136109A1 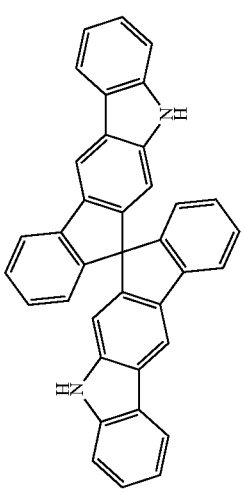 [108-86-1] | 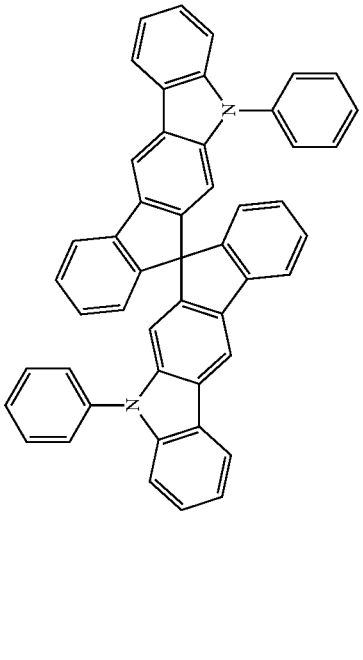 |

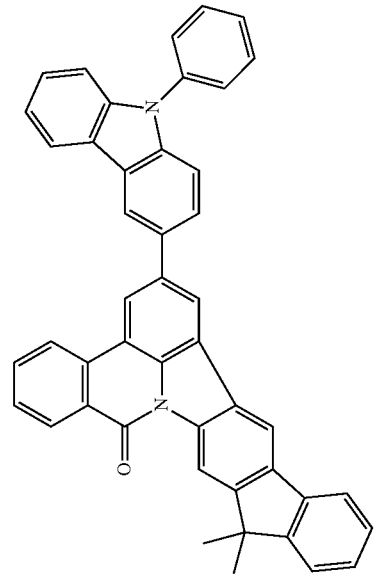

| Ex. | Starting material 1 | Starting material 2 | Product |
|---|---|---|---|
| 12g | 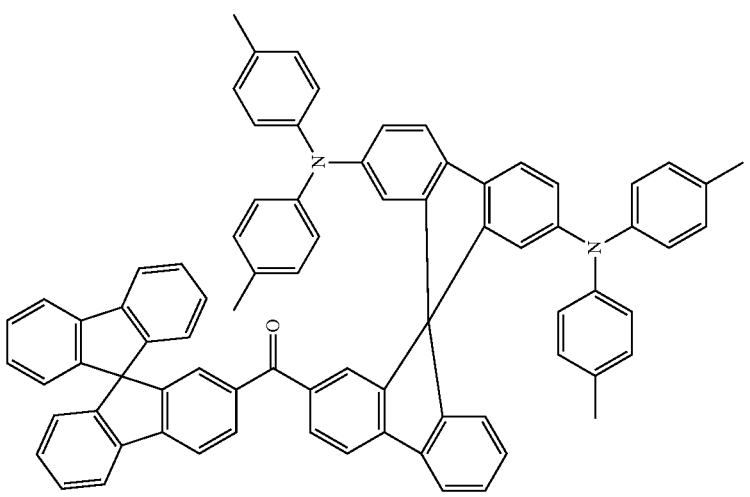 WO2007/137725A1 | 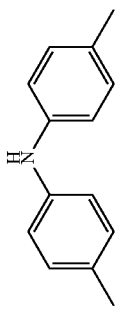 [620-93-9] | 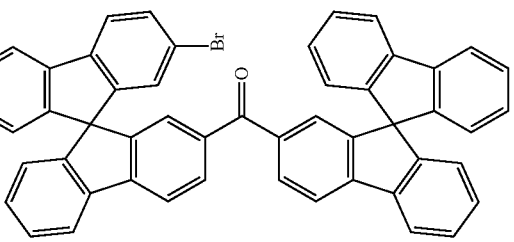 |

The following compounds can be prepared by the processes described in the application indicated in each case:

| Ex. | | Application |
|---|---|---|
| 13b | | WO 2011/137922A1 |
| 13c | | WO 2011/137922A1 |
| 13d | | WO 2011/132684A1 |
| 13e | | WO 2009/021126A9 |

| Ex. | | Application |
|---|---|---|
| 13f | 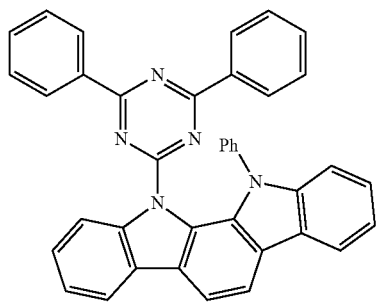 [SMILES: c1ccc(-c2nc(-c3ccccc3)nc(-n3c4ccccc4c4ccc5c6ccccc6n(-c6ccccc6)c5c43)n2)cc1] | WO 2008/056746A1 |
| 13g | 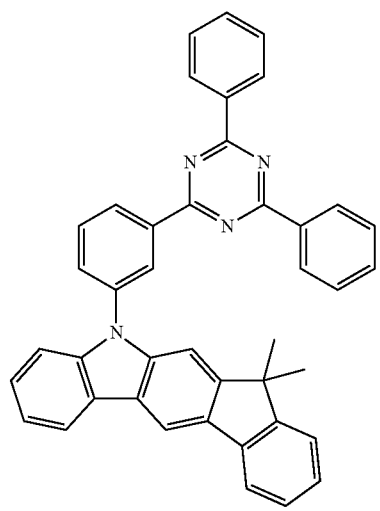 [SMILES: CC1(C)c2ccccc2-c2cc3c4ccccc4n(-c4cccc(-c5nc(-c6ccccc6)nc(-c6ccccc6)n5)c4)c3cc21] | WO 2010/136109A1 |
| 13h | 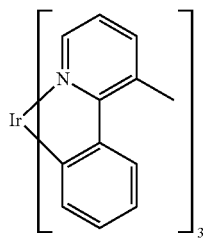 | US 2004/0241495A1 |
| 13j | 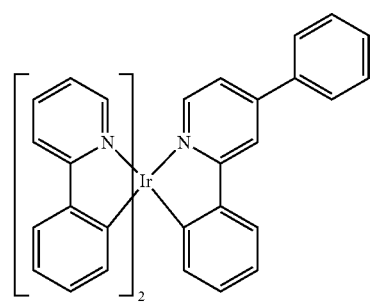 | WO 2010/027583A1 |

| Ex. | | Application |
|---|---|---|
| 13l | 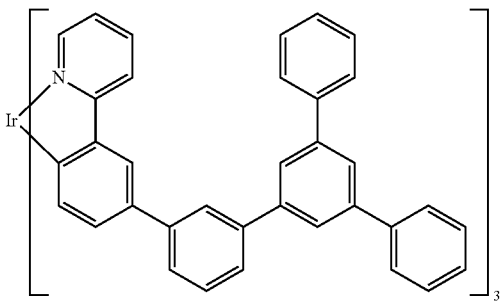 | WO 2011/137922A1 |
| 13m | 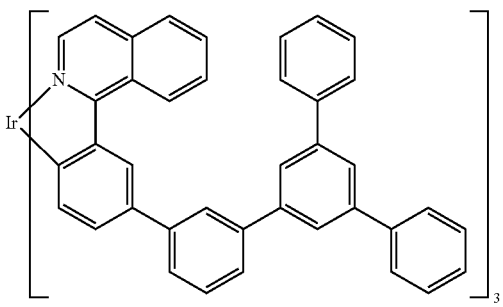 | WO 2011/137922A1 |
| 13o | 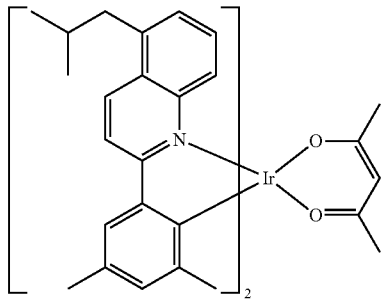 | WO2012/148511A1 |
| 13q | 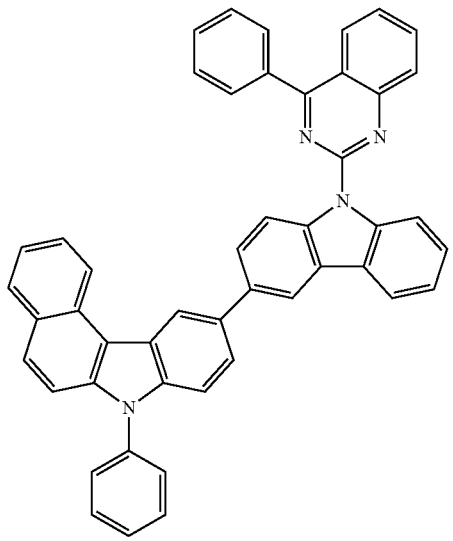 [SMILES: c1ccc(-c2nc(-n3c4ccccc4c4cc(-c5ccc6c(c5)c5c7ccccc7ccc5n6-c5ccccc5)ccc43)nc3ccccc23)cc1] | WO2012/036482A1 |

-continued
| Ex. | | Application |
|---|---|---|
| 13r | 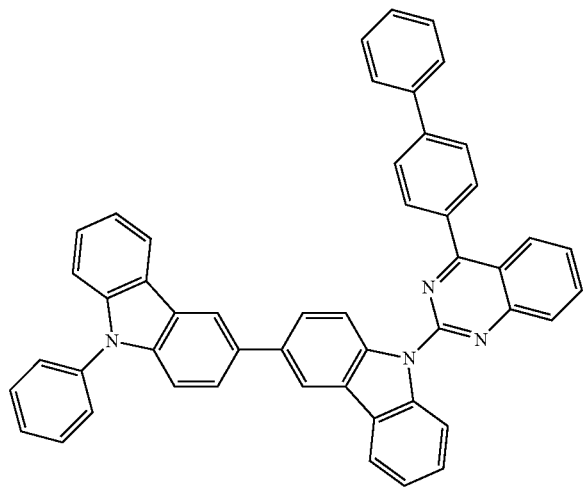 [SMILES: c1ccc(-c2ccc(-c3nc(-n4c5ccccc5c5cc(-c6ccc7c(c6)c6ccccc6n7-c6ccccc6)ccc54)nc4ccccc34)cc2)cc1] | WO 2012/121561A1 |
| 13s | 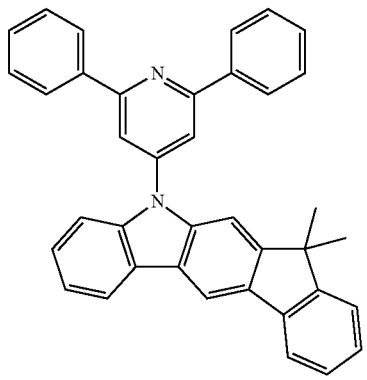 [SMILES: CC1(C)c2ccccc2-c2cc3c4ccccc4n(-c4cc(-c5ccccc5)nc(-c5ccccc5)c4)c3cc21] | WO 2010/136109A1 |
| 13t | 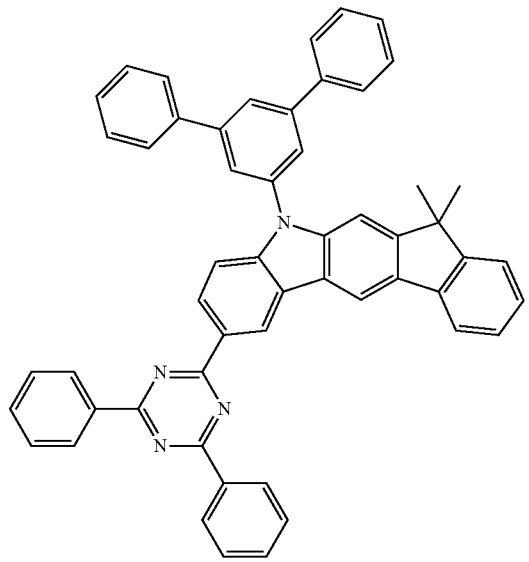 [SMILES: CC1(C)c2ccccc2-c2cc3c4cc(-c5nc(-c6ccccc6)nc(-c6ccccc6)n5)ccc4n(-c4cc(-c5ccccc5)cc(-c5ccccc5)c4)c3cc21] | WO 2010/136109A1 |

| Ex. | | Application |
|---|---|---|
| 13u | 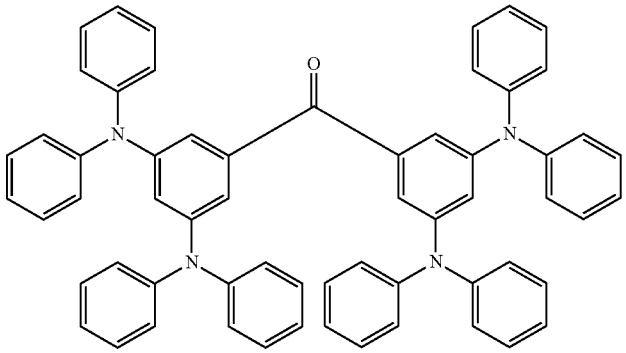 [SMILES: O=C(c1cc(N(c2ccccc2)c2ccccc2)cc(N(c2ccccc2)c2ccccc2)c1)c1cc(N(c2ccccc2)c2ccccc2)cc(N(c2ccccc2)c2ccccc2)c1] | DE102008033943A1 |
| 13v | 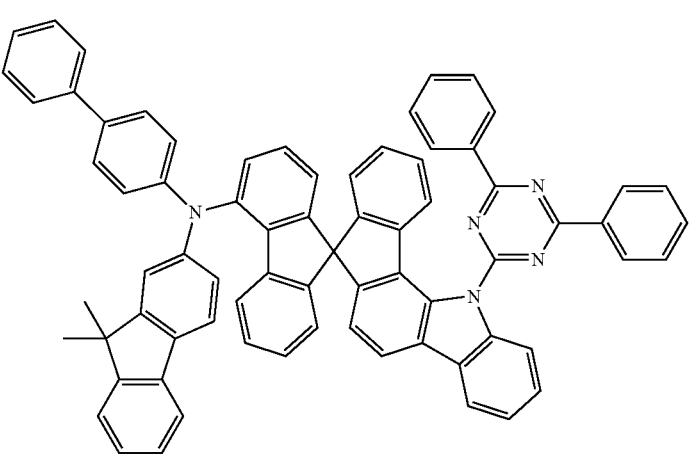 [SMILES: CC1(C)c2ccccc2-c2ccc(N(c3ccc(-c4ccccc4)cc3)c3cccc4c3-c3ccccc3C43c4ccccc4-c4c3ccc3c5ccccc5n(-c5nc(-c6ccccc6)nc(-c6ccccc6)n5)c43)cc21] | WO2014/094963A1 |
| 13w | 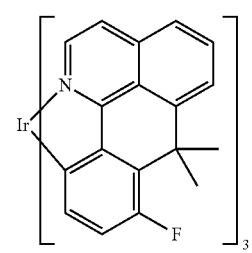 | DE10345572A1 |

Example 14

Energy Levels of the Materials Used

The energy levels of the host materials and dopants used are summarised in Table 1 and Table 2. The values are determined by the method indicated in the description.

TABLE 1

HOMO and LUMO values of the host materials

| Material | HOMO [eV] | LUMO [eV] | Method |
|---|---|---|---|
| 7a | −5.76 | −2.60 | org. |
| 8a | −5.64 | −1.66 | org. |
| 8d | −5.32 | −2.68 | org. |
| 8e | −5.19 | −2.53 | org. |
| 8f | −5.20 | −2.51 | org. |
| 8i | −5.61 | −1.97 | org. |
| 9a | −5.33 | −2.57 | org. |
| 9b | −5.33 | −2.61 | org. |
| 9c | −5.29 | −2.41 | org. |

TABLE 1-continued

HOMO and LUMO values of the host materials

| Material | HOMO [eV] | LUMO [eV] | Method |
|---|---|---|---|
| 9d | −5.32 | −1.48 | org. |
| 12a | −6.04 | −1.73 | org. |
| 12b | −6.03 | −1.68 | org. |
| 12c | −5.55 | −2.85 | org. |
| 12d | −5.43 | −2.00 | org. |
| 12e | −5.30 | −2.38 | org. |
| 12f | −5.60 | −2.44 | org. |
| 12g | −4.93 | −2.54 | org. |
| 13b | −5.93 | −2.49 | org. |
| 13c | −5.92 | −2.52 | org. |
| 13d | −5.47 | −2.36 | org. |
| 13e | −5.81 | −2.00 | org. |
| 13f | −5.67 | −2.49 | org. |
| 13g | −5.47 | −2.60 | org. |
| 13q | −5.43 | −2.62 | org. |
| 13r | −5.39 | −2.65 | org. |
| 13s | −5.61 | −1.94 | org. |
| 13t | −5.55 | −2.33 | org. |

TABLE 1-continued

HOMO and LUMO values of the host materials

| Material | HOMO [eV] | LUMO [eV] | Method |
|---|---|---|---|
| 13u | −5.27 | −2.20 | org. |
| 13v | −5.29 | −2.60 | org. |

TABLE 2

HOMO and LUMO values of the dopants

| Material | HOMO [eV] | LUMO [eV] | Method |
|---|---|---|---|
| 11a | −5.56 | −2.26 | org.-m. |
| 11b | −5.51 | −2.19 | org.-m. |
| 13h | −5.15 | −1.70 | org.-m. |
| 13j | −5.21 | −2.09 | org.-m. |
| 13l | −5.29 | −1.93 | org.-m. |
| 13m | −5.27 | −2.46 | org.-m. |

TABLE 2-continued

HOMO and LUMO values of the dopants

| Material | HOMO [eV] | LUMO [eV] | Method |
|---|---|---|---|
| 13o | −5.04 | −2.32 | org.-m. |
| 13w | −5.36 | −2.55 | org.-m. |

Example 15

Compositions According to the Invention

A selection of compositions according to the invention and comparative mixtures in accordance with the prior art are summarised in Table 3. It should be pointed out that one and the same component may adopt different roles (bipolar host, electron-transporting host, neutral co-host, etc.) depending on the position of the energy levels of the other components present in the mixture.

TABLE 3

Compositions

| No. | Type | Host B or eTMM Material | % | Co-host C or hTMM Material | % | Dopant D Material | % | Optional further component Material | % |
|---|---|---|---|---|---|---|---|---|---|
| V1 | eTMM + C | 13c | 40 | 12a | 40 | 13l | 20 | — | — |
| E1 | B + C | 8d | 20 | 12a | 60 | 13l | 20 | — | — |
| E2 | B + C | 8d | 40 | 12a | 40 | 13l | 20 | — | — |
| E3 | B + C | 9a | 40 | 12a | 40 | 13l | 20 | — | — |
| V2 | eTMM + C | 7a | 40 | 12b | 40 | 13l | 20 | — | — |
| E4 | B + C | 8d | 40 | 12b | 40 | 13l | 20 | — | — |
| E5 | B + C | 9a | 40 | 12b | 40 | 13l | 20 | — | — |
| V3 | B | 9b | 100 | — | — | 13l | 20 | — | — |
| E6 | B + C | 9b | 40 | 12a | 40 | 13l | 20 | — | — |
| V4 | B | 13u | 80 | — | — | 13l | 20 | | |
| E7 | B + C | 13u | 40 | 12b | 40 | 13l | 20 | | |
| V5 | eTMM + C | 13c | 39 | 12a | 45 | 13m | 6 | 13l | 10 |
| E8 | B + C | 9b | 39 | 12a | 45 | 13m | 6 | 13l | 10 |
| E9 | B + C | 13r | 39 | 12b | 45 | 13m | 6 | 13l | 10 |
| V6 | eTMM | 13g | 90 | — | — | 13h | 10 | — | — |
| V7 | B | 9b | 90 | — | — | 13h | 10 | — | — |
| V8 | eTMM + hTMM | 13b | 65 | 9d | 25 | 13h | 10 | — | — |
| E10 | B + C | 9c | 45 | 12b | 45 | 13h | 10 | — | — |
| E11 | B + C | 8e | 35 | 8a | 55 | 13h | 10 | — | — |
| E12 | B + C | 8f | 60 | 13s | 30 | 13h | 10 | — | — |
| V9 | B | 13g | 90 | — | — | 11a | 10 | — | — |
| E13 | B + C | 12c | 45 | 12b | 45 | 11a | 10 | — | — |
| E14 | B + C | 13d | 45 | 12b | 45 | 11a | 10 | — | — |
| E15 | B + C | 13g | 45 | 12b | 45 | 11a | 10 | — | — |
| E16 | B + C | 13t | 40 | 12b | 50 | 11a | 10 | — | — |
| V10 | B | 13f | 90 | — | — | 11b | 10 | — | — |
| E17 | B + C | 13f | 45 | 12b | 45 | 11b | 10 | — | — |
| V11 | eTMM | 13g | 90 | — | — | 13j | 10 | — | — |
| E18 | B + C | 9a | 25 | 8a | 65 | 13j | 10 | — | — |
| E19 | B + C | 9b | 25 | 12b | 65 | 13j | 10 | — | — |
| E20 | B + C | 9b | 25 | 8a | 65 | 13j | 10 | — | — |
| E21 | B + C | 9a | 35 | 13e | 55 | 13j | 10 | — | — |
| E22 | B + C | 8d | 45 | 13t | 45 | 13j | 10 | — | — |
| E23 | B + C | 13v | 30 | 8a | 60 | 13j | 10 | — | — |
| E24 | B + C | 13v | 35 | 13e | 50 | 13j | 15 | — | — |
| E25 | B + C | 12e | 30 | 8i | 60 | 13j | 10 | — | — |
| V12 | B | 12g | 95 | — | — | 13o | 5 | — | — |
| E26 | B + C | 12g | 45 | 12d | 50 | 13o | 5 | — | — |
| E27 | B + C | 12g | 45 | 8i | 50 | 13o | 5 | — | — |
| V13 | B | 13q | 90 | — | — | 13w | 10 | — | — |
| E28 | B + C | 13q | 45 | 12b | 45 | 13w | 10 | — | — |
| E29 | B + C | 12f | 45 | 12b | 45 | 11a | 10 | — | — |

C—neutral co-host;
B—bipolar host;
eTMM—electron-conducting host;
hTMM—hole-conducting host;
% data in % by weight

Example 16

Production of Solution-Processed OLEDs

Many materials can be processed from solution and may result in OLEDs which are significantly simpler to produce compared with vacuum-processed OLEDs, but nevertheless have good properties. The production of completely solution-based OLEDs has already been described many times in the literature, for example in WO 2004/037887. The production of vacuum-based OLEDs has likewise already been described many times, inter alia in WO 2004/058911.

In the examples discussed below, layers applied on a solution basis and on a vacuum basis are combined within an OLED, so that the processing up to and including the emission layer is carried out from solution and in the subsequent layers (hole-blocking layer and electron-transport layer) is carried out from vacuum. The general processes described previously are for this purpose adapted to the circumstances described here (layer-thickness variation, materials) and combined as follows:

The structure is as follows:
substrate/ITO (50 nm)/PEDOT:PSS (20 or 60 nm for green or red components respectively)/hole-transport layer (HTL) (20 nm)/emission layer (EML) (60 nm)/hole-blocking layer (HBL) (10 nm)/electron-transport layer (ETL) (40 nm)/cathode.

The substrates used are glass plates which are coated with structured ITO (indium tin oxide) in a thickness of 50 nm. For better processing, these are coated with PEDOT:PSS (poly(3,4-ethylenedioxy-2,5-thiophene):polystyrene sulfonate, purchased from Heraeus Precious Metals GmbH & Co. KG, Germany). PEDOT:PSS is applied by spin coating from water in air and subsequently dried by heating at 180° C. in air for 10 minutes in order to remove residual water. The interlayer (HTL) and the emission layer are applied to these coated glass plates.

The hole-transport layer used is crosslinkable. A polymer of the structure shown below, which is synthesised in accordance with WO 2010/097155, is used. The hole-transport polymer is dissolved in toluene. The typical solids content of such solutions is about 5 g/l if, as here, the typical layer thickness of 20 nm for a device is to be achieved by means of spin coating. The layers are applied by spin coating in an inert-gas atmosphere, in the present case argon, and dried by heating at 180° C. for 60 minutes.

The emission layer is always composed of the host material(s) and an emitting dopant (emitter). However, certain mixtures of a plurality of host materials are in accordance with the invention. Furthermore, co-dopants may occur. An expression such as TMM-A (92%):dopant (8%) here means that material TMM-A is present in the emission layer in a proportion by weight of 92% and the dopant is present in the emission layer in a proportion by weight of 8%. The composition for the emission layer is dissolved in toluene or optionally chlorobenzene. The typical solids content of such solutions is about 18 g/l if, as here, the typical layer thickness of 60 nm for a device is to be achieved by means of spin coating. The layers are applied by spin coating in an inert-gas atmosphere, in the present case argon, and dried by heating at 160° C. for 10 minutes.

The materials for the hole-blocking layer and electron-transport layer are applied by thermal vapour deposition in a vacuum chamber. The electron-transport layer, for example, here may consist of more than one material which are admixed with one another in a certain proportion by volume by co-evaporation. An expression such as ETM1:ETM2 (50%:50%) here means that materials ETM1 and ETM2 are present in the layer in a proportion by volume of 50% each. The materials used in the present case are shown in Table 4.

TABLE 4

Electron-transport materials

ETM1

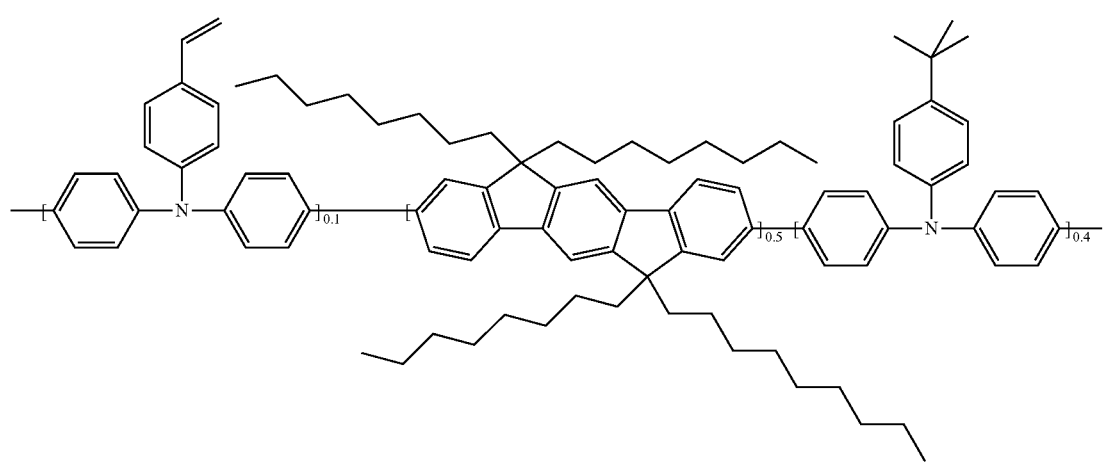

TABLE 4-continued

Electron-transport materials

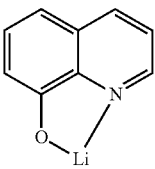

ETM2

The cathode is formed by the thermal evaporation of a 100 nm aluminium layer.

Example 17

Characterisation of the Solution-Processed OLEDs

The OLEDs are characterised by standard methods. For this purpose, the electroluminescence spectra, current/voltage/luminous density characteristic lines (IUL characteristic lines) assuming Lambert emission characteristics, and the (operating) lifetime are determined. The IUL characteristic lines are used to determine characteristic numbers such as the operating voltage (in V) and the external quantum efficiency (in %) at a certain luminance. LT80 @ 8000 cd/m$^2$ is the lifetime by which the OLED has dropped from an initial luminance of 8000 cd/m$^2$ to 80% of the initial intensity, i.e. to 6400 cd/m$^2$. Correspondingly, LT80 @ 10,000 cd/m$^2$ is the lifetime by which the OLED has dropped from an initial luminance of 10,000 cd/m$^2$ to 80% of the initial intensity, i.e. to 8000 cd/m$^2$.

The data of OLEDs whose EMLs consist of compositions in accordance with Table 3 are shown in Table 5. ETM1 was used here as HBL and ETM1:ETM2 (50%:50%) was used as ETL.

TABLE 5

Results of solution-processed OLEDs

| No. | Efficiency at 1000 cd/m$^2$ [% EQE] | LT80 | Starting condition for LT |
|---|---|---|---|
| V1 | 16 | 132 | 10000 cd/m$^2$ |
| E1 | 20 | 529 | 10000 cd/m$^2$ |
| E2 | 18.2 | 372 | 10000 cd/m$^2$ |
| E3 | 19.7 | 326 | 10000 cd/m$^2$ |
| V2 | 18.3 | 272 | 10000 cd/m$^2$ |
| E4 | 19 | 402 | 10000 cd/m$^2$ |
| E5 | 20.1 | 308 | 10000 cd/m$^2$ |
| V3 | 17.9 | 141 | 10000 cd/m$^2$ |
| E6 | 19.6 | 332 | 10000 cd/m$^2$ |
| V4 | 15.7 | 40 | 10001 cd/m$^2$ |
| E7 | 17.9 | 125 | 10002 cd/m$^2$ |
| V5 | 14.7 | 54 | 8000 cd/m$^2$ |
| E8 | 14.2 | 178 | 8000 cd/m$^2$ |
| E9 | 14.4 | 211 | 8000 cd/m$^2$ |

Example 18

Production and Characterisation of Vacuum-Processed OLEDs

Many OLED materials can be evaporated in vacuo. In the examples discussed below, layers applied exclusively on a vacuum basis were used. The general processes described previously are for this purpose adapted to the circumstances described here (layer-thickness variation, materials).

The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL) and finally a cathode. The cathode is formed by an aluminium layer with a thickness of 100 nm. The precise structure of the OLEDs and the resultant results are shown in Table 7. The auxiliary materials required for the production of the OLEDs are shown in Table 6; compositions used are given in Table 3.

TABLE 6

Structures of the auxiliary materials used

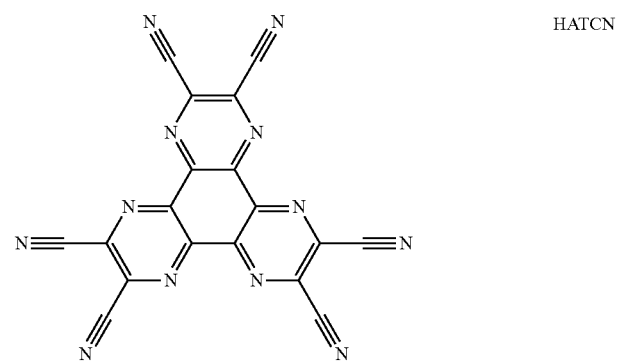

HATCN

TABLE 6-continued
Structures of the auxiliary materials used
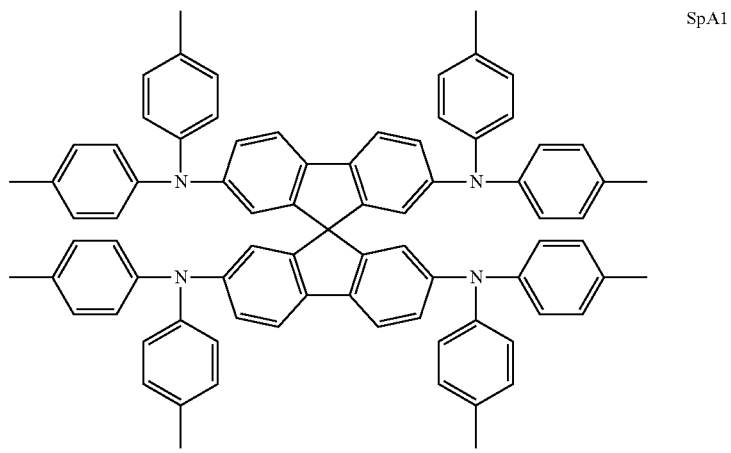
SpA1
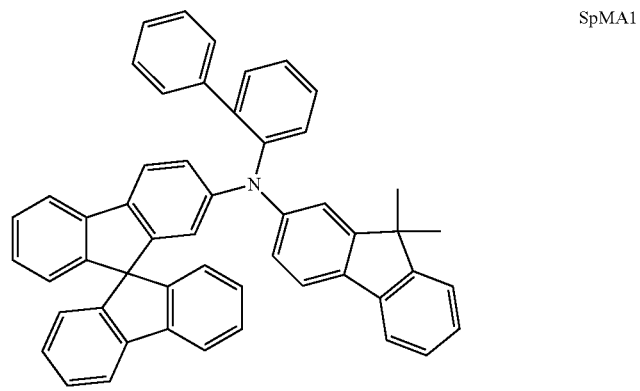
SpMA1
LiQ
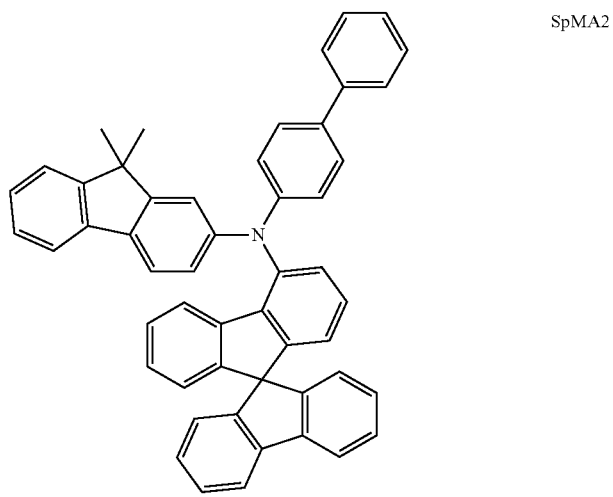
SpMA2

TABLE 6-continued

Structures of the auxiliary materials used

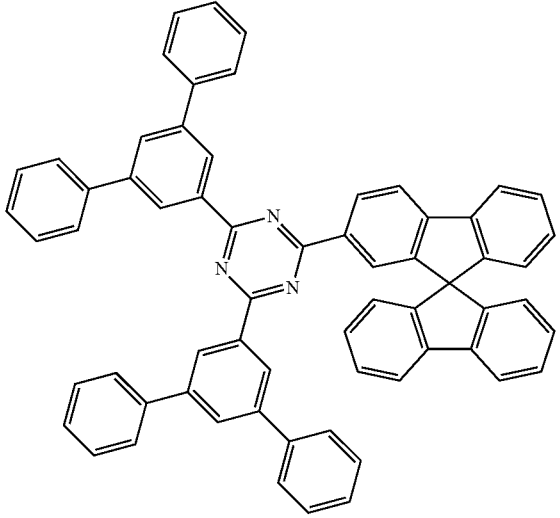 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2

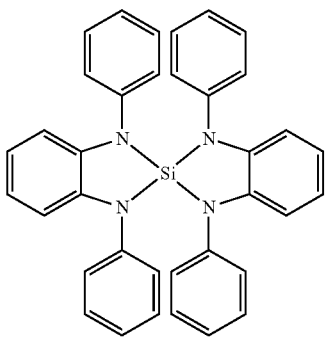 [SMILES: c1ccc(N2c3ccccc3N(c3ccccc3)[Si]23N(c2ccccc2)c2ccccc2N3c2ccccc2)cc1]
EBM1

TABLE 7

Structure and results of vacuum-processed OLEDs

| No. | HTL (thickness) | IL (thickness) | EBL (thickness) | EML (thickness) | HBL (thickness) | ETL (thickness) | EQE | LT80 | Starting cond. for LT |
|---|---|---|---|---|---|---|---|---|---|
| V6 | SpA1 (70 nm) | HATCN (5 nm) | SpMA1 (90 nm) | V6 (30 nm) | ST2 (10 nm) | ST2:LiQ (50:50) (30 nm) | 15.3 | 200 | 20 mA/cm$^2$ |
| V7 | SpA1 (70 nm) | HATCN (5 nm) | SpMA1 (90 nm) | V7 (30 nm) | ST2 (10 nm) | ST2:LiQ (50%:50%) (30 nm) | 13 | 130 | 20 mA/cm$^2$ |
| V8 | SpA1 (70 nm) | HATCN (5 nm) | SpMA1 (90 nm) | V8 (30 nm) | ST2 (10 nm) | ST2:LiQ (50%:50%) (30 nm) | 16.9 | 230 | 20 mA/cm$^2$ |
| E10 | SpA1 (70 nm) | HATCN (5 nm) | SpMA1 (90 nm) | E10 (30 nm) | ST2 (10 nm) | ST2:LiQ (50%:50%) (30 nm) | 18.5 | 200 | 20 mA/cm$^2$ |
| E11 | SpA1 (70 nm) | HATCN (5 nm) | SpMA1 (90 nm) | E11 (30 nm) | ST2 (10 nm) | ST2:LiQ (50%:50%) (30 nm) | 18.8 | 120 | 20 mA/cm$^2$ |
| E12 | SpA1 (70 nm) | HATCN (5 nm) | SpMA1 (90 nm) | E12 (30 nm) | ST2 (10 nm) | ST2:LiQ (50%:50%) (30 nm) | 18.7 | 6 | 20 mA/cm$^2$ |
| V9 | HATCN (5 nm) | SpMA1 (65 nm) | EBM1 (15 nm) | V9 (30 nm) | ST2 (10 nm) | ST2:LiQ (50%:50%) (30 nm) | 15.2 | 15 | 20 mA/cm$^2$ |
| E13 | HATCN (5 nm) | SpMA1 (65 nm) | EBM1 (15 nm) | E13 (30 nm) | ST2 (10 nm) | ST2:LiQ (50%:50%) (30 nm) | 14.9 | 30 | 20 mA/cm$^2$ |

TABLE 7-continued

Structure and results of vacuum-processed OLEDs

| No. | HTL (thickness) | IL (thickness) | EBL (thickness) | EML (thickness) | HBL (thickness) | ETL (thickness) | EQE | LT80 | Starting cond. for LT |
|---|---|---|---|---|---|---|---|---|---|
| E14 | HATCN (5 nm) | SpMA1 (65 nm) | EBM1 (15 nm) | E14 (30 nm) | ST2 (10 nm) | ST2:LiQ (50%:50%) (30 nm) | 16.4 | 40 | 20 mA/cm$^2$ |
| E15 | HATCN (5 nm) | SpMA1 (65 nm) | EBM1 (15 nm) | E15 (30 nm) | ST2 (10 nm) | ST2:LiQ (50%:50%) (30 nm) | 15.7 | 50 | 20 mA/cm$^2$ |
| E16 | HATCN (5 nm) | SpMA1 (65 nm) | EBM1 (15 nm) | E16 (30 nm) | ST2 (10 nm) | ST2:LiQ (50%:50%) (30 nm) | 16.1 | 20 | 20 mA/cm$^2$ |
| V10 | HATCN (5 nm) | SpMA1 (65 nm) | EBM1 (15 nm) | V10 (30 nm) | ST2 (10 nm) | ST2:LiQ (50%:50%) (30 nm) | 15.3 | 30 | 20 mA/cm$^2$ |
| E17 | HATCN (5 nm) | SpMA1 (65 nm) | EBM1 (15 nm) | E17 (30 nm) | ST2 (10 nm) | ST2:LiQ (50%:50%) (30 nm) | 15.8 | 45 | 20 mA/cm$^2$ |
| V11 | HATCN (5 nm) | SpMA1 (70 nm) | SpMA2 (15 nm) | V11 (25 nm) | ST2 (45 nm) | LiQ (3 nm) | 21 | 2000 | 20 mA/cm$^2$ |
| E18 | HATCN (5 nm) | SpMA1 (70 nm) | SpMA2 (15 nm) | E18 (25 nm) | ST2 (45 nm) | LiQ (3 nm) | 22.5 | 3700 | 20 mA/cm$^2$ |
| E19 | HATCN (5 nm) | SpMA1 (70 nm) | SpMA2 (15 nm) | E19 (25 nm) | ST2 (45 nm) | LiQ (3 nm) | 21.7 | 3900 | 20 mA/cm$^2$ |
| E20 | HATCN (5 nm) | SpMA1 (70 nm) | SpMA2 (15 nm) | E20 (25 nm) | ST2 (45 nm) | LiQ (3 nm) | 21.5 | 4200 | 20 mA/cm$^2$ |
| E21 | HATCN (5 nm) | SpMA1 (70 nm) | SpMA2 (15 nm) | E21 (25 nm) | ST2 (45 nm) | LiQ (3 nm) | 22.7 | 3500 | 20 mA/cm$^2$ |
| E22 | HATCN (5 nm) | SpMA1 (70 nm) | SpMA2 (15 nm) | E22 (25 nm) | ST2 (45 nm) | LiQ (3 nm) | 21.3 | 2600 | 20 mA/cm$^2$ |
| E23 | HATCN (5 nm) | SpMA1 (70 nm) | SpMA2 (15 nm) | E23 (25 nm) | ST2 (45 nm) | LiQ (3 nm) | 23.2 | 2200 | 20 mA/cm$^2$ |
| E24 | HATCN (5 nm) | SpMA1 (70 nm) | SpMA2 (15 nm) | E24 (25 nm) | ST2 (45 nm) | LiQ (3 nm) | 22.5 | 2000 | 20 mA/cm$^2$ |
| E25 | HATCN (5 nm) | SpMA1 (70 nm) | SpMA2 (15 nm) | E25 (25 nm) | ST2 (45 nm) | LiQ (3 nm) | 22.1 | 1700 | 20 mA/cm$^2$ |
| V12 | SpA1 (90 nm) | HATCN (5 nm) | SpMA1 (130 nm) | V12 (30 nm) | 0 | ST2:LiQ (50:50) (40 nm) | 19.4 | 1300 | 20 mA/cm$^2$ |
| E26 | SpA1 (90 nm) | HATCN (5 nm) | SpMA1 (130 nm) | E26 (30 nm) | 0 | ST2:LiQ (50:50) (40 nm) | 19.7 | 1800 | 20 mA/cm$^2$ |
| E27 | SpA1 (90 nm) | HATCN (5 nm) | SpMA1 (130 nm) | E27 (30 nm) | 0 | ST2:LiQ (50:50) (40 nm) | 19.3 | 1900 | 20 mA/cm$^2$ |
| V13 | SpA1 (90 nm) | HATCN (5 nm) | SpMA1 (130 nm) | V13 (30 nm) | 0 | ST2:LiQ (50:50) (40 nm) | 13.7 | 50 | 20 mA/cm$^2$ |
| E28 | SpA1 (90 nm) | HATCN (5 nm) | SpMA1 (130 nm) | E28 (30 nm) | 0 | ST2:LiQ (50:50) (40 nm) | 14.2 | 90 | 20 mA/cm$^2$ |
| E29 | HATCN (5 nm) | SpMA1 (65 nm) | EBM1 (15 nm) | E29 (30 nm) | ST2 (10 nm) | ST2:LiQ (50%:50%) (30 nm) | 15.8 | 30 | 20 mA/cm$^2$ |

EQE: efficiency in % at 1000 cd/m$^2$;
Starting cond.: starting condition

The invention claimed is:

1. A composition comprising a bipolar host, a neutral co-host and a light-emitting dopant wherein (a) the following conditions are satisfied:

$|HOMO(C)|-\min\{|HOMO(D)|;|HOMO(B)|\}>0.3$ eV $|HOMO(B)|-|HOMO(D)|<0.15$ eV $|LUMO(B)|-|LUMO(C)|>0.3$ eV $|LUMO(B)|-|LUMO(D)|>0$, where HOMO(C) stands for the HOMO energy of the neutral co-host, HOMO(B) and HOMO(D) correspondingly stand for the HOMO energy of the bipolar host and of the dopant respectively, LUMO(C), LUMO (B) and LUMO(D) correspondingly stand for the LUMO energy of the neutral co-host, of the bipolar host and of the dopant respectively, and the function min$\{|HOMO(D)|;|HOMO(B)|\}$ supplies the smaller of the two values $|HOMO(D)|$ and $|HOMO(B)|$, or (b) wherein the following conditions are satisfied:

$\max\{|LUMO(D)|;|LUMO(B)|\}-|LUMO(C)|>0.3$ eV $|LUMO(D)|-|LUMO(B)|<0.15$ eV $|HOMO(C)|-|HOMO(B)|>0.3$ eV $|HOMO(D)|-|HOMO(B)|>0$, where the function max$\{|LUMO(D)|; |LUMO(B)|\}$ supplies the larger of the two values $|LUMO(D)|$ and $|LUMO(B)|$, wherein the light emitting dopant is selected from phosphorescent emitters:
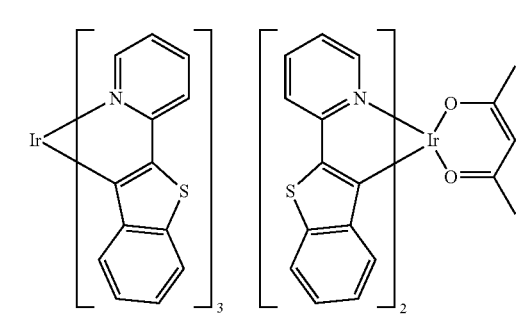
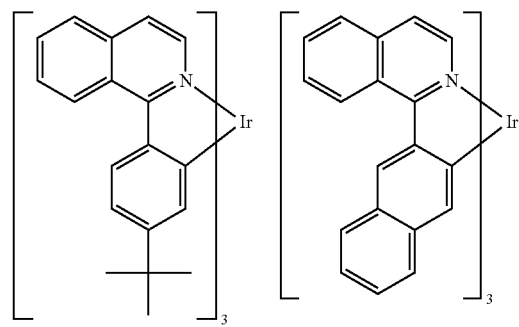
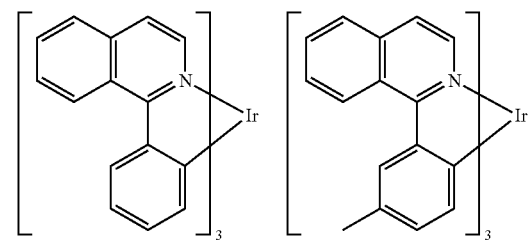
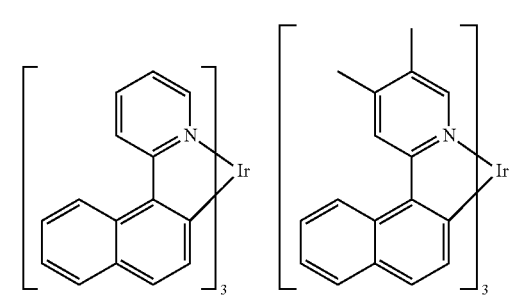
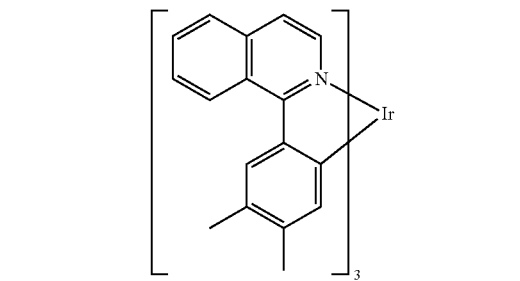
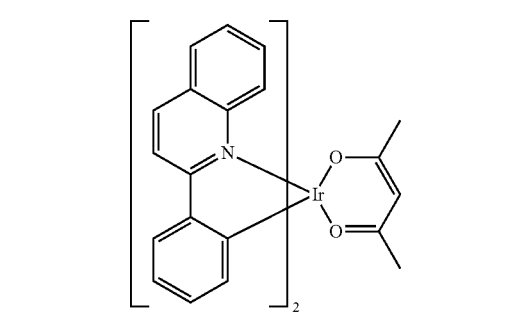
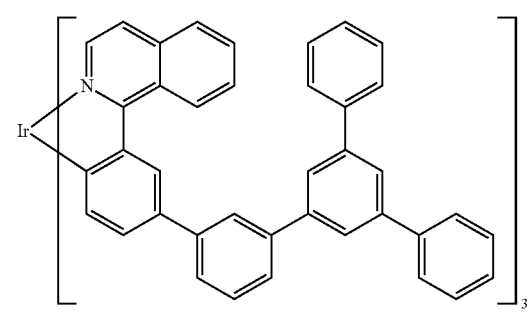
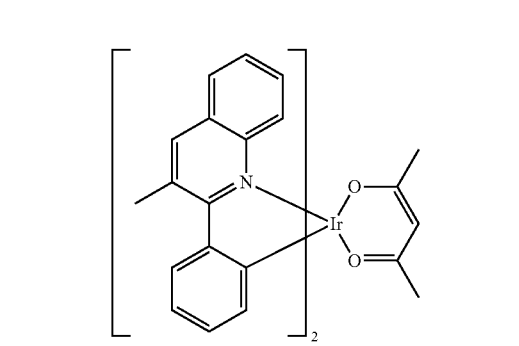
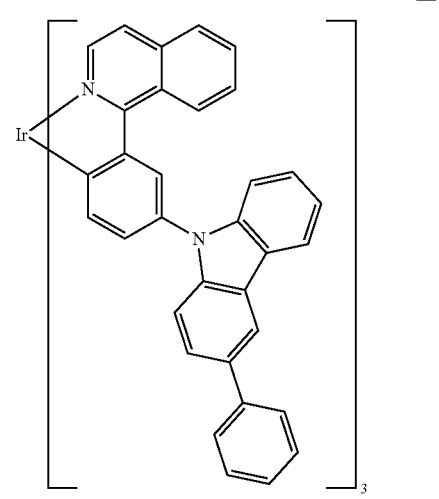
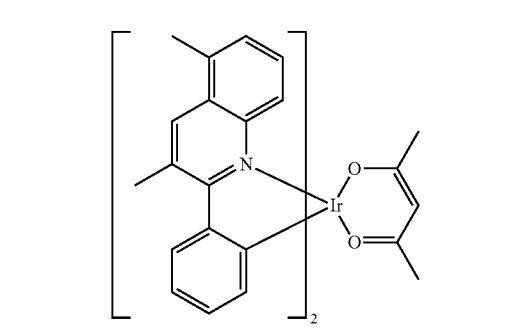

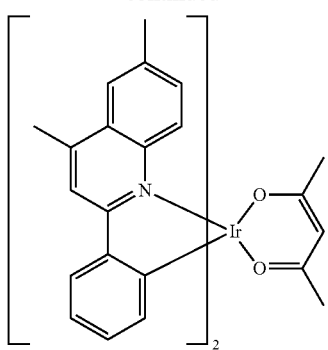
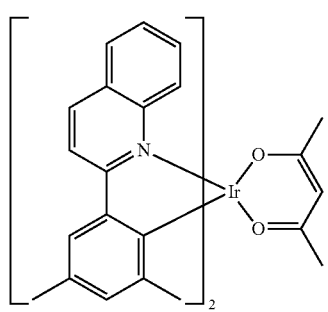
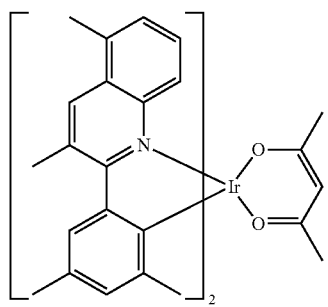
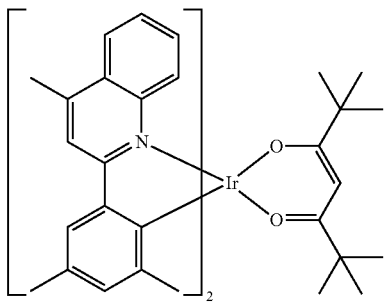
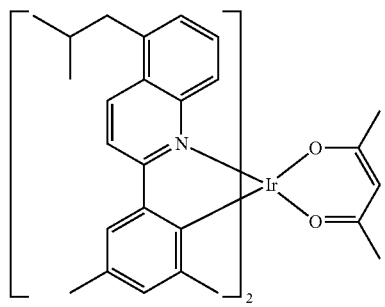
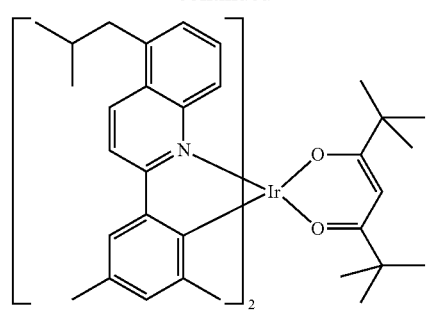
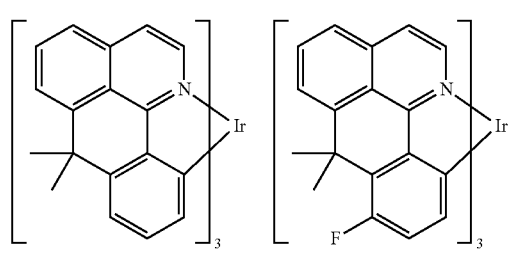
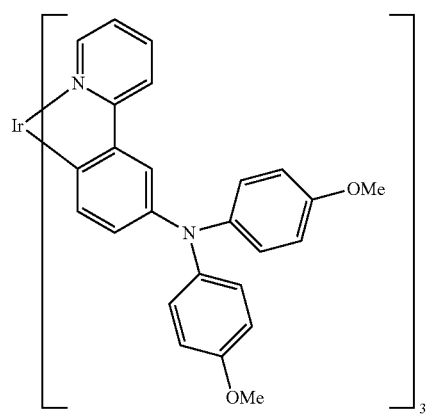
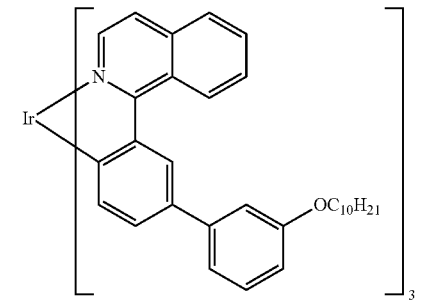
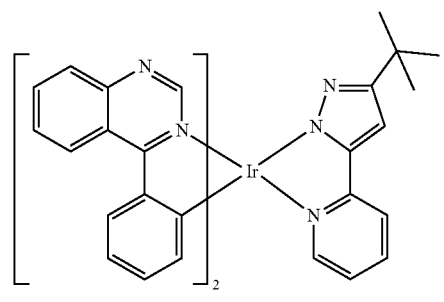

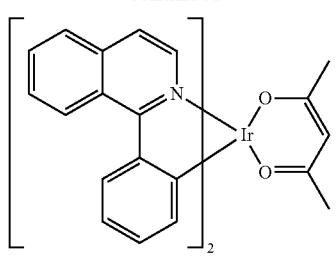
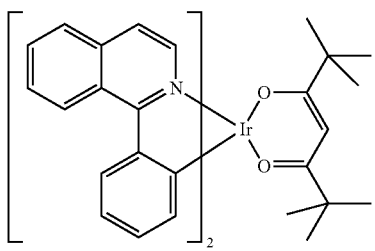
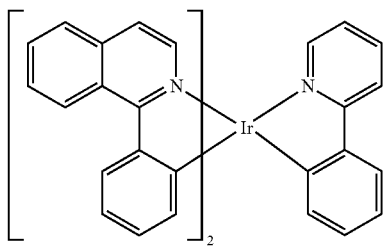
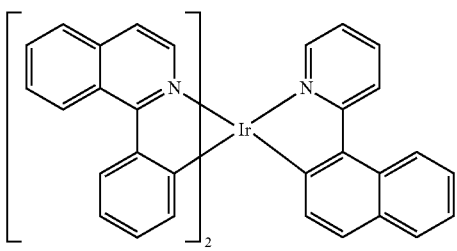
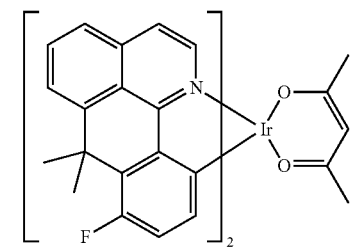
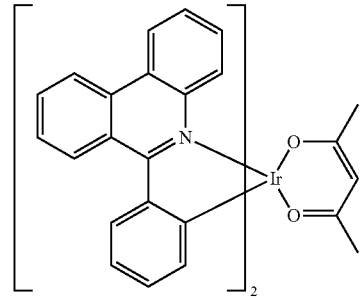
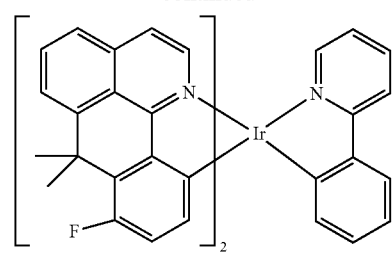
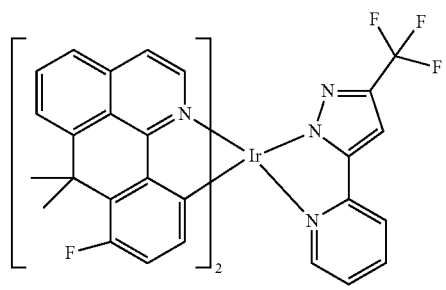
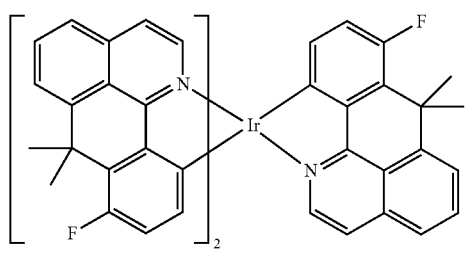
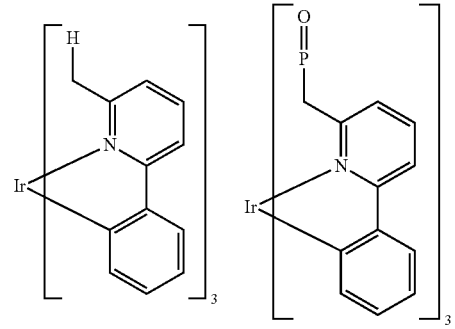
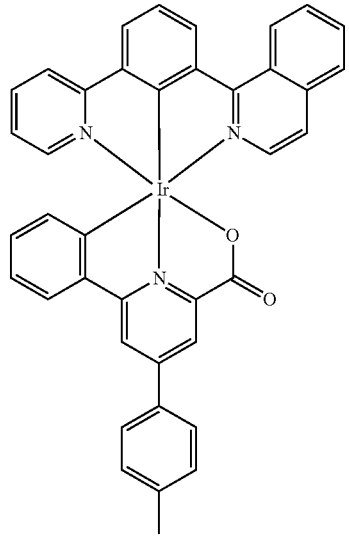

109
-continued
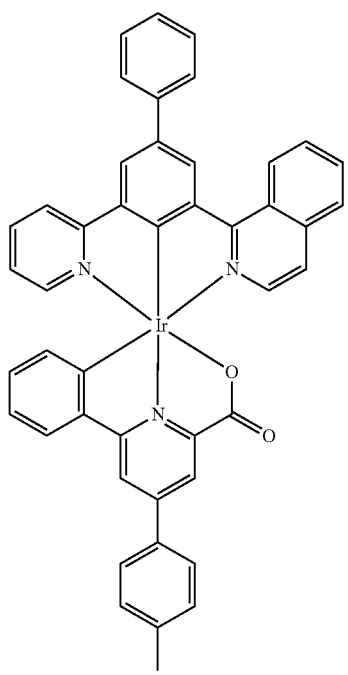
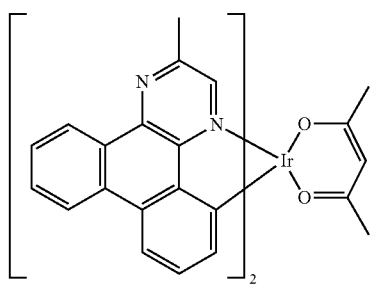
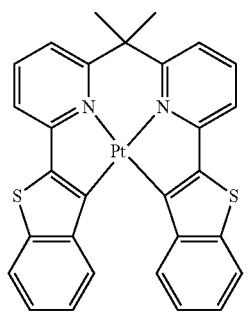
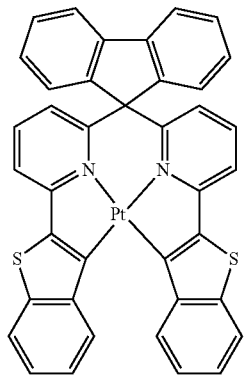
110
-continued
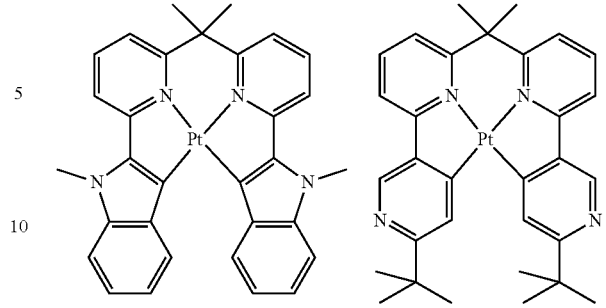
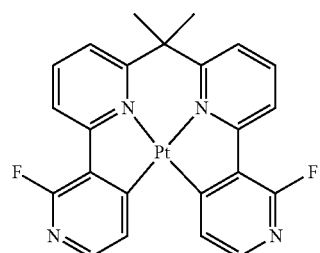
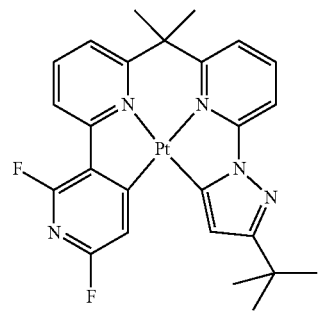
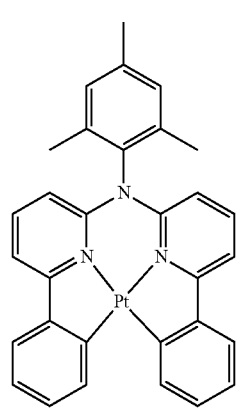

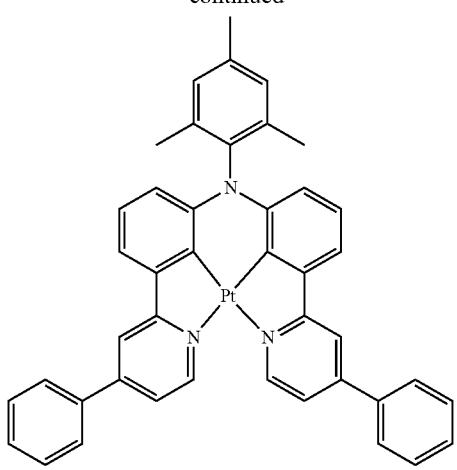
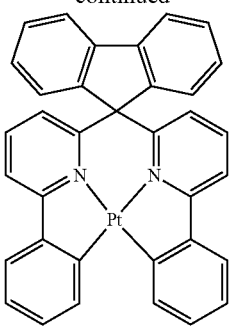
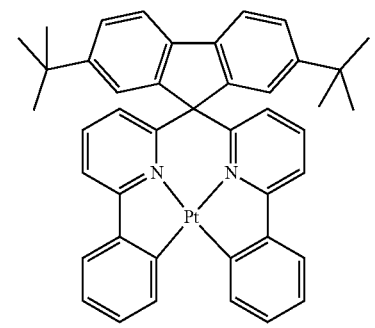
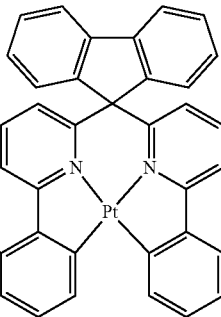
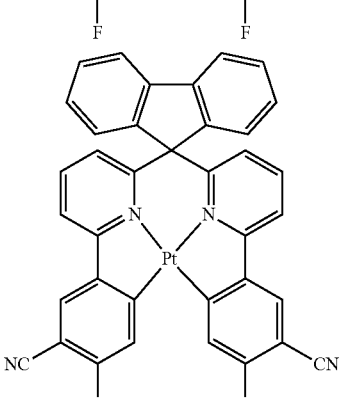
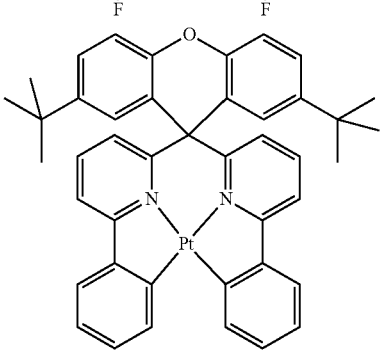

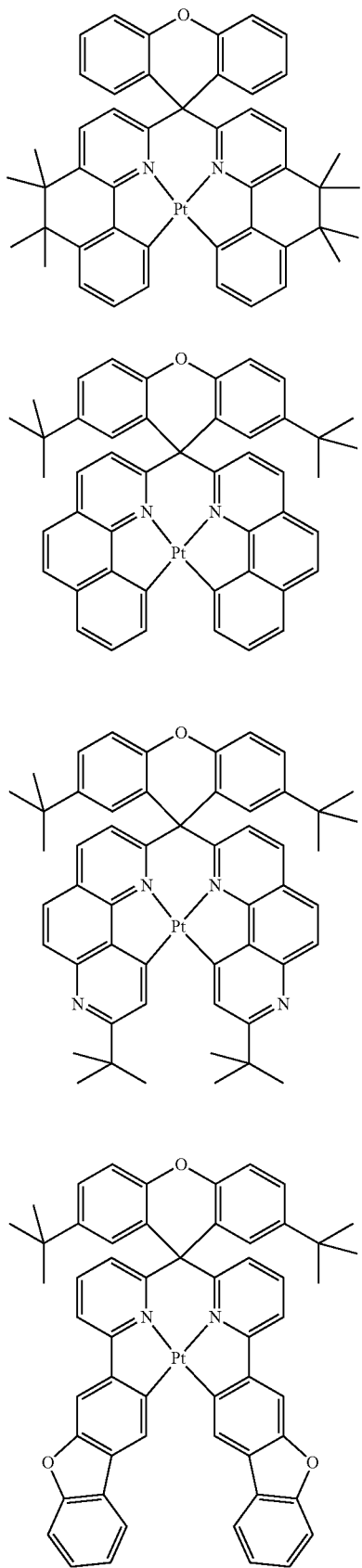
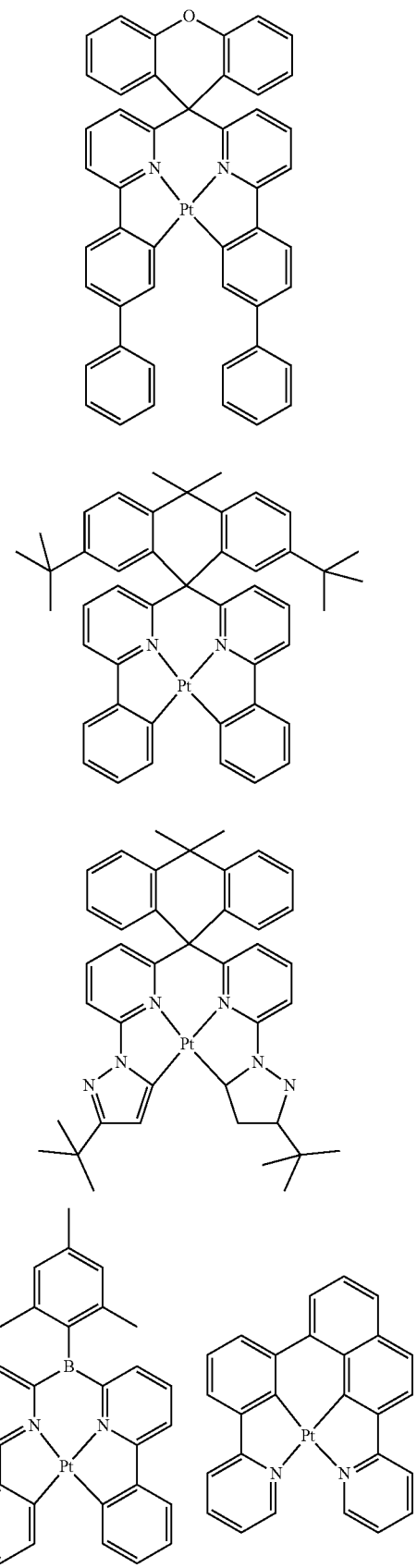

115
-continued
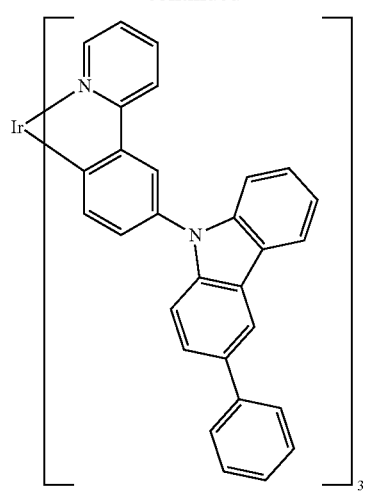
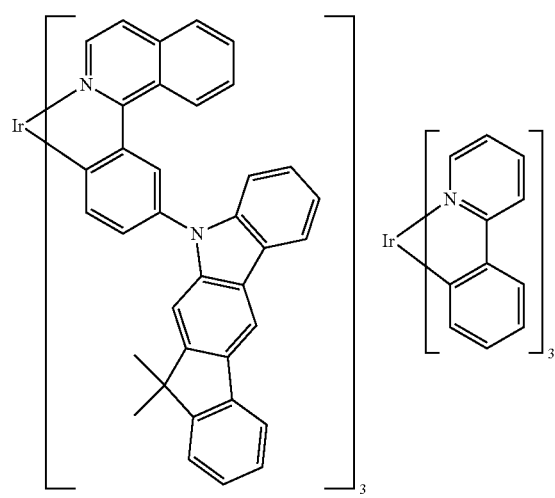
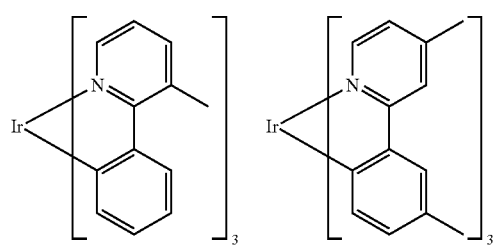
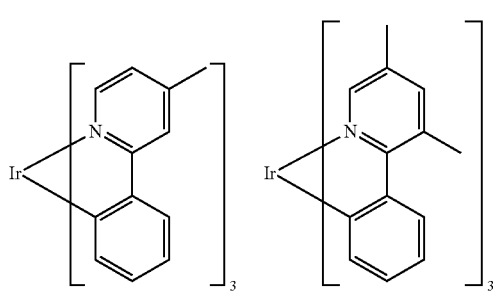
116
-continued
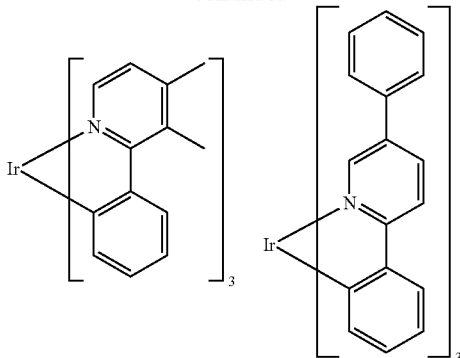
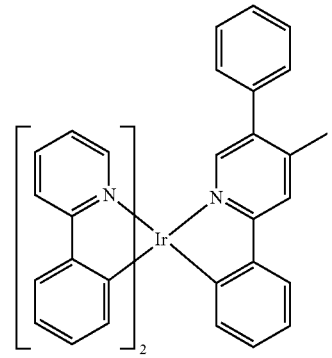
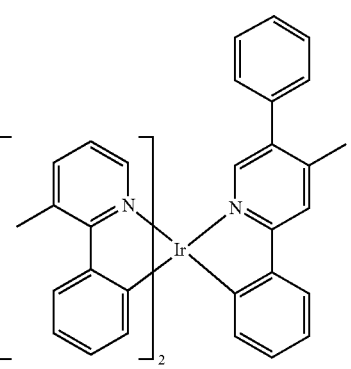
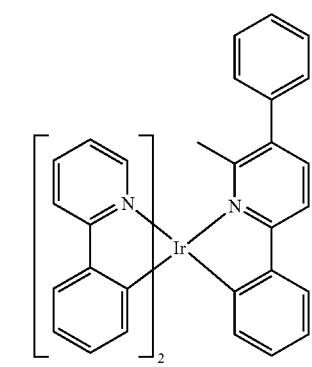

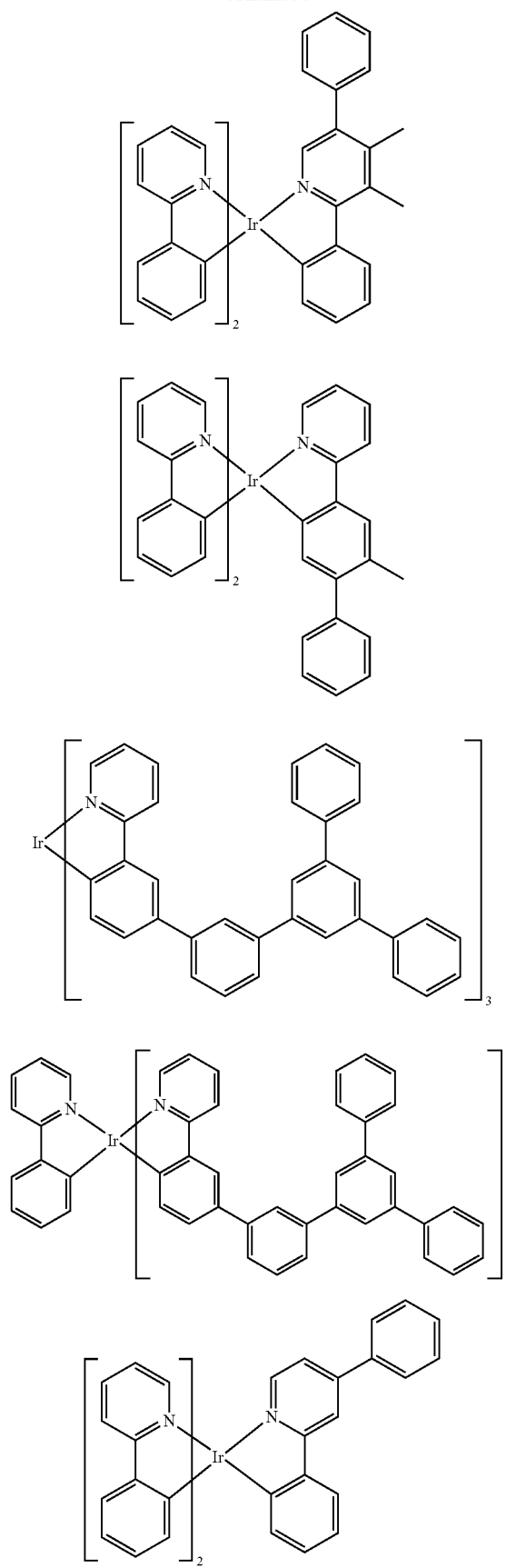

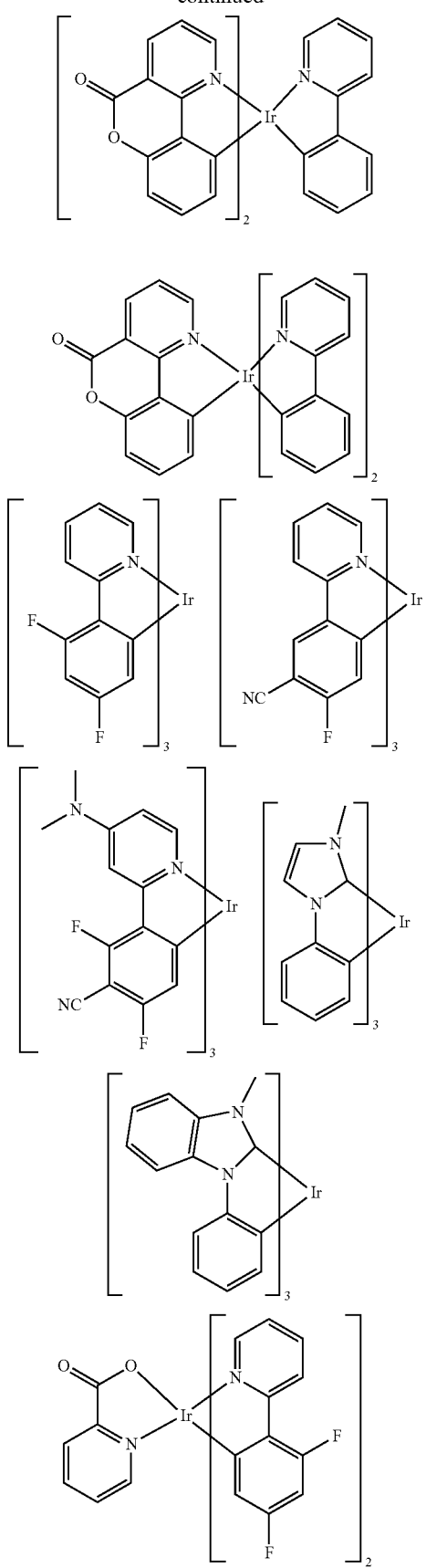
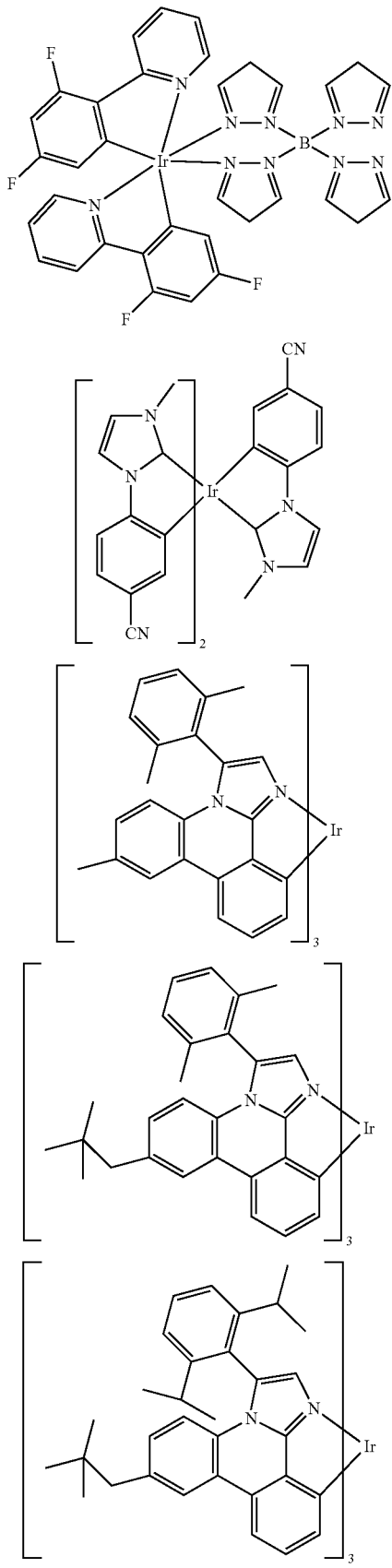

121
-continued
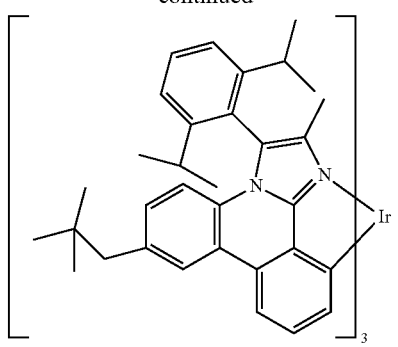
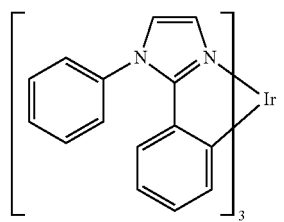
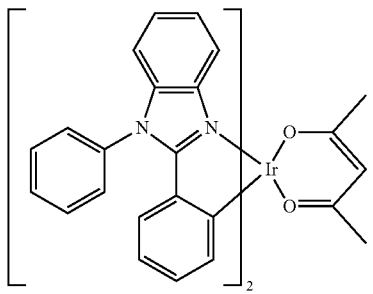
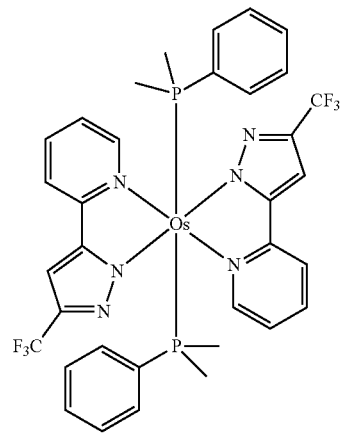
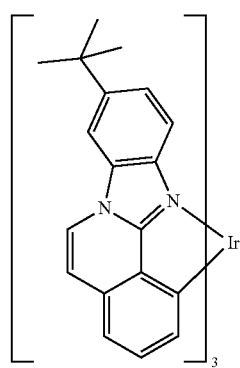
122
-continued
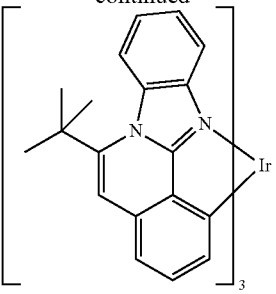
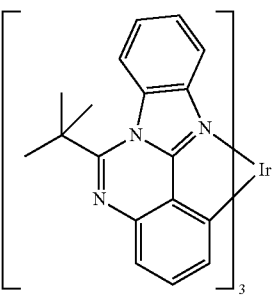
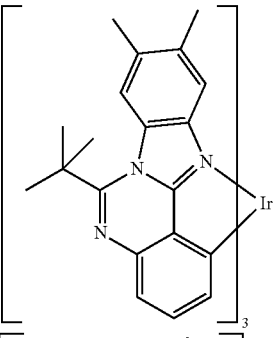
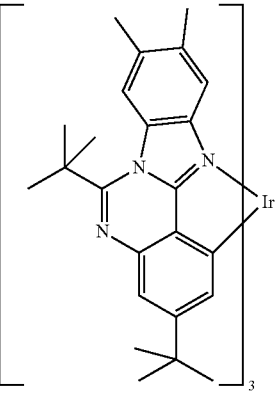
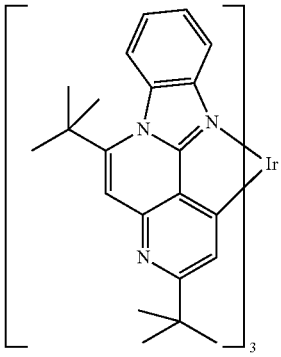
and where |HOMO| and |LUMO| are the modulus of the respective value, where the energy values indicated relate to isolated compounds and are determined by quantum-chemical calculations, wherein the bipolar host is selected from the group of the pyridines, pyrimidines, triazines, benzimidazoles, carbazoles, indenocarbazoles, indolocarbazoles, 1,10-phenanthrolines, 1,3,4-oxadiazoles, phosphine oxides, phenylsulfonyls, ketones, lactams and triarylamines, and wherein the neutral co-host is selected from the group of compounds

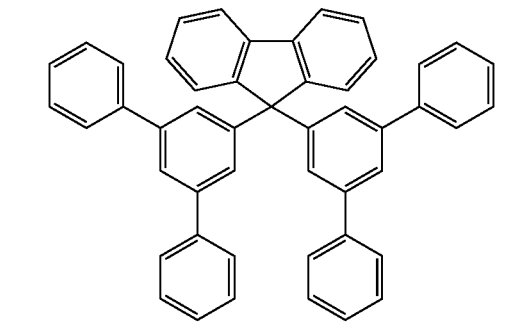

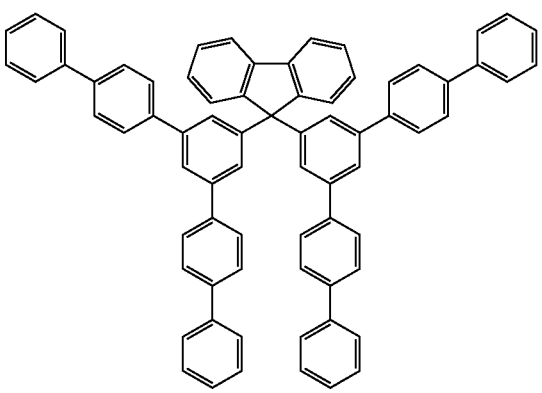

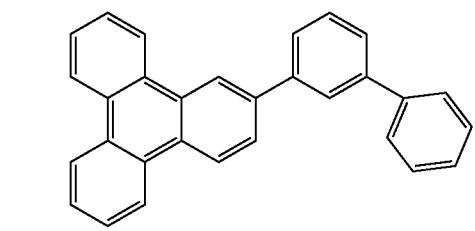

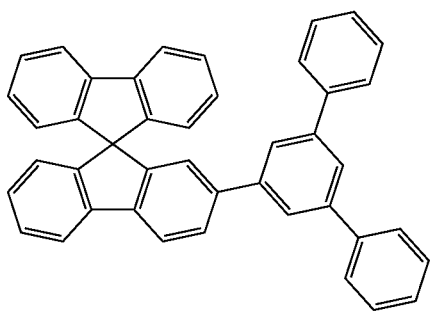

-continued

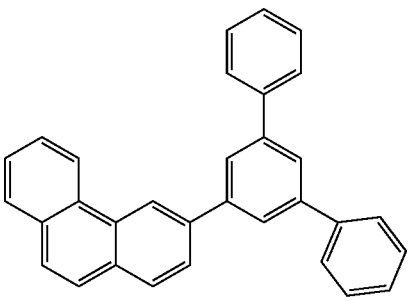

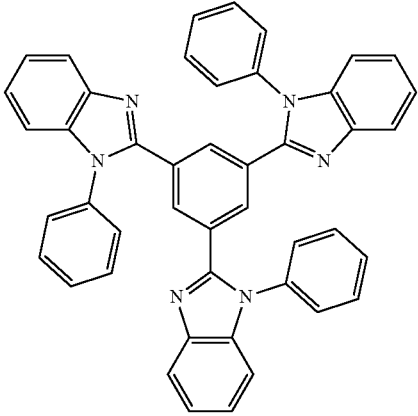

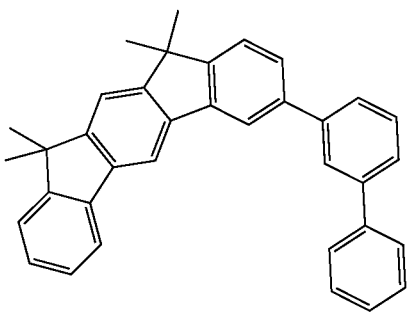

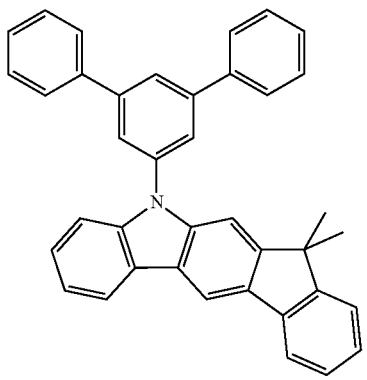

125
-continued
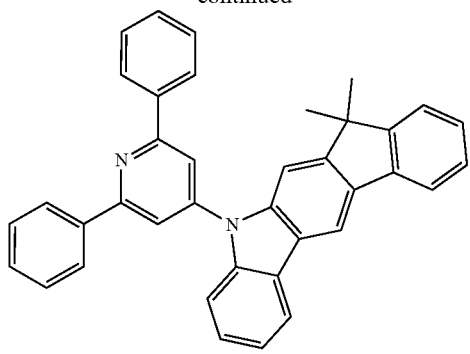
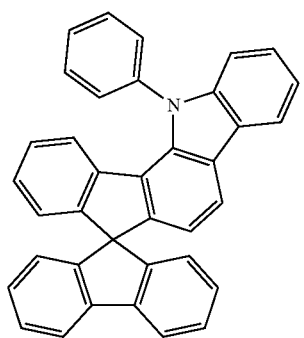
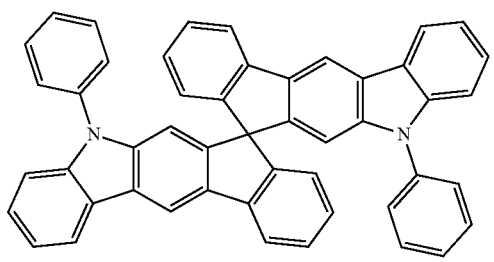
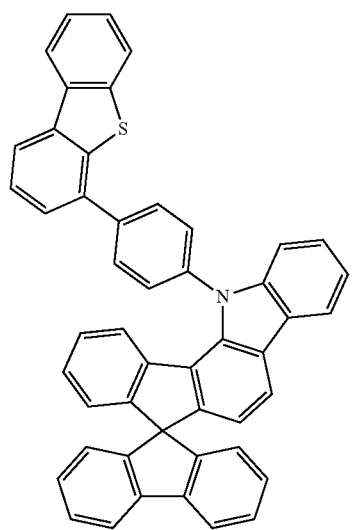
126
-continued
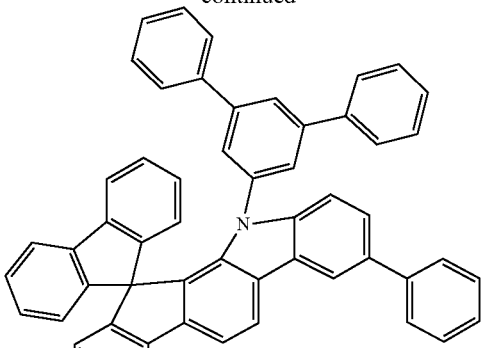
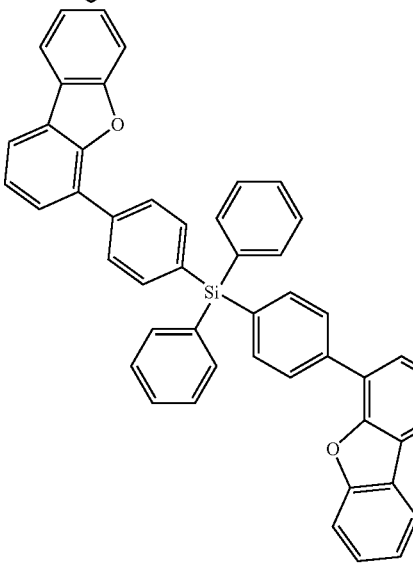
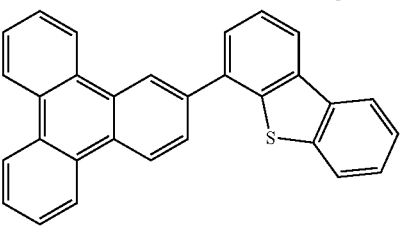
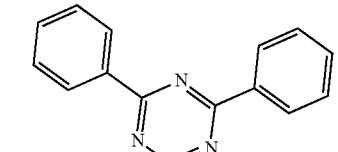
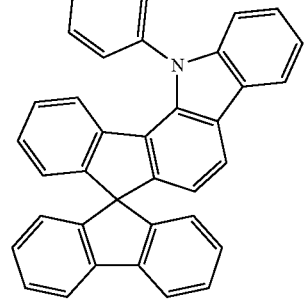

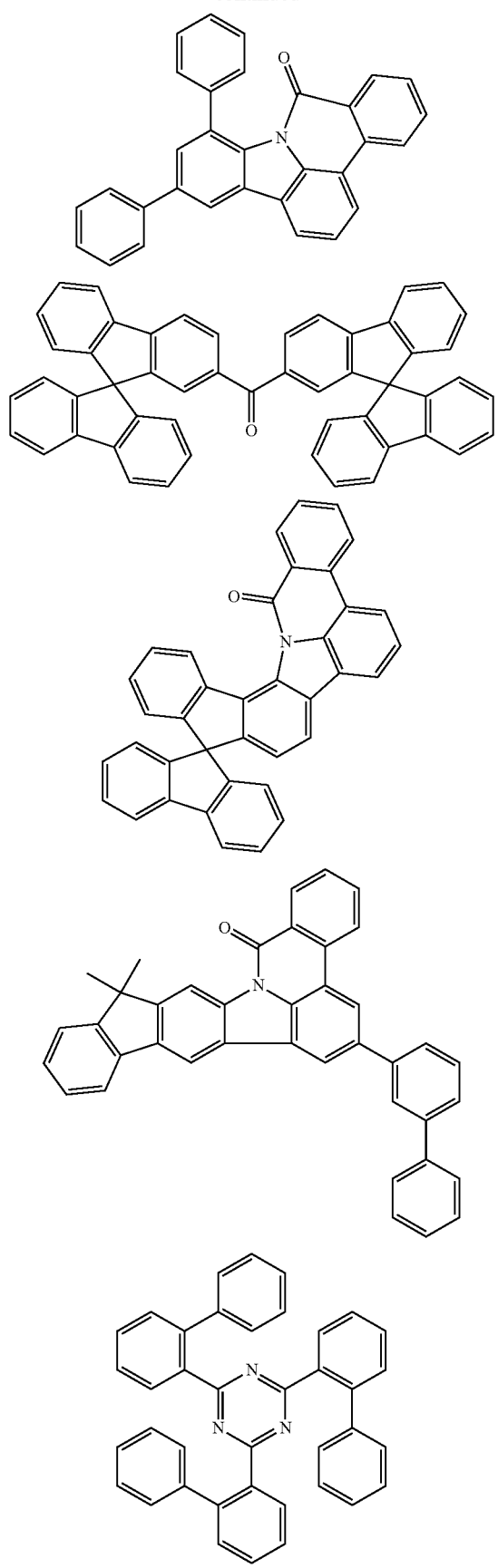
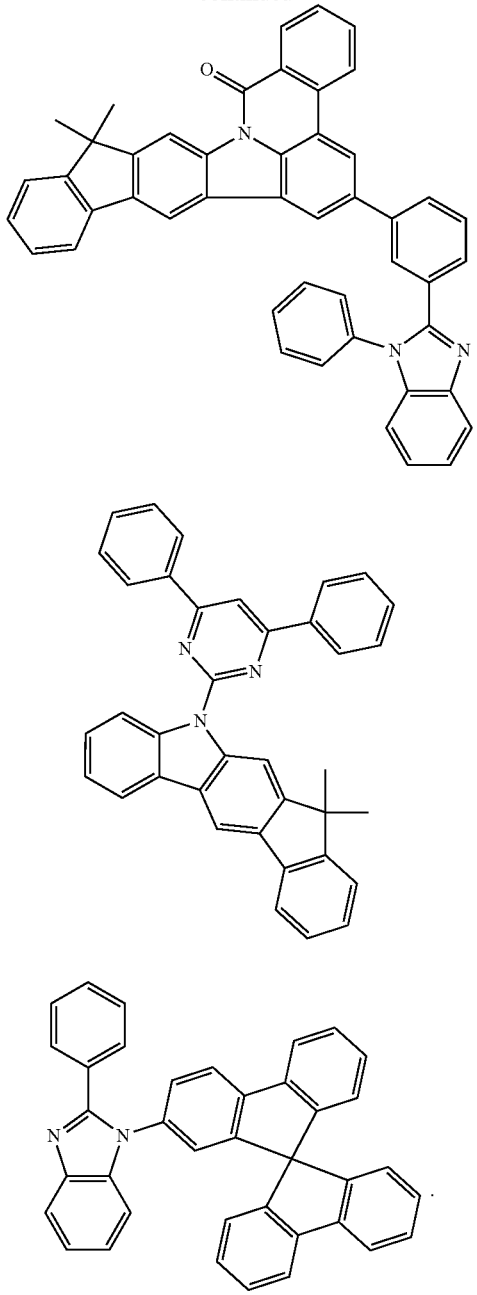
2. The composition according to claim 1, wherein the following conditions are satisfied:
|HOMO(*B*)|−|HOMO(*D*)|<0.15 eV and
|HOMO(*B*)|−|HOMO(*D*)|>−0.2 eV.
3. The composition according to claim 1, wherein the following condition is satisfied:
|HOMO(*C*)|−min{|HOMO(*D*)|;|HOMO(*B*)|}>0.4 eV,
or
|HOMO(*C*)|−min{|HOMO(*D*)|;|HOMO(*B*)|}>0.6 eV.

4. The composition according to claim 1, wherein the following condition is satisfied:

$||LUMO(B)|-|LUMO(C)||>0.4$ eV, or $||LUMO(B)|-|LUMO(C)||>0.6$ eV.

5. The composition according to claim 1, wherein the following conditions are satisfied:

$||LUMO(D)|-|LUMO(B)||<0.15$ eV and $||LUMO(D)|-|LUMO(B)||>-0.2$ eV, or $||LUMO(D)|-|LUMO(B)||<0.1$ eV and $||LUMO(D)|-|LUMO(B)||>-0.1$ eV.

6. The composition according to claim 1, wherein the following condition is satisfied:

$\max\{|LUMO(D)|;|LUMO(B)|\}-|LUMO(C)|>0.4$ eV, or $\max\{|LUMO(D)|;|LUMO(B)|\}-|LUMO(C)|>0.6$ eV.

7. The composition according to claim 1, wherein the following condition is satisfied:

$||HOMO(C)|-|HOMO(B)||>0.4$ eV, or $||HOMO(C)|-|HOMO(B)||>0.6$ eV.

8. The composition according to claim 1, wherein the composition comprises further organic functional materials which are selected from the group consisting of the hole-injection materials, hole-transport materials, hole-blocking materials, host materials, emitter materials, electron-blocking materials, electron-transport materials and electron-injection materials.

9. The composition according to claim 1, wherein the composition comprises a further host material selected from the group consisting of a bipolar host material, a neutral host material, a hole-transporting material, and an electron-transporting material.

10. The composition according to claim 1, wherein the composition comprises a further, second light-emitting dopant which is a phosphorescent emitter.

11. The composition according to claim 10, wherein the composition comprises a further, third light-emitting dopant which is a phosphorescent emitter.

12. The composition according to claim 1, wherein the composition comprises no further organic or inorganic constituents besides the said organic constituents.

13. A formulation comprising the composition according to claim 1 and at least one solvent.

14. A method for the production of an electronic device comprising utilizing the formulation according to claim 13 to process an emission layer of the device from solution.

15. A method comprising utilizing the composition according to claim 1 in an organic electronic device.

16. An organic electronic device comprising at least one composition according to claim 1, where the device is selected from the group consisting of organic integrated circuits (OICs), organic field-effect transistors (OFETs), organic thin-film transistors (OTFTs), organic electroluminescent devices, organic solar cells (OSCs), organic optical detectors and organic photoreceptors.

17. The device according to claim 16, wherein the device is an organic electroluminescent device selected from the group consisting of organic light-emitting transistors (OLETs), organic field-quench devices (OFQDs), organic light-emitting electrochemical cells (OLECs, LECs, LEECs), organic laser diodes (O-lasers) and organic light-emitting diodes (OLEDs).

18. The device according to claim 16, wherein it is an organic electroluminescent device which comprises the composition in the emission layer.

19. The device according to claim 18, wherein the emission layer comprises the composition and where a hole-transport layer which comprises a hole-transport material (HTM) is directly adjacent to the emission layer, where the following condition applies to the moduli of the HOMO energies of the bipolar host in the emission layer and of the hole-transport material in the hole-transport layer:

$||HOMO(B)|-|HOMO(HTM)||<0.3$ eV.

20. The device according to claim 18, wherein the emission layer comprises the composition and where an electron-transport layer which comprises an electron-transport material, ETM, is directly adjacent to the emission layer, where the following condition applies to the moduli of the LUMO energies of the bipolar host in the emission layer and of the electron-transport material in the electron-transport layer:

$||LUMO(B)|-|LUMO(ETM)||<0.3$ eV.

21. The composition according to claim 1, wherein the following conditions are satisfied:

$||HOMO(B)|-|HOMO(D)||<0.1$ eV and $||HOMO(B)|-|HOMO(D)||>-0.1$ eV.

22. The composition according to claim 1, wherein the bipolar host is a carbazole/triazine hybrid system, indenocarbazole/triazine hybrid system, indolocarbazole/triazine hybrid system, carbazole-carbazole/triazine hybrid system, indenocarbazole-carbazole/triazine hybrid system or an amine/triazine hybrid system.

* * * * *